(12) United States Patent
Brown et al.

(10) Patent No.: US 8,524,680 B2
(45) Date of Patent: Sep. 3, 2013

(54) HIGH POTENCY SIRNAS FOR REDUCING THE EXPRESSION OF TARGET GENES

(75) Inventors: David Brown, Austin, TX (US); Lance P. Ford, Austin, TX (US); Richard A. Jarvis, Austin, TX (US); Vince Pallotta, Austin, TX (US); Brittan L. Pasloske, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 168 days.

(21) Appl. No.: 12/550,625

(22) Filed: Aug. 31, 2009

(65) Prior Publication Data

US 2010/0221789 A1    Sep. 2, 2010

Related U.S. Application Data

(63) Continuation of application No. 10/355,820, filed on Jan. 31, 2003, now abandoned.

(60) Provisional application No. 60/353,332, filed on Feb. 1, 2002.

(51) Int. Cl.
*C12N 15/11* (2006.01)

(52) U.S. Cl.
USPC ........................................................ 514/44 A

(58) Field of Classification Search
USPC ........................................................ 514/44 A
See application file for complete search history.

(56) References Cited

U.S. PATENT DOCUMENTS

| | | | |
|---|---|---|---|
| 4,235,871 A | 11/1980 | Papahadjopoulos et al. |
| 4,415,732 A | 11/1983 | Caruthers et al. |
| 4,458,066 A | 7/1984 | Caruthers et al. |
| 4,501,728 A | 2/1985 | Geho et al. |
| 4,554,101 A | 11/1985 | Hopp |
| 4,659,774 A | 4/1987 | Webb et al. |
| 4,661,450 A | 4/1987 | Kempe et al. |
| 4,682,195 A | 7/1987 | Yimaz |
| 4,683,195 A | 7/1987 | Mullis et al. |
| 4,683,202 A | 7/1987 | Mullis |
| 4,684,611 A | 8/1987 | Schilperoort et al. |
| 4,704,362 A | 11/1987 | Itkura et al. |
| 4,737,323 A | 4/1988 | Martin et al. |
| 4,786,600 A | 11/1988 | Kramer et al. |
| 4,800,159 A | 1/1989 | Mullis et al. |
| 4,816,571 A | 3/1989 | Andrus et al. |
| 4,828,979 A | 5/1989 | Kievan et al. |
| 4,837,028 A | 6/1989 | Allen |
| 4,847,240 A | 7/1989 | Ryser |
| 4,849,513 A | 7/1989 | Smith et al. |
| 4,883,750 A | 11/1989 | Whitely et al. |
| 4,897,355 A | 1/1990 | Eppstein et al. |
| 4,910,300 A | 3/1990 | Urdea et al. |
| 4,952,496 A | 8/1990 | Studier et al. |
| 4,952,500 A | 8/1990 | Finnerty et al. |
| 4,959,463 A | 9/1990 | Froehler et al. |
| 5,013,830 A | 5/1991 | Ohtsuka |
| 5,026,645 A | 6/1991 | Kotani et al. |
| 5,037,735 A | 8/1991 | Khanna et al. |
| 5,037,745 A | 8/1991 | McAllister |
| 5,063,209 A | 11/1991 | Carter |
| 5,102,802 A | 4/1992 | McAllister |
| 5,141,813 A | 8/1992 | Nelson |
| 5,214,135 A | 5/1993 | Srivastava |
| 5,214,136 A | 5/1993 | Lin et al. |
| 5,221,619 A | 6/1993 | Itakura et al. |
| 5,223,618 A | 6/1993 | Cook et al. |
| 5,231,168 A | 7/1993 | Dziegiel et al. |
| 5,240,846 A | 8/1993 | Collins et al. |
| 5,241,060 A | 8/1993 | Engelhardt et al. |
| 5,260,433 A | 11/1993 | Engelhardt et al. |
| 5,264,423 A | 11/1993 | Cohen et al. |
| 5,264,566 A | 11/1993 | Froehler et al. |
| 5,276,019 A | 1/1994 | Cohen et al. |
| 5,279,721 A | 1/1994 | Schmid |
| 5,302,523 A | 4/1994 | Coffee et al. |
| 5,322,783 A | 6/1994 | Tomes et al. |
| 5,378,825 A | 1/1995 | Cook et al. |
| 5,384,253 A | 1/1995 | Krzyzek et al. |
| 5,391,723 A | 2/1995 | Priest |
| 5,428,148 A | 6/1995 | Reddy et al. |
| 5,446,137 A | 8/1995 | Maag et al. |
| 5,464,765 A | 11/1995 | Coffee et al. |
| 5,466,786 A | 11/1995 | Buhr et al. |
| 5,470,967 A | 11/1995 | Huie et al. |
| 5,480,980 A | 1/1996 | Seela |
| 5,489,527 A | 2/1996 | Wilson |

(Continued)

FOREIGN PATENT DOCUMENTS

| | | |
|---|---|---|
| CA | 2473944 | 7/2003 |
| EP | 0178863 | 10/1985 |

(Continued)

OTHER PUBLICATIONS

Parrish et al. Molecular Cell vol. 6, 1077-1087, 2000.*
SilencerTM siRNA Construction Kit-Protocol-Large Scale Synthesis and Purification of siRNAs, Catalog#1620, Ambion, Inc. Sep. 2002, pp. 1, 2, and 4-10.*
RNA Interference in Mammalian Cell Culture: Design, Execution and Analysis of the siRNA Effect TechNotes9(1), pp. 1-6, Feb. 2002.*
Dharmacon Research-Technical Info Technical Bulletin #003-Revision A siRNA Oligonucleotides for RNAi Applications, Aug. 20, 2001, pp. 1-12.*

(Continued)

*Primary Examiner* — Brian Whiteman

(57) ABSTRACT

The present invention provides improved methods of attenuating gene expression through the phenomenon of RNA interference. The invention provides methods of synthesis of double stranded RNAs (dsRNAs) of increased potency for use as small interfering RNA (siRNA). Surprisingly and unexpectedly, siRNAs made by the methods of the invention are significantly more potent than previously available siRNAs.

18 Claims, 12 Drawing Sheets

(56) References Cited

U.S. PATENT DOCUMENTS

| | | |
|---|---|---|
| 5,506,212 A | 4/1996 | Hoke et al. |
| 5,514,788 A | 5/1996 | Bennett et al. |
| 5,525,719 A | 6/1996 | Srivastava et al. |
| 5,538,877 A | 7/1996 | Lundquist et al. |
| 5,538,880 A | 7/1996 | Lundquist et al. |
| 5,550,318 A | 8/1996 | Adams et al. |
| 5,554,744 A | 9/1996 | Bhongle et al. |
| 5,563,055 A | 10/1996 | Townsend et al. |
| 5,565,350 A | 10/1996 | Kmiec |
| 5,573,913 A | 11/1996 | Rosemeyer et al. |
| 5,574,146 A | 11/1996 | Reddy et al. |
| 5,580,859 A | 12/1996 | Felgner et al. |
| 5,583,013 A | 12/1996 | Itakura et al. |
| 5,589,466 A | 12/1996 | Felgner et al. |
| 5,591,601 A | 1/1997 | Wagner et al. |
| 5,591,616 A | 1/1997 | Hiei et al. |
| 5,594,121 A | 1/1997 | Froehler et al. |
| 5,594,122 A | 1/1997 | Friesen |
| RE35,443 E | 2/1997 | DeFrancesco et al. |
| 5,602,240 A | 2/1997 | De Mesmaeker et al. |
| 5,602,244 A | 2/1997 | Caruthers et al. |
| 5,610,042 A | 3/1997 | Chang et al. |
| 5,610,289 A | 3/1997 | Cook et al. |
| 5,614,503 A | 3/1997 | Chaudhary et al. |
| 5,614,617 A | 3/1997 | Cook et al. |
| 5,623,070 A | 4/1997 | Cook et al. |
| 5,624,803 A | 4/1997 | Noonberg et al. |
| 5,637,683 A | 6/1997 | Usher et al. |
| 5,643,768 A | 7/1997 | Kawasaki |
| 5,645,897 A | 7/1997 | Andra |
| 5,652,099 A | 7/1997 | Conrad |
| 5,656,610 A | 8/1997 | Shuler et al. |
| 5,670,633 A | 9/1997 | Cook et al. |
| 5,672,697 A | 9/1997 | Buhr et al. |
| 5,677,124 A | 10/1997 | DuBois et al. |
| 5,681,947 A | 10/1997 | Bergstom et al. |
| 5,700,922 A | 12/1997 | Cook |
| 5,702,932 A | 12/1997 | Hoy et al. |
| 5,705,629 A | 1/1998 | Bhongle |
| 5,708,154 A | 1/1998 | Smith et al. |
| 5,712,257 A | 1/1998 | Carter |
| 5,714,606 A | 2/1998 | Acevedo et al. |
| 5,728,525 A | 3/1998 | Conrad |
| 5,734,039 A | 3/1998 | Calabretta |
| 5,734,040 A | 3/1998 | Weeks et al. |
| 5,736,131 A | 4/1998 | Bosch et al. |
| 5,736,392 A | 4/1998 | Hawley-Nelson et al. |
| 5,736,524 A | 4/1998 | Content et al. |
| 5,744,595 A | 4/1998 | Srivastava et al. |
| 5,763,167 A | 6/1998 | Conrad |
| 5,767,099 A | 6/1998 | Harris et al. |
| 5,776,905 A | 7/1998 | Gibbons et al. |
| 5,777,092 A | 7/1998 | Cook et al. |
| 5,777,153 A | 7/1998 | Lin et al. |
| 5,780,053 A | 7/1998 | Ashley et al. |
| 5,780,448 A | 7/1998 | Davis |
| 5,789,215 A | 8/1998 | Berns et al. |
| 5,792,847 A | 8/1998 | Buhr et al. |
| 5,795,715 A | 8/1998 | Livache et al. |
| 5,795,737 A | 8/1998 | Seed et al. |
| 5,801,154 A | 9/1998 | Baracchini et al. |
| 5,824,528 A | 10/1998 | Studier et al. |
| 5,830,430 A | 11/1998 | Unger et al. |
| 5,830,653 A | 11/1998 | Froehler et al. |
| 5,840,873 A | 11/1998 | Nelson et al. |
| 5,843,640 A | 12/1998 | Patterson et al. |
| 5,843,650 A | 12/1998 | Segev |
| 5,843,651 A | 12/1998 | Stimpson et al. |
| 5,846,708 A | 12/1998 | Hollis et al. |
| 5,846,709 A | 12/1998 | Segev |
| 5,846,717 A | 12/1998 | Brow et al. |
| 5,846,726 A | 12/1998 | Nadeau et al. |
| 5,846,729 A | 12/1998 | Wu et al. |
| 5,846,783 A | 12/1998 | Wu et al. |
| 5,849,487 A | 12/1998 | Hase et al. |
| 5,849,497 A | 12/1998 | Steinman |
| 5,849,546 A | 12/1998 | Sousa et al. |
| 5,849,547 A | 12/1998 | Cleuziat et al. |
| 5,849,902 A | 12/1998 | Arrow et al. |
| 5,851,548 A | 12/1998 | Dattagupta |
| 5,853,990 A | 12/1998 | Winger et al. |
| 5,853,992 A | 12/1998 | Glazer et al. |
| 5,853,993 A | 12/1998 | Dellinger et al. |
| 5,855,910 A | 1/1999 | Ashley et al. |
| 5,856,092 A | 1/1999 | Dale et al. |
| 5,858,652 A | 1/1999 | Laffler et al. |
| 5,858,988 A | 1/1999 | Wang |
| 5,859,221 A | 1/1999 | Cook et al. |
| 5,861,244 A | 1/1999 | Wang et al. |
| 5,863,732 A | 1/1999 | Richards |
| 5,863,753 A | 1/1999 | Haugland et al. |
| 5,866,331 A | 2/1999 | Singer et al. |
| 5,866,366 A | 2/1999 | Kallender |
| 5,869,320 A | 2/1999 | Studier et al. |
| 5,872,232 A | 2/1999 | Cook et al. |
| 5,882,864 A | 3/1999 | An et al. |
| 5,885,834 A | 3/1999 | Epstein |
| 5,886,165 A | 3/1999 | Kandimalla et al. |
| 5,889,136 A | 3/1999 | Scaringe et al. |
| 5,891,681 A | 4/1999 | Mallet et al. |
| 5,898,031 A | 4/1999 | Crooke |
| 5,905,024 A | 5/1999 | Mirzabekov et al. |
| 5,910,407 A | 6/1999 | Vogelstein et al. |
| 5,912,124 A | 6/1999 | Kumar |
| 5,912,145 A | 6/1999 | Stanley |
| 5,912,148 A | 6/1999 | Eggerding |
| 5,916,776 A | 6/1999 | Kumar |
| 5,916,779 A | 6/1999 | Pearson |
| 5,919,630 A | 7/1999 | Nadeau et al. |
| 5,922,574 A | 7/1999 | Minter |
| 5,925,517 A | 7/1999 | Tyagi et al. |
| 5,928,862 A | 7/1999 | Morrison |
| 5,928,869 A | 7/1999 | Nadeau et al. |
| 5,928,905 A | 7/1999 | Stemmer et al. |
| 5,928,906 A | 7/1999 | Koster et al. |
| 5,929,042 A | 7/1999 | Troy et al. |
| 5,929,227 A | 7/1999 | Glazer et al. |
| 5,932,413 A | 8/1999 | Celebuski |
| 5,932,451 A | 8/1999 | Wang et al. |
| 5,935,791 A | 8/1999 | Nadeau et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,955,589 A | 9/1999 | Cook et al. |
| 5,965,720 A | 10/1999 | Gryaznov et al. |
| 5,981,274 A | 11/1999 | Tyrrell et al. |
| 5,990,479 A | 11/1999 | Weiss et al. |
| 5,994,624 A | 11/1999 | Trolinder et al. |
| 5,998,135 A | 12/1999 | Rabbani et al. |
| 5,998,203 A | 12/1999 | Matulic-Adamic et al. |
| 6,005,087 A | 12/1999 | Cook et al. |
| 6,015,886 A | 1/2000 | Dale et al. |
| 6,015,893 A | 1/2000 | Cance et al. |
| 6,037,463 A | 3/2000 | Uhlmann et al. |
| 6,048,974 A | 4/2000 | Gryaznov et al. |
| 6,051,386 A | 4/2000 | Lerner |
| 6,083,482 A | 7/2000 | Wang |
| 6,087,484 A | 7/2000 | Goodchild |
| 6,107,094 A | 8/2000 | Crooke |
| 6,114,152 A | 9/2000 | Serafini et al. |
| 6,127,124 A | 10/2000 | Leeds et al. |
| 6,133,024 A | 10/2000 | Helene et al. |
| 6,214,804 B1 | 4/2001 | Felgner et al. |
| 6,248,724 B1 | 6/2001 | Moore et al. |
| 6,251,666 B1 | 6/2001 | Beigelman |
| 6,251,873 B1 | 6/2001 | Furusako et al. |
| 6,262,252 B1 | 7/2001 | Wolff et al. |
| 6,268,490 B1 | 7/2001 | Imanishi et al. |
| 6,372,433 B1 | 4/2002 | Baker et al. |
| 6,376,179 B1 | 4/2002 | Laayoun |
| 6,455,292 B1 | 9/2002 | Shu et al. |
| 6,489,307 B1 | 12/2002 | Phillips et al. |
| 6,495,663 B1 | 12/2002 | Rothbard et al. |

| Patent | Date | Inventor |
|---|---|---|
| 6,506,559 B1 | 1/2003 | Fire et al. |
| 6,525,191 B1 | 2/2003 | Ramasamy |
| 6,573,099 B2 | 6/2003 | Graham |
| 6,573,374 B1 * | 6/2003 | Muehlegger et al. ...... 536/26.26 |
| 6,579,856 B2 | 6/2003 | Mercola |
| 6,638,767 B2 | 10/2003 | Unger et al. |
| 6,639,059 B1 | 10/2003 | Kochkine et al. |
| 6,670,461 B1 | 12/2003 | Wengel et al. |
| 6,673,611 B2 | 1/2004 | Thompson et al. |
| 6,680,301 B2 | 1/2004 | Berg et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 6,849,726 B2 | 2/2005 | Usman et al. |
| 6,953,656 B2 | 10/2005 | Jacobson et al. |
| 7,022,828 B2 | 4/2006 | McSwiggen et al. |
| 7,034,133 B2 | 4/2006 | Wengel et al. |
| 7,053,207 B2 | 5/2006 | Wengel |
| 7,056,704 B2 | 6/2006 | Tuschl et al. |
| 7,060,809 B2 | 6/2006 | Wengel et al. |
| 7,074,558 B2 | 7/2006 | Haydock et al. |
| 7,078,196 B2 * | 7/2006 | Tuschl et al. .................. 435/91.1 |
| 7,084,125 B2 | 8/2006 | Wengel |
| 7,176,304 B2 | 2/2007 | McSwiggen et al. |
| 7,368,240 B2 | 5/2008 | Van et al. |
| 7,399,586 B2 | 7/2008 | Klinghoffer et al. |
| 7,452,987 B2 | 11/2008 | Giese et al. |
| 7,528,118 B2 | 5/2009 | Soutschek et al. |
| 7,538,095 B2 | 5/2009 | Fire et al. |
| 7,553,830 B2 | 6/2009 | Beigelman et al. |
| 7,556,944 B2 | 7/2009 | Myers et al. |
| 7,560,438 B2 | 7/2009 | Fire et al. |
| 7,566,700 B2 | 7/2009 | Walker et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,576,119 B2 | 8/2009 | Ravikumar et al. |
| 7,576,262 B2 | 8/2009 | Wang et al. |
| 7,579,451 B2 | 8/2009 | Manoharan et al. |
| 7,582,744 B2 | 9/2009 | Manoharan et al. |
| 7,582,745 B2 | 9/2009 | Sah et al. |
| 7,592,322 B2 | 9/2009 | Barik |
| 7,595,387 B2 | 9/2009 | Leake et al. |
| 7,615,618 B2 | 11/2009 | Manoharan |
| 7,622,633 B2 | 11/2009 | Fire et al. |
| 7,626,014 B2 | 12/2009 | Manoharan et al. |
| 7,629,321 B2 | 12/2009 | Crooke |
| 7,632,932 B2 | 12/2009 | Manoharan et al. |
| 7,635,769 B2 | 12/2009 | Uhlmann et al. |
| 7,659,391 B2 * | 2/2010 | De Backer et al. .......... 536/25.3 |
| 7,687,617 B2 | 3/2010 | Thrue et al. |
| 7,691,997 B2 | 4/2010 | Khvorova et al. |
| 7,695,902 B2 | 4/2010 | Crooke |
| 7,695,964 B2 | 4/2010 | Maina et al. |
| 7,700,758 B2 | 4/2010 | Tzertzinis et al. |
| 7,704,688 B2 | 4/2010 | Baulcombe et al. |
| 7,723,512 B2 | 5/2010 | Manoharan |
| 7,732,417 B2 | 6/2010 | Beach et al. |
| 7,732,593 B2 | 6/2010 | Zamore et al. |
| 7,737,125 B2 | 6/2010 | Worm |
| 7,750,144 B2 | 7/2010 | Zamore et al. |
| 7,763,590 B2 | 7/2010 | Kreutzer |
| 7,772,203 B2 | 8/2010 | Zamore et al. |
| 7,772,387 B2 | 8/2010 | Manoharan et al. |
| 7,786,290 B2 | 8/2010 | Woppmann et al. |
| 7,790,691 B2 | 9/2010 | Kraynack et al. |
| 7,790,878 B2 | 9/2010 | Barik |
| 7,795,422 B2 | 9/2010 | McSwiggen et al. |
| 7,795,423 B2 | 9/2010 | Heindl et al. |
| 7,803,930 B2 | 9/2010 | Crooke et al. |
| 7,812,149 B2 | 10/2010 | Prakash et al. |
| 7,834,170 B2 | 11/2010 | Khvorova et al. |
| 7,834,171 B2 | 11/2010 | Leake et al. |
| 7,923,206 B2 | 4/2011 | Robertson et al. |
| 7,923,207 B2 | 4/2011 | Robertson et al. |
| 7,923,547 B2 | 4/2011 | McSwiggen et al. |
| 7,928,217 B2 | 4/2011 | Vornlocher et al. |
| 7,956,176 B2 | 6/2011 | McSwiggen et al. |
| 7,964,578 B2 | 6/2011 | Vargeese et al. |
| 8,058,255 B2 | 11/2011 | Ford et al. |
| 8,097,710 B2 | 1/2012 | Baulcombe et al. |
| 8,119,610 B2 | 2/2012 | Yang et al. |
| 2002/0086356 A1 | 7/2002 | Tuschl et al. |
| 2002/0162126 A1 | 10/2002 | Beach et al. |
| 2002/0165189 A1 | 11/2002 | Crooke |
| 2002/0173478 A1 | 11/2002 | Gewirtz |
| 2002/0197641 A1 | 12/2002 | Mine-Golomb |
| 2003/0009295 A1 | 1/2003 | Markowitz et al. |
| 2003/0032593 A1 | 2/2003 | Wender et al. |
| 2003/0044941 A1 | 3/2003 | Crooke |
| 2003/0077609 A1 | 4/2003 | Jakobsen et al. |
| 2003/0108923 A1 | 6/2003 | Tuschl et al. |
| 2003/0119104 A1 | 6/2003 | Perkins et al. |
| 2003/0143732 A1 | 7/2003 | Fosnaugh et al. |
| 2003/0153519 A1 | 8/2003 | Kay et al. |
| 2003/0166282 A1 | 9/2003 | Brown et al. |
| 2003/0203868 A1 | 10/2003 | Bushman et al. |
| 2003/0224377 A1 | 12/2003 | Wengel et al. |
| 2003/0224432 A1 | 12/2003 | Myers et al. |
| 2004/0014108 A1 | 1/2004 | Eldrup et al. |
| 2004/0014113 A1 | 1/2004 | Yang et al. |
| 2004/0014956 A1 | 1/2004 | Woolf et al. |
| 2004/0029275 A1 | 2/2004 | Brown et al. |
| 2004/0033602 A1 | 2/2004 | Ford et al. |
| 2004/0038921 A1 | 2/2004 | Kreutzer et al. |
| 2004/0053875 A1 | 3/2004 | Kreutzer et al. |
| 2004/0054155 A1 | 3/2004 | Woolf et al. |
| 2004/0058886 A1 | 3/2004 | Scaringe |
| 2004/0067882 A1 | 4/2004 | Alsobrook et al. |
| 2004/0072779 A1 | 4/2004 | Kreutzer et al. |
| 2004/0078836 A1 | 4/2004 | Farese et al. |
| 2004/0091926 A1 | 5/2004 | Liu et al. |
| 2004/0096843 A1 | 5/2004 | Rossi et al. |
| 2004/0102408 A1 | 5/2004 | Kreutzer et al. |
| 2004/0147022 A1 | 7/2004 | Baker et al. |
| 2004/0171031 A1 | 9/2004 | Baker et al. |
| 2004/0171033 A1 | 9/2004 | Baker et al. |
| 2004/0171570 A1 | 9/2004 | Allerson et al. |
| 2004/0175703 A1 | 9/2004 | Kreutzer et al. |
| 2004/0176282 A1 | 9/2004 | Dalby et al. |
| 2004/0180351 A1 | 9/2004 | Giese et al. |
| 2004/0192626 A1 | 9/2004 | McSwiggen et al. |
| 2004/0198640 A1 | 10/2004 | Leake et al. |
| 2004/0203024 A1 | 10/2004 | Baker et al. |
| 2004/0203145 A1 | 10/2004 | Zamore et al. |
| 2004/0219565 A1 | 11/2004 | Kauppinen et al. |
| 2004/0224405 A1 | 11/2004 | Leake et al. |
| 2004/0229266 A1 | 11/2004 | Tuschl et al. |
| 2004/0248094 A1 | 12/2004 | Ford et al. |
| 2004/0248299 A1 | 12/2004 | Jayasena et al. |
| 2004/0259097 A1 | 12/2004 | De Backer et al. |
| 2004/0259247 A1 * | 12/2004 | Tuschl et al. .................. 435/375 |
| 2005/0020521 A1 | 1/2005 | Rana |
| 2005/0020525 A1 | 1/2005 | McSwiggen et al. |
| 2005/0026160 A1 | 2/2005 | Allerson et al. |
| 2005/0026278 A1 | 2/2005 | Tuschl et al. |
| 2005/0058982 A1 | 3/2005 | Han et al. |
| 2005/0080246 A1 | 4/2005 | Allerson et al. |
| 2005/0100907 A1 | 5/2005 | Kreutzer et al. |
| 2005/0107325 A1 | 5/2005 | Manoharan et al. |
| 2005/0119214 A1 | 6/2005 | Manoharan et al. |
| 2005/0130201 A1 | 6/2005 | Deras et al. |
| 2005/0176018 A1 | 8/2005 | Thompson et al. |
| 2005/0176045 A1 | 8/2005 | Fedorov et al. |
| 2005/0203043 A1 | 9/2005 | Fedorov et al. |
| 2005/0214823 A1 | 9/2005 | Blume et al. |
| 2005/0223427 A1 | 10/2005 | Leake et al. |
| 2005/0234006 A1 | 10/2005 | Tuschl et al. |
| 2005/0234007 A1 | 10/2005 | Tuschl et al. |
| 2005/0244858 A1 | 11/2005 | Rossi et al. |
| 2005/0245475 A1 | 11/2005 | Khvorova et al. |
| 2005/0246794 A1 | 11/2005 | Khvorova et al. |
| 2005/0255487 A1 | 11/2005 | Khvorova et al. |
| 2005/0256071 A1 | 11/2005 | Davis |
| 2005/0287566 A1 | 12/2005 | Wengel |
| 2006/0009409 A1 | 1/2006 | Wolf et al. |
| 2006/0134787 A1 | 6/2006 | Zamore et al. |
| 2006/0142228 A1 | 6/2006 | Ford et al. |

| | | | |
|---|---|---|---|
| 2006/0166910 A1 | 7/2006 | Tuschl et al. | |
| 2006/0217334 A1 | 9/2006 | McSwiggen et al. | |
| 2006/0217335 A1 | 9/2006 | McSwiggen et al. | |
| 2006/0217336 A1 | 9/2006 | McSwiggen et al. | |
| 2006/0217337 A1 | 9/2006 | McSwiggen et al. | |
| 2006/0223777 A1 | 10/2006 | Vermeulen et al. | |
| 2006/0247428 A1 | 11/2006 | McSwiggen et al. | |
| 2006/0247429 A1 | 11/2006 | McSwiggen et al. | |
| 2006/0276635 A1 | 12/2006 | McSwiggen et al. | |
| 2006/0287266 A1 | 12/2006 | McSwiggen et al. | |
| 2006/0293271 A1 | 12/2006 | McSwiggen et al. | |
| 2007/0003960 A1 | 1/2007 | Tuschl et al. | |
| 2007/0003961 A1 | 1/2007 | Tuschl et al. | |
| 2007/0003962 A1 | 1/2007 | Tuschl et al. | |
| 2007/0004663 A1 | 1/2007 | McSwiggen et al. | |
| 2007/0004665 A1 | 1/2007 | McSwiggen et al. | |
| 2007/0004667 A1 | 1/2007 | McSwiggen et al. | |
| 2007/0031844 A1 | 2/2007 | Khvorova et al. | |
| 2007/0039072 A1 | 2/2007 | Khvorova et al. | |
| 2007/0093445 A1 | 4/2007 | Tuschl et al. | |
| 2007/0111228 A1 | 5/2007 | Jayasena et al. | |
| 2007/0167384 A1 | 7/2007 | Leake et al. | |
| 2007/0173476 A1 | 7/2007 | Leake et al. | |
| 2007/0265438 A1 | 11/2007 | Khvorova et al. | |
| 2008/0086002 A1 | 4/2008 | Khvorova et al. | |
| 2008/0160594 A1 | 7/2008 | Woolf | |
| 2009/0023216 A1 | 1/2009 | Woolf | |
| 2009/0093433 A1 | 4/2009 | Woolf et al. | |
| 2010/0075423 A1 | 3/2010 | Ford et al. | |
| 2010/0136695 A1 | 6/2010 | Woolf | |
| 2010/0159591 A1 | 6/2010 | Ford et al. | |
| 2010/0184039 A1 | 7/2010 | Ford et al. | |
| 2010/0221789 A1 | 9/2010 | Brown et al. | |
| 2010/0298408 A1 | 11/2010 | Woolf et al. | |
| 2011/0151558 A1 | 6/2011 | Brown et al. | |
| 2012/0028312 A1 | 2/2012 | Ford et al. | |
| 2012/0122217 A1 | 5/2012 | Brown et al. | |

FOREIGN PATENT DOCUMENTS

| | | |
|---|---|---|
| EP | 0204401 | 12/1986 |
| EP | 0266032 | 8/1987 |
| EP | 0726319 | 4/2001 |
| EP | 1560931 | 6/2002 |
| EP | 0990903 | 3/2003 |
| EP | 1470148 | 8/2003 |
| EP | 1389637 | 2/2004 |
| EP | 1606406 | 9/2004 |
| EP | 1532271 | 4/2005 |
| EP | 1572902 | 8/2005 |
| EP | 1550719 | 12/2008 |
| EP | 1478656 | 9/2009 |
| EP | 1718747 | 10/2009 |
| EP | 1537227 | 2/2010 |
| EP | 2213292 | 8/2010 |
| EP | 2213737 | 8/2010 |
| EP | 2128248 | 5/2011 |
| EP | 2351836 | 8/2011 |
| EP | 2221377 | 10/2011 |
| EP | 2455467 | 5/2012 |
| GB | 2406169 | 3/2005 |
| WO | WO 88/10315 | 6/1988 |
| WO | WO 90/14074 | 11/1990 |
| WO | WO 91/02818 | 3/1991 |
| WO | WO 91/05866 | 5/1991 |
| WO | WO 91/16024 | 10/1991 |
| WO | WO 91/17424 | 11/1991 |
| WO | WO 92/03464 | 3/1992 |
| WO | WO 92/03568 | 3/1992 |
| WO | WO 93/09236 | 5/1993 |
| WO | WO 94/01550 | 1/1994 |
| WO | WO 94/08003 | 4/1994 |
| WO | WO 94/23028 | 10/1994 |
| WO | WO 95/10305 | 4/1995 |
| WO | WO 95/18139 | 7/1995 |
| WO | WO 95/22533 | 8/1995 |
| WO | WO 96/07432 | 3/1996 |
| WO | WO 97/11085 | 3/1997 |
| WO | WO 98/00547 | 1/1998 |
| WO | WO 98/01898 | 1/1998 |
| WO | WO 98/13526 | 4/1998 |
| WO | WO 99/04775 | 2/1999 |
| WO | WO 99/14346 | 3/1999 |
| WO | WO 99/20298 | 4/1999 |
| WO | WO 99/32619 | 7/1999 |
| WO | WO 00/01846 | 1/2000 |
| WO | WO 00/26413 | 5/2000 |
| WO | WO 00/27422 | 5/2000 |
| WO | WO 00/44895 | 8/2000 |
| WO | WO 00/44914 | 8/2000 |
| WO | WO 00/54802 | 9/2000 |
| WO | WO 00/55378 | 9/2000 |
| WO | WO 00/61595 | 10/2000 |
| WO | WO 00/63364 | 10/2000 |
| WO | WO 01/25422 | 4/2001 |
| WO | WO 01/36646 | 5/2001 |
| WO | WO 01/46473 | 6/2001 |
| WO | WO 01/52904 | 7/2001 |
| WO | WO 01/68836 | 9/2001 |
| WO | WO 01/72995 | 10/2001 |
| WO | WO 01/75164 | 10/2001 |
| WO | WO 01/96584 | 12/2001 |
| WO | WO 02/44321 | 6/2002 |
| WO | WO 02/094848 | 11/2002 |
| WO | WO 03/064626 | 7/2003 |
| WO | WO 03/064625 | 8/2003 |
| WO | WO 03/070918 | 8/2003 |
| WO | WO 03/100059 | 12/2003 |
| WO | WO 03/102214 | 12/2003 |
| WO | WO 03/106630 | 12/2003 |
| WO | WO 03/106631 | 12/2003 |
| WO | WO 2004/044132 | 5/2004 |
| WO | WO 2004/044133 | 5/2004 |
| WO | WO 2004/046320 | 6/2004 |
| WO | WO 2004/065579 | 8/2004 |
| WO | WO 2004/090105 | 10/2004 |
| WO | WO 2004/099387 | 11/2004 |
| WO | WO 2005/035004 | 4/2005 |

OTHER PUBLICATIONS

Tuschl et al. Genes & Development 13:3191-3197, 1999.*
U.S. Appl. No. 10/298,480; Office Action mailed Feb. 10, 2006.
U.S. Appl. No. 10/298,480; Office Action mailed Oct. 10, 2006.
U.S. Appl. No. 10/298,480; Final Office Action mailed May 30, 2007.
U.S. Appl. No. 10/298,480; Final Office Action mailed Jan. 24, 2008.
U.S. Appl. No. 10/298,480; Final Office Action mailed Dec. 3, 2008.
U.S. Appl. No. 10/298,480; Final Office Action mailed Jul. 10, 2009.
U.S. Appl. No. 10/298,480; Final Office Action mailed Mar. 22, 2010.
U.S. Appl. No. 10/298,480; Office Action mailed Jun. 9, 2011.
U.S. Appl. No. 10/298,480; Office Action mailed Sep. 21, 2011.
U.S. Appl. No. 10/298,480; Final Office Action mailed Nov. 28, 2011.
U.S. Appl. No. 10/298,480; Office Action mailed Mar. 5, 2012.
U.S. Appl. No. 10/298,480; Office Action mailed Jul. 24, 2012.
U.S. Appl. No. 10/355,820; Office Action mailed Nov. 29, 2005.
U.S. Appl. No. 10/355,820; Final Office Action mailed May 30, 2006.
U.S. Appl. No. 10/355,820; Office Action mailed Feb. 5, 2007.
U.S. Appl. No. 10/355,820; Final Office Action mailed Jan. 3, 2008.
U.S. Appl. No. 10/355,820; Office Action mailed Aug. 19, 2008.
U.S. Appl. No. 10/355,820; Office Action mailed Mar. 31, 2009.
U.S. Appl. No. 10/357,529; Office Action mailed Nov. 17, 2005.
U.S. Appl. No. 10/357,529; Office Action mailed Jun. 23, 2006.
U.S. Appl. No. 10/357,529; Final Office Action mailed Jan. 25, 2007.
U.S. Appl. No. 10/357,529; Office Action mailed Oct. 3, 2007.
U.S. Appl. No. 10/357,826; Office Action mailed Jul. 11, 2007.
U.S. Appl. No. 10/357,826; Office Action mailed Sep. 8, 2008.
U.S. Appl. No. 10/357,826; Office Action mailed Jun. 3, 2009.
U.S. Appl. No. 10/360,772; Office Action mailed Aug. 23, 2005.
U.S. Appl. No. 10/360,772; Final Office Action mailed May 16, 2006.
U.S. Appl. No. 10/360,772; Office Action mailed Oct. 30, 2006.
U.S. Appl. No. 10/360,772; Final Office Action mailed May 15, 2007.
U.S. Appl. No. 10/360,772; Final Office Action mailed Jan. 7, 2008.
U.S. Appl. No. 10/360,772; Final Office Action mailed Sep. 22, 2008.
U.S. Appl. No. 10/360,772; Office Action mailed Apr. 28, 2009.

U.S. Appl. No. 10/460,775; Office Action mailed Apr. 25, 2006.
U.S. Appl. No. 10/460,775; Office Action mailed Apr. 19, 2007.
U.S. Appl. No. 10/460,775; Office Action mailed Aug. 22, 2007.
U.S. Appl. No. 10/460,775; Office Action mailed Feb. 11, 2008.
U.S. Appl. No. 10/460,775; Office Action mailed Oct. 20, 2008.
U.S. Appl. No. 10/460,775; Office Action mailed Apr. 16, 2009.
U.S. Appl. No. 11/020,560; Office Action mailed Feb. 6, 2007.
U.S. Appl. No. 11/020,560; Office Action mailed Dec. 7, 2007.
U.S. Appl. No. 11/020,560; Office Action mailed Aug. 5, 2008.
U.S. Appl. No. 11/020,560; Notice of Allowance mailed Mar. 16, 2009.
U.S. Appl. No. 11/049,636; Office Action mailed Apr. 17, 2007.
U.S. Appl. No. 11/049,636; Final Office Action mailed Dec. 31, 2007.
U.S. Appl. No. 11/776,313; Office Action mailed Sep. 17, 2009.
U.S. Appl. No. 11/776,313; Final Office Action mailed Jun. 29, 2010.
U.S. Appl. No. 12/062,380; Office Action mailed Mar. 24, 2010.
U.S. Appl. No. 12/062,380; Office Action mailed Nov. 12, 2010.
U.S. Appl. No. 12/062,380; Final Office Action mailed Jun. 20, 2011.
U.S. Appl. No. 12/484,948; Office Action mailed Oct. 12, 2010.
U.S. Appl. No. 12/484,948 ; Office Action mailed Mar. 28, 2011.
U.S. Appl. No. 12/484,948 ; Notice of Allowance mailed Jul. 15, 2011.
U.S. Appl. No. 12/484,948; Issue Notification mailed Oct. 26, 2011.
U.S. Appl. No. 12/550,625; Office Action mailed May 5, 2011.
U.S. Appl. No. 12/550,625; Final Office Action mailed Aug. 30, 2011.
U.S. Appl. No. 12/550,625; Office Action mailed Dec. 13, 2012.
U.S. Appl. No. 12/550,625; Notice of Allowance mailed Apr. 3, 2013.
U.S. Appl. No. 12/559,276; Office Action mailed Apr. 28, 2010.
U.S. Appl. No. 12/559,276; Office Action mailed Jan. 5, 2011.
U.S. Appl. No. 12/568,244; Office Action mailed May 21, 2010.
U.S. Appl. No. 12/568,244; Office Action mailed Feb. 2, 2011.
U.S. Appl. No. 12/630,523; Office Action mailed Dec. 20, 2011.
U.S. Appl. No. 12/630,523; Final Office Action mailed May 31, 2012.
U.S. Appl. No. 12/630,523; Office Action mailed Apr. 9, 2013.
U.S. Appl. No. 13/039,653; Office Action mailed Jul. 7, 2011.
U.S. Appl. No. 13/039,653; Final Office Action mailed Nov. 28, 2011.
U.S. Appl. No. 13/196,710; Office Action mailed May 18, 2012.
U.S. Appl. No. 13/211,250; Office Action mailed May 11, 2012.
U.S. Appl. No. 13/277,957; Office Action mailed Feb. 8, 2013.
U.S. Appl. No. 13/360,148; Office Action mailed Apr. 19, 2012.
U.S. Appl. No. 13/360,148; Office Action mailed Sep. 5, 2012.
U.S. Appl. No. 60/353,203; Provisional Application Filed Feb. 1, 2002.
U.S. Appl. No. 60/353,381; Provisional Application Filed Feb. 1, 2002.
U.S. Appl. No. 60/436,238; Provisional Application Filed Dec. 23, 2002.
U.S. Appl. No. 60/438,608; Provisional Application Filed Jan. 7, 2003.
U.S. Appl. No. 60/540,552; Provisional Application Filed Feb. 2, 2004.
AU 2003208962; Examiner's Report mailed Jul. 25, 2007.
CA 2,474,910; Office Action mailed Mar. 15, 2010.
CA 2,474,910; Office Action mailed Jun. 30, 2011.
CA 2,475,003; Office Action mailed Mar. 15, 2010.
CA 2,475,003; Office Action mailed Aug. 9, 2011.
GB0500265.4; Examination Report under Section 18(3) mailed May 27, 2005.
GB0500265.4; Examination Report under Section 18(3) mailed Nov. 29, 2005.
GB0500265.4; Examination Report under Section 18(3) mailed Jul. 28, 2006.
GB Patent No. 2406169; Certificate of Grant of Patent dated Nov. 1, 2006.
EP 03707687.4; Supplementary European Search Report mailed Apr. 3, 2008.
EP 03707687.4; EPO Communication pursuant to Article 94(3) EPC mailed Nov. 14, 2008.
EP 03707687.4; EPO Rule 71(3) Communication—Notice of Grant mailed Apr. 27, 2009.
EP03707687.4; Decision to Grant mailed Aug. 20, 2009.
EP 03708928.1; EPO Search Report mailed Mar. 14, 2007.
EP 03708928.1; EPO Communication pursuant to Article 96(2) EPC mailed Jun. 15, 2007.
EP 03708928.1; Office Action mailed on Feb. 2, 2010.
EP 03708928.1; EPO Communication pursuant to Article 94(3) EPC mailed Mar. 28, 2013.
EP 03708949.7; International Search Report mailed Jan. 11, 2008.
EP 03708949.7; European Examination Report mailed Jun. 8, 2009.
EP 03708949.7; Office Action mailed Dec. 21, 2010.
EP 03708949.7; Rule 71(3) Communication—Notice of Grant mailed Apr. 16, 2012.
EP 03708949.7; Decision to Grant mailed Jun. 21, 2012.
EP 03741956.1; EPO Communication pursuant to Article 96(2) EPC mailed Jan. 16, 2007.
EP 03741956.1; EPO Communication pursuant to Article 94(3) EPC mailed Jul. 15, 2008.
EP 03741956.1; Office Action mailed Apr. 21, 2010.
EP 09166406.0; Extended European Search Report mailed Oct. 28, 2009.
EP 09166406.0; Rule 71(3) Communication—Notice of Grant mailed Sep. 29, 2010.
EP 09166406.0; Decision to Grant mailed Apr. 7, 2011.
EP 10151247.3; Extended European Search Report mailed Jul. 23, 2010.
EP 10151247.3; Office Action Mailed Nov. 24, 2010.
EP 10151247.3; Rule 71(3) Communication—Notice of Grant mailed Jul. 29, 2011.
EP 10151247.3; Decision to Grant mailed Sep. 22, 2011.
EP 10152725.7; Extended European Search Report mailed Jul. 6, 2010.
EP 10152725.7; Office Action mailed Jul. 13, 2011.
EP 10152725.7; Rule 71(3) Communication—Notice of Grant mailed Nov. 16, 2011.
EP 10152725.7; Decision to Grant mailed Apr. 13, 2012.
EP 10152725.7; Communication of a Notice of Opposition mailed Feb. 21, 2013.
EP 10152725.7; Communication of notices of opposition (R. 79(1) EPC) mailed Mar. 15, 2013.
EP 10152730.7; Extended European Search Report mailed Jun. 30, 2010.
EP 10152730.7; Office Action mailed May 10, 2011.
EP 10152730.7; Decision to Grant mailed Oct. 11, 2012.
EP 10183959.5; Extended European Search Report mailed Jun. 8, 2011.
EP 11169151.5; Extended European Search Report mailed Apr. 19, 2012.
EP 11169151.5; Office Action mailed Feb. 15, 2013.
EP 1478656; 4b O 22/11; Notice of Filing of Complaint dated Feb. 7, 2011, Regional Court Dusseldorf, Life Technologies Corp/Dharmacon Inc. et al. (English Translation).
EP 1478656; 4b O 22/11; Plaintiff's Complaint dated Feb. 7, 2011, Regional Court Dusseldorf, Life Technologies Corp/Dharmacon Inc. et al. (English Translation).
EP 1478656; 4b O 22/11; Fisher Scientific GmbH's Brief in Response to Dharmacon's Complaint dated Feb. 7, 2011, Regional Court Dusseldorf, Life Technologies Corp/Dharmacon Inc. et al. Mar. 5, 2012 (English Translation).
EP 1478656; 4b O 22/11; Defendant's Reply to Plaintiff's Complaint, Regional Court Dusseldorf, Life Technologies Corp/Dharmacon Inc. et al. Mar. 5, 2012 (English Translation).
EP 1478656; 4b O 22/11; Plaintiff's Response to Defendant's Reply to Plaintiff's Complaint Opinion, Regional Court Dusseldorf, Life Technologies Corp/Dharmacon Inc. et al. Jul. 31, 2012 (English Translation).
EP 1478656; Grounds for the Objection—Defendant's Response to Nullity Complaint with Attachments; DE 603 29 277.1-08 (EP 1 478 656 B1) filed by Fisher Scientific GmbH, plaintiff; Life Technologies Corporation, proprietor. Apr. 5, 2012 (English Translation).
EP 1478656; Nullity Complaint against DE 603 29 277.1-08 (EP 1 478 656 B1) filed by Fisher Scientific GmbH, plaintiff; Life Technologies Corporation, proprietor. English Translation of portions thereof. May 24, 2011 (English Translation).

EP 1478656; Opinion/Brief Issued by Federal Patent Court in Nullity Complaint; DE 603 29 277.1-08 (EP 1 478 656 B1) filed by Fisher Scientific GmbH, plaintiff; Life Technologies Corporation, proprietor. Jun. 22, 2012 (English Translation).

EP 1478656; Plaintiff's Reply to Defendant's Grounds of the Objection; DE 603 29 277.1-08 (EP 1 478 656 B1) filed by Fisher Scientific GmbH, plaintiff; Life Technologies Corporation, proprietor. Jul. 27, 2012 (English Translation).

EP 1478656; Defendant's Observations in Response to Board's Preliminary Opinion with Attachments (New Main Request, Klimkait Opinion & CV); DE 603 29 277.1-08 (EP 1 478 656 B1) filed by Fisher Scientific GmbH, plaintiff; Life Technologies Corporation, proprietor. Sep. 27, 2012 (English Translation).

EP 1478656; Plaintiff's Response to Defendant's Observations of the Board's Preliminary Opinion with Attachment (Leake Declaration); DE 603 29 277.1-08 (EP 1 478 656 B1) filed by Fisher Scientific GmbH, plaintiff; Life Technologies Corporation, proprietor. Nov. 8, 2012 (English Translation).

EP2128248; Notice of Opposition filed by Thermo Fisher Scientific Inc. on Feb. 2, 2012.

EP2128248; Response to Notice of Opposition filed by Life Technologies Corporation on Sep. 19, 2012.

EP2221377 Notice of Opposition filed by Thermo Fisher Scientific Inc. on Jul. 25, 2012.

JP 2003-564221; Notice of Reasons for Rejection mailed Jan. 6, 2009.

JP 2003-564221; Notice of Reasons for Rejection mailed Nov. 18, 2009.

JP 2003-564221; Notice of Decision to Grant mailed May 11, 2010.

JP 2003-564222; Office Action mailed Dec. 9, 2009.

JP 2003-564222; Office Action mailed May 25, 2010.

JP 2003-564222; Office Action mailed Mar. 29, 2011.

PCT/US03/03023; International Search Report mailed Jul. 18, 2005.

PCT/U503/03208; International Search Report mailed Feb. 13, 2004.

PCT/U503/03208; International Preliminary Examination Report mailed Apr. 26, 2004.

PCT/U503/03223; International Search Report mailed May 3, 2004.

PCT/U503/03223; International Preliminary Report on Patentability mailed Aug. 4, 2004.

PCT/U503/18626; International Search Report mailed Feb. 11, 2004.

PCT/U503/18626; Written Opinion mailed Sep. 23, 2004.

PCT/U503/18627; International Search Report mailed Mar. 16, 2004.

PCT/U503/18627; Written Opinion mailed Oct. 1, 2004.

PCT/U503/36401; International Search Report mailed May 28, 2004.

PCT/US05/46779; International Search Report with Written Opinion mailed Nov. 30, 2006.

Kits for Labeling DNA, BioDirectory'98, Amersham Pharmacia Biotech, p. 136, 1998.

OligofectAMINE Reagent product information, Cat. No. 12252-01 Invitrogen Life Reagent, Reviewed Aug. 23, 2001.

Akashi, M. et al., "Number and location of AUUUA motifs: role in regulating transiently expressed RNAs," *Blood*, vol. 83, No. 11, 1994, 3182-3187.

Alahari, S. K. et al., "Inhibition of Expression of the Multidrug Resistance-Associated P-Glycoprotein of by Phosphorothioate and 5' Cholesterol-Conjugated Phosphorothioate Antisense Oligonucleotides," *Mol. Pharmacol.*, 50(4):808-819, 1996.

Allerson, C. et al., "Fully 2'-Modified Oligonucleotide Duplexes with Improved in Vitro Potency and Stability Compared to Unmodified Small Interfering RNA," *J. Med. Chem.*, 48, 2005, 901-904.

Allinquant, B. et al., "Downregulation of Amyloid Precursor Protein Inhibits Neurite Outgrowth in Vitro," *The Journal of Cell Biology*, vol. 128, No. 5, 1995, pp. 919-927.

Altmann, K H. et al., "Novel Chemistry," *Applied Antisense Oligonucleotide Technology*, 1998, 73-107.

Altschul, S. et al., "Basic local alignment search tool," *J. Mol. Biol.*, vol. 215, 1990, 403-410.

Altschul, S. et al., "Gapped BLAST and PSI-Blast: a new generation of protein database search," *Nucleic Acids Research*, vol. 25, 1997, 3389-3402.

Amann et al., "Modern Methods in Subsurface Microbiology: In Situ Identification of Microorganisms with Nucleic Acid Probes," *FEMS Microbiology Review*, vol. 20, Issue 3-4, Jul. 1997, 191-200.

Amarasinghe et al., "*Escherichia coli* ribonuclease III: Affinity purification of hexahistidine-tagged enzyme and assays for substrate binding and cleavage," *Methods in Enzymology*, vol. 342, 2001, 143-158.

Amarzguioui et al., "Tolerance for Mutations and Chemical Modification in a siRNA," *Nucleic Acids Research*, 31(2):589-595, 2003.

Ambion Inc., "Products for RNA Structure/Function Analysis," *Ambion TechNotes*, 8(5):1-3, Nov. 2001.

Ambion Inc., "Design and testing of siRNAs," *Ambion TechNotes*, 9(1):4, Feb. 2002.

Ambion Inc., "siRNA Tools for Every Lab, "*Ambion TechNotes*, 9(3):1-19, Jun. 2002.

Ambion, Inc., "pSilencer siRNA Expression Vector, "*Ambion TechNotes*, a newsletter from 9(4), 2002.

Ambion Inc., "High sensitivity qRT-PCR—MessageSensorTM reverse transcription kit for one step qRT-PCR," *Ambion TechNotes Newsletter*, 10(1):1-19 (entire newsletter), 2003.

Ambion Inc., "Enhanced siRNA Delivery and Long-Term Gene Silencing," *Ambion TechNotes Newsletter*, 12(1):22-25, 2003.

Ambion Inc., "The Best Controls for siRNA Experiments—Now Available with More Choices," *Ambion TechNotes Newsletter*, 12(1):22-25, 2003.

Anderson et al., "Human Gene Therapy," *Nature*, vol. 392, Supplement, Apr. 30, 1998, 25-30.

Aoki, Y. et al., "RNA Interference May be more Potent Than Antisense RNA in Human Cancer Cell Lines," *Clinical and Experimental Pharmacology Physiology*, vol. 30, 2003, pp. 96-102.

Ashley et al., "Chemical Synthesis of Oligodeoxynucleotide Dumbbells," *Biochemistry*, 30, 1991, 2927-2933.

ATTC, Catalogue of Cell Lines & Hybridomas, 7th Edition, 1992, 15 pages.

Augustyns, K. et al., "Incorporation of Hexose Nucleoside Analogues into Oligonucleotides: Synthesis, Base-Pairing Properties of Enzymatic Stability," *Nucleic Acids Research*, vol. 20, No. 18, 1992, 4711-4716.

Aurup, H. et al., "Translational of 2'-Modified mRNA in vitro and in vivo," *Nucleic Acids Research*, vol. 22, No. 23, 1994, pp. 4963-4968.

Ausubel et al., *Current Protocols in Molecular Biology*, Supplement 63, (Table of Contents), 1998.

Ausubel et al., "Introduction to Expression by Fusion Protein Vectors," *Current Protocols in Molecular Biology*, 1994, 16.4.1-16.4.4.

Ausubel et al., "Short Protocols in Molecular Biology," *A Compendium of Methods from Current Protocols in Molecular Biology*, 2002, 359.

Baglioni et al., "Mechanisms of antiviral action of interferon," *Interferon*, 5:23-42, 1983.

Bartzatt, R., "Cotransfection of Nucleic Acids Segments by Sendai Virus Envelopes," *Biotechnology and Applied Biochemistry*, vol. 11, 1989, 133-135.

Bass, B., "Double-Stranded RNA as a Template for Gene Silencing," *Cell*, vol. 101, 2000, 235-238.

Beaucage et al. "Advances in the Synthesis of Oligonucleotides by the Phosphoramidite Approach," *Tetrahedron*, 48:2223-2311, 1992.

Bennett et al., "Antisense oligonucleotides as a tool for gene functionalization and target validation," *Biochimica et Biophysica Acta*, vol. 1489: 19-30; 1999.

Bennett, C. F. et al., "Cationic lipids enhance cellular uptake and activity of phosphorothioate antisense oligonucleotides," *Molecular Pharmacology*, vol. 41, 1992, 1023-1033.

Bergan et al., "Electroporation enhances c-myc antisense oligodeoxynucleotide efficacy," *Nucleic Acids Research*, 21, 1993, 3567-3573.

Bergot, J. et al., "Separation of synthetic phosphorothioate oligonucleotides from their oxygenated (phosphodiester) defect species by strong-anion-exchange high-performance liquid chromatography.," *J Chrom.*, 599, 1992, 35-42.

Bergstrom et al., "Comparison of the base pairing properties of a series of nitroazole nucleobase analogs in the oligodeoxyribonucleiotide sequence 5'-d(CGCXAATTYGCG)-3'," *Nucleic Acids Res.* 25(10):1935-1942, 1997.

Bernstein et al., "Role for a bidentate ribonuclease in the initiation step of RNA interference," *Nature*, 409: 363-366—Supplement 1-8, 2001.
Bernstein et al., "The Rest is Silence," *RNA*, vol. 7, Cambridge University Press 2001, 1509-1521.
Bevilacqua et al., "Minor-Groove Recognition of Double-Stranded RNA by the Double-Stranded RNA-Binding Domain from the RNA-Activated Protein Kinase PKR,"*Biochemistry*, vol. 35, Issue 31, Aug. 6, 1996, 9983-9994.
Bjergarde, Kristen et al., "Solid phase synthesis of oligodeoxyribonucleoside phosphorodithioates from thiophosphoramidites," *Nucleic Acids Research*, vol. 19, 1991, 5843-5850.
Black et al. "Studies on the toxicity and antiviral activity of various polynucleotides," *Antimicrob. Agents Chemotherap.*, 3(2):198-206, 1972.
Blake et al, "Hybridization Arrest of Globin Synthesis in Rabbit Reticulocyte Lysates and Cells by Oligodeoxyribonucleoside Methylophosphonates," *Biochemstry*, vol. 24, No. 22, Oct. 1985, 6139-6145.
Blaszczyk et al., "Crystallographic and modeling studies of RNase III suggest a mechanism for double-stranded RNA cleavage," *Structure*, 9(12):1225-1236, 2001.
Bosher et al., "RNA interference: genetic wand and genetic watchdog," *Nat. Cell. Biol.*, 2:E31-E36, 2000.
Bouloy et al., "Both the 7-Methyl and the 2'-O-Methyl Groups in the Cap of mRNA Strongly Influence Its Ability to Act as Primer for Influenza Virus RNA Transcription," *Proceedings of the National Academy of Sciences (PNAS)*, vol. 77, Issue 7, Jul. 15, 1980, 3951-3956.
Boutorin et al., "Synthesis of alkylating oligonucleotide derivatives containing cholesterol or phenazinium residues at their 3'-terminus and their interaction with DNA within mammalian cells," *FEBS Letters*, vol. 254, 1989, 129-132.
Boutorine et al., "Reversible Covalent Attachment Of Cholesterol To Oligodeoxyribonucleotides For Studies Of The Mechanisms Of Their Penetration Into Eucaryotic Cells," *Biochimie*, vol. 75, 1993; 35-41.
Branch, A., "A good antisense molecule is hard to find," *TIBS*, vol. 23: 45-50, 1998.
Britten et al., "Nucleic Acid Hybridisation: A Practical Approach," Oxford University Press, 1985, 5-7.
Brown et al., "Sequence-Specific Endonucleolytic Cleavage and Protection of mRNA in Xenopus and Drosophila," *Genes & Development*, vol. 7, No. 8, Aug. 1993, 1620-1631.
Brummelkamp et al., "A system for stable expression of short interfering RNAs in mammalian cells," *Science*, 296(5567):550-553, 2002.
Bull et al., "Viral escape from antisense RNA," *Molecular Microbiology*, 28(4):835-846, 1998.
Bunnell, B. A. et al., "Targeted Delivery of Antisense Oligonucleotides by Molecular Conjugates," *Somatic Cell and Molecular Genetics*, vol. 18, No. 6, 1992, 559-569.
Byrom et al., "Inducing RNAi with siRNA cocktails generated by RNAse III," Ambion TechNotes Newsletter, 10(1):4-6, 2003.
Caplen et al., "Specific inhibition of gene expression by small double-stranded RNAs in invertebrate and vertebrate systems," *Proc. Natl. Acad. Sci. USA*, 98(17):9742-9747, 2001.
Caruthers, M. H. et al., "Chemical and Biochemical Studies with Dithioate DNA," *Nucleosides & Nucleotides*, 10(1-3), 1991, 47-59.
Catalanotto et al., "Transcription: gene silencing in worms and fungi," *Nature*, 404(6775):245, 2000.
Chen, G. et al., "Antisense oligonucleotides demonstrate a dominant role of c-Ki-RAS proteins in regulating the proliferation of diploid human fibroblasts," *The Journal of Biological Chemistry*, vol. 271, No. 45, 1996, 28259-28265.
Chen et al, "Characterization of a Bicistronic Retroviral Vector Composed of the Swine Vesicular Disease Virus Internal Ribosome Entry Site," *Journal of Virology*, vol. 67, Issue 4, Apr. 1993, 2142-2148.
Chen, C. et al, "High-Efficiency Transformation of Mammalian Cells by Plasmid DNA," *Mol Cell Biol.*, 7(8), 1987, 2745-2752.

Chiang, M. Y. et al., "Antisense Oligonucleotides Inhibit Intercellular Adhesion Molecule 1 Expression by Two Distinct Mechanisms," *J. Biol. Chem.*, vol. 266, No. 27, 1991, 18162-18171.
Chidambaram, N. et al., "Targeting of Antisense: Synthesis of Steroid-Linked and Steroid-Bridged Oligodeoxynucleotides," *Drug Discovery*, 3(1):237-33, 1989.
Chiu et al., "RNAi in Human Cells: Basic Structural and Functional Features of Small Interfering RNA," *Molecular Cell*, vol. 10, pp. 549-561, Sep. 2002.
Chiu et al., "siRNA Function in RNAi: A Chemical Modification Analysis," *RNA*, 9:1034-1048, 2003.
Chu et al., "The Stability of Different Forms of Double-Stranded Decoy DNA in Serum and Nuclear Extracts," *Nucleic Acids Research*, 20, 1992,5857-5858.
Cioca, D. P. et al., "RNA interference is a functional pathway with therapeutic potential in human myeloid leukemia cell lines," *Cancer Gene Therapy*, vol. 10, 2003, 125-133.
Clusel; C. et al., "Ex vivo regulation of specific gene expression by namomolar concentration of double stranded dumbbell oligonucleotides," *Nucleic Acids Research*, vol. 21, No. 15, Oxford University Press 1993; pp. 3405-213.
Cogoni et al., "Gene silencing in Neurospora crassa requires a protein homologous to RNA-dependent RNA polymerase," *Nature*, 399:166-169, 1999.
Cogoni et al., "Posttranscriptional gene silencing in Neurospora by a RecQ DNA helicase," *Science*, 286:2342-2344, 1999.
Cook,P., "Medicinal Chemistry Of Antisense Oligonucleotides," *Antisense Drug Technology*, vol. 2, 2001; pp. 29-56.
Cormack et al., "Cloning of PCR products using the green floorscent protein," United States National Library of Medicine, Accession No. AF007834; 1997.
Cottrell, T. et al., "Silence of the strands: RNA interference in eukaryotic pathogens," *Trends Microbiol.*, vol. 11, No. 1, 2003, 37-43.
Cummins et al., "Characterization of fully 2'—Modified Oligoribonucleotide Hetero- and Homoduplex Hybridization and Nuclease Sensitivity," *Nucleic Acids Research*, 23(11):2019-2024, 1995.
Czauderna et al., "Structural Variations and Stabilising Modifications of Synthetic siRNAs in Mammalian Cells," *Nucleic Acids Research*, 31(11):2705-2716, 2003.
Dalmay et al., "An RNA-dependent RNA polymerase gene in Arabidopsis is required for posttranscriptional gene silencing mediated by a transgene but not by a virus," *Cell*, 101:543-553, 2000.
Dalmay et al., "SDE3 encodes an RNA helicase required for post-transcriptional gene silencing in Arabidopsis," *Embo J.*, 20(8):2069-2078, 2001.
De Clercq et al. "Interferon Induction by two 2' modified bouble helical RNA ploy 2' Fluro-2'-deoxy inosinic-acid poly cytidylic-acid and poly-2' chloro-2'-deoxy inosinic-acid poly cytidylic-acid," *European Journal of Biochemistry*, vol. 107, No. 1: 279-288; 1980.
Dean, N. M. et al., "Identification and Characterization of Second-Generation Antisense Oligonucleotides," *Antisense & Nucleic Acid Drug Development*, vol. 7, 1997, 229-233.
Derossi, D. et al., "Trojan peptides: the penetratin system for intracellular delivery," *Trends in Cell Biolog.*, 8, 1998, 84-87.
Devereux et al., "A comprehensive set of sequence analysis programs for the VAC," *Nucleic Acid. Res.*, 12(1):387-395, 1984.
Dewanjee et al., "Kinetics of Hybridization of mRNA of c-myc Oncogene with 111 In Labeled Antisense Oligodeoxynucleotide Probes by High-Pressure Liquid Chromatography," *Biotechniques*, 16(5):844-850, 1994.
Dias et al., "Antisense Oligonucleotides: Basic Concepts and Mechanisms," *Molecular Cancer Therapeutics*, vol. 1:347-355, Mar. 2002.
Diaz et al., "Initiation of plasmid R1 replication in vitro is independent of transcription of host RAN polymerase," *Nucleic Acids Research*, 12(13):5175-5191, 1984.
Diaz et al., "Hierarchy of base-pair preference in the binding domain of the bacteriophage T7 promoter," *J. Mol. Biol.*, 229:805-811, 1993.
Didenko, V. "DNA probes using fluorescence resonance energy transfer (FRET): designs and applications," *Biotechniques*, 31(5):1106-1121, 2001.

Donzé et al., "RNA interference in mammalian cells using siRNAs synthesized with T7 RNA polymerase," *Nucleic Acids Research*, 30(10):e46:1-4, 2002.

Downward, "RNA Interference," *BMJ*, vol. 328, pp. 1245-1248, May 22, 2004.

Dubins et al., "On the stability of double stranded nucleic acids," *J. Am. Chem. Soc.*, 123:9254-9259, 2001.

Eckstein et al., "Exogenous Application of Ribozymes for Inhibiting Gene Expression," *CIBA Foundation Symposium*, vol. 209, 1997, 207-217.

Elbashir et al., "Analysis of gene function in somatic mammalian cells using small interfering RNAs," *Methods*, 26:199-213, 2002.

Elbashir et al., "Duplexes of 21-nucleotide RNAs mediate RNA interference in cultured mammalian cells," *Nature*, 411:494-498, 2001.

Elbashir et al., "Functional anatomy of siRNAs for mediating efficient RNAi in Drosphila melanogaster embryo lysate," *Embo J*, 20(23):6877-6888, 2001.

Elbashir et al., "RNA interference is mediated by 21-and 22-nucleotide RNAs," *Genes & Development*, 15:188-200, 2001.

Elliott, G. et al., "Intercellular trafficking and protein delivery by a herpesvirus structural protein," *Cell*, vol. 88,1997, 223-233.

Emptage et al., "Calcium Stores in Hippocampal Synaptic Boutons Mediate Short-Term Plasticity, Store-Operated Ca2+ Entry, and Spontaneous Transmitter Release" *Neuron*, 29(1):197-208, 2001.

Escude, C. et al., "Rational design of a triple helix-specific intercalating ligand," *Proc. Natl. Acad. Sci.*, vol. 95, 1998, 3591-3596.

Escude, C. et al., "Stable triple helices formed by oligonucleotide N3' -> P5' phosphoramidates inhibit transcription elongation," Proc. Natl. Acad. Sci., vol. 93, 1996, 4365-4369.

Fechheimer et al. "Transfection of mammalian cells with plasmid DNA by scrape loading and sonication loading," *Proc. Natl. Acad. Sci. USA*, vol. 84, 1987, 8463-8467.

Fire et al., "Potent and specific genetic interference by double-stranded RNA in Caenorhabditis elegans," *Nature*, 391:806-811, 1998.

Fisher, T. et al., "Intracellular disposition and metabolism of fluorescently-labeled unmodified and modified oligonucleotides microinjected into mammalian cells," *Nucleic Acids Research*, vol. 21, No. 16, 1993, 3857-3865.

Flanagan, W. M. et al., "A cytosine analog that confers enhanced potency to antisense oligonucleotides," *Proc. Natl. Acad. Sci.*, vol. 96, 1999, 3513-3518.

Ford et al., "RNAi and Microarrays Reveal Biological Pathways: The combination of RNAi with microarrays has enormous potential for elucidating biological pathways. However, before this potential can be fulfilled, important questions need to be answered to ensure the proper interpretation of gene silencing results," *R&D Magazine*, Jul., 2003. pp. 48 (3 pages).

Fraley et al., "Entrapment of a bacterial plasmid in phospholipid vesicles: potential for gene transfer," *Proc. Natl. Acad. Sci. USA*, vol. 76, 1979, 3348-3352.

Freier, S., et al., "The ups and downs of nucleic acid duplex stability: structure-stability studies on chemically-modified DNA:RNA duplexes," *Nucleic Acids Research*, vol. 25, No. 22, 1997; pp. 4429-4443.

Froehler et al. "Synthesis of DNA via deoxynucleoside H-phosphonate intermediates," *Nucleic Acids Res.*, 14(13):5399-5407, 1986.

Froham, Michael, "RACE: Rapid amplification of cDNA ends," *PCR protocols: A guide to methods and applications* (eds. M.A. Innis, D.H. Gelfand, J.J. Sninsky, and T.J. White), pp. 28-38, 1990 Academic Press, Inc.

Fuerst et al., "Use of hybrid vaccinia virus-T7 RNA polymerase system for expression of target genes," *Molecular and Cellular Biology*, 7(7):2538-2544, 1987.

Gagnor, C. et al., "α-DNA VI: comparative study of α- and β-anomeric oligodeoxyribonucleotides in hybridization to mRNA and in cell free translation inhibition," *Nucleic Acids Research*, vol. 15, No. 24, 1987, 10419-10436.

Gillam et al., "Enzymatic synthesis of oligodeoxyribonucleotides of defined sequence," *J. Biol. Chem.*, vol. 253, 1978, 2532-2539.

Gillam et al., "Defined transversion mutations at a specific position in DNA using synthetic oligodeoxyribonucleotides as mutagens," *Nucleic Acids Resarch*, 6(9):2973-2985, 1979.

Ginobbi, P., "Folic acid-polylysine carrier improves efficacy of c-myc antisense oligodeoxynucleotides on human melanoma (M14) cells," *Anticancer Research*, vol. 17, 1997, 29-35.

Giovannangeli et al., "Oligonucleotide clamps arrest DNA synthesis on a single-stranded DNA target," *Proc. Nat. Acad. Sci. USA*, vol. 90, 1993, 10013-10017.

Gitlin et al., "Short interfering RNA confers intracellular antiviral immunity in human cells," *Nature*, vol. 418, 2002, 430-434.

Gopal, T.V. "Gene transfer method for transient gene expression, stable transformation, and cotransformation of suspension cell cultures," *Mol. Cell. Biol.*, vol. 5, 1985, 1188-1190.

Gorman, Cornelia M., "High Efficiency Gene Transfer into Mammalian Cells," *DNA Cloning*, vol. II, Jul. 1985; pp. 143-190.

Gorman et al., "Recombinant Genomes Which Express Chloramphenicol Acetyltrasferase in Mammalian Cells," *Molecular and Cellular Biology*, Sep. 1982; pp. 1044-1051.

Gould, S. J. et al., "Firefly luciferase as a tool in molecular and cell biology," *Analytical Biochemistry*, vol. 175, 1988, 5-13.

Griffey et al., "Characterization of Oligonucleotide Metabolism In Vivo via Liquid Chromatography/Electrospray Tandem Mass Spectrometry with a Quadrupole Ion Trap Mass Spectrometer," *J. Mass. Spectrom.*, vol. 32(3), 305-313, 1997.

Grishok et al., "Genes and mechanisms related to RNA interference regulate expression of the small temporal RNAs that control C. elegans developmental timing," *Cell*, 106:23-34, 2001.

Grishok et al., "Genetic Requirements for Inheritance of RNAi in C. elegans," *Science*, vol. 287:2494-2497, Mar. 31, 2000.

Grotjahn et al., "Ultrafast sequencing of oligodeoxyribonucleotides by FAR-mass spectrometry," *Nucleic Acids Research*, vol. 10, 1982; pp. 4671-4678.

Grotli, M et al., "2'-0-Propargyl Oligoribonucleotides: Synthesis and Hybridisation," *Tetrahedron*, vol. 54, No. 22, 1998, 5899-5914.

Gutierrez, A J. et al., "Antisense Gene Inhibition by C-5-Substituted Deoxyuridine-Containing Oligodeoxynucleotides," *Biochemistry*, vol. 36, 1997, 743-748.

Grünweller et al., "Comparison of Different Antisense Strategies in Mammalian Cells Using Locked Nucleic Acids, 2'-0-methyl RNA, Phosphorothioates and small interfering RNA," *Nucleic Acids Research*, 31(12):3185-3193, 2003.

Hames, B. D. et al., "Nucleic acid hybridisation: a practical approach," Oxford University Press 1985, 5-7 (Britten).

Hamilton et al., "A species of small antisense RNA in post-transcriptional gene silencing in plants," *Science*, 286:950-952, 1999.

Hammond et al., "An RNA-directed nuclease mediates post-transcriptional gene silencing in Drosophila cells," *Nature*, 404(6775):293-296, 2000.

Hammond et al., "Argonaute2, a link between genetic and biochemical analyses of RNAi," *Science*, 293:1146-1150, 2001.

Hammond et al., "Post-transcriptional gene silencing by double-stranded RNA," *Nat. Rev. Genet.*, 2(2):110-119, 2001.

Hammond, "RNAi Technologies in Drosophila Cell Culture," *RNAi—A Guide to Gene Silencing*, (Cold Spring Harbor Laboratory Press, Hannon, Ed.) Chapter 16, pp. 345-360, 2003.

Han et al., "Sequence-specific recognition of double helical RNA and RNA-DNA by triple helix formation," *Proc. Natl. Acad. Sci.*, USA, 90:3806-3810, 1993.

Hannon et al., "Unlocking the Potential of the Human Genome with RNA Interference,"*Nature* 431:371-378, 2004.

Harborth et al., "Identification of Essential Genes in Cultured Mammalian Cells Using Small Interfering RNAs," *Journal of Cell Science*, 114(24):4557-4565, 2001.

Harland at el., "Translation of mRNA injected into Xenopus oocytes is specifically inhibited by antisense RNA," *J. Cell. Biol.*, 101:1094-1099, 1985.

Hebert et al., "Purification of ribonucleases Sa, Sa2, and Sa3 after expression in *Escherichia coli*," *Protein Expr. Purif.*, 11(2):162-168, 1997.

Helene, C. et al., "Control of gene expression by oligonucleotides covalently linked to intercalating agents," Genome, vol. 31,1989, 413-421.

Higgins et al., "CLUSTAL V: improved software for multiple sequence alignment," Computer Applications in the Biosciences (CABIOS), 8(2):189-191, 1992.

Ho et al., "Preparation of microemulsions using polyglycerol fatty acid esters as surfactant for the delivery of protein drugs," J. Pharm. Sci., 85 1996, 138-143.

Hoke, G. D. et al., "Effects of phosphorothioate capping on antisense oligonucleotide stability, hybridization and antiviral efficacy versus herpes simplex virus infection," Nucleic Acids Research, vol. 19, No. 20, 1991, 5743-5748.

Holen et al., "Positional Effects of Short Interfering RNAs targeting the Human Coagulation Trigger Tissue Factor," Nucleic Acids Research, 30(8):1757-1766, 2002.

Holen et al., "Similar behaviour of single-strand and double-strand siRNAs suggests they act through a common RNAi pathway," Nucleic Acids Research, 31(9):2401-2407, 2003.

Hough et al., "Why RNAi Makes Sense," Nature Biotechnology, vol. 21(7):731-732, Jul. 2003.

Hutvagner et al., "A cellular function for the RNA-interference enzyme Dicer in the maturation of the let-7 small temporal RNA," Science, 293:834-838, 2001.

Innis et al., "DNA sequencing with Thermus aquaticus DNA polymerase and direct sequencing of polymerase chain reaction-amplified DNA," Proc. Natl. Acad. Sci. USA, vol. 85, 1988, 9436-9440.

Invitrogen, "Life Technologies Inc. Catalogue and Reference Guide—LIPOFECTAMINE Reagent, LIPOFECTIN Reagent," GIBCO-BRL 1993-1994, pp. 9-19.

Ishihara, K. et al., "Effects of phospholipid Adsorption on nonthrombogenicity of Polymer with phospholipid polar group," Journal of Biomedical Materials Research, vol. 27, 1993, 1309-1314.

Itakura et al., "Chemical DNA synthesis and recombinant DNA studies," Science, vol. 209, 1980, 1401-1405.

Itakura et al.,"Chemical synthesis and sequence studies of deoxyribooligonucleotides which constitute the duplex sequence of the lactose operator of Escherichia coli," J. Biol. Chem., 250:4592 1975.

Iyer et al., "3H-1,2-benzodithiole-3-one 1,1-dioxide as an improved sulfurizing reagent in the solid-phase synthesis of oligodeoxyribonucleoside phosphorothioates," J. Am. Chem. Soc., 112:1253-1254, 1990.

Jackson et al., "Expression Profiling Reveals Off-Target Gene Regulation by RNAi," Nature Biotechnology, 21(6):635-638, Jun. 2003.

Jacque et al., "Modulation of HIV-1 replication by RNA interference," Nature, 418:435-438, 2002.

Jarvis, T. C. et al., "Optimizing the Cell Efficacy of Synthetic Ribozymes," J. Biol. Chem., vol. 271, No. 46, 1996, 29107-29112.

Ji et al., "Enhanced gene silencing by the application of multiple specific small interfering RNAs," FEBS Letters, 552:247-252, 2003.

Johnson et al., "Peptide Turn Mimetics," Biotechnology and Pharmacy (eds. Pezzuto et al.), pp. 367-378, 1993 Chapman & Hall, Inc.

Kamata, H. et al., "Amphiphilic peptides enhance the efficiency of liposome-mediated DNA transfection," Nucleic Acids Research, vol. 22, No. 3, 1994, 536-537.

Kaneda et al., "Increased Expression of DNA Cointroduced with Nuclear Protein in Adult Rat Liver," Science, vol. 243, 1989, 375-378.

Kato, et al, "Expression of Hepatitis B Virus Surface Antigen in Adult Rat Liver," J. Biol. Chem., vol. 266, 1991, 3361-3364.

Kawasaki, H. et al., "Short hairpin type of dsRNAs that are controlled by tRNA(Val) promoter significantly induce RNAi-mediated gene silencing in the cytoplasm of human cells," Nucleic Acids Research, vol. 31, No. 2, 2003, 700-707.

Kawasaki et al., "Uniformly modified 2'-deoxy-2'-fluoro-phosphorothioate oligonucleotides as nuclease-resistant antisense compounds with high affinity and specificity for RNA targets," Journal of Medicinal Chemistry, American Chemical Society, vol. 36, No. 7: 831-841, 1993.

Kawase et al., "Studies on nucleic acid interactions I. Stabilities of mini-duplexes (dG2A4XA4G2-dC2T4YT4C2) and self-complementary d(GGAAXYTTCCC) containing deoxyinosine and other mismatched bases," Nucleic Acids Res., 14(19):7727-7736, 1986.

Kennerdell et al., "Heritable Gene Silencing in Drosophila using Double-Stranded RNA," Nature Biotechnology, 17:896-898, 2000.

Ketting et al., "A genetic link between co-suppression and RNA interference in C. elegans," Nature, 404(6775):296-298, 2000.

Ketting et al., "mut-7 of C. elegans, required for transposon silencing and RNA interference, is a homolog of Werner syndrome helicase and RNaseD," Cell, 99:133-141, 1999.

Ketting et al., "Dicer Functions in RNA Interference and in Synthesis of Small RNA Involved in Developmental Timing in C. Elegans," Genes Dev., vol. 15: 2654-2659, 2001.

Kharrat et al., "Structure of the dsRNA binding domain of E. coli RNase III," The Embo. J., 14(14):3572-3584, 1995.

Khorana, "Total synthesis of a gene," Science, vol. 203, 614, 1979.

Kievits et al., "NASBAtm isothermal enzymatic in vitro nucleic acid amplification optimized for the diagnosis of HIV-1 infection," Journal of Virological Methods, 35:273-286, 1991.

Kimura et al., "Alterations of c-myc expression by antisense oligodeoxynucleotides enhance the induction of apoptosis in HL-60 cells," Cancer Research, 55:1379-1384, 1995.

Kita et al., "Modulation of polyglutamine-induced cell death by genes identified by expression profiling," Human Molecular Genetics, 11(19):2279-2287, 2002.

Klostermeier and Millar, "Time-resolved fluorescence resonance energy transfer: a versatile tool for the analysis of nucleic acids," Biopolymers, 61(3):159-79, 2001-2002.

Knight et al., "A Role for the RNase III Enzyme DCR-1 in RNA Interference and Germ Line Development in C. elegans," Science, 293(5538):2269-2271, 2001.

Kuhnast et al., "General method to label antisense oligonucleotides with radioactive halogens for pharmacological and imaging studies," Bioconjug. Chem., 11(5):627-636, 2000.

Kukreti et al., "Extension of the range of DNA sequences available for triple helix formation: stabilization of mismatched triplexes by acridine-containing oligonucleotides," Nucleic Acids Research, vol. 25, No. 21, 1997, pp. 4264-4270.

Kurreck, "Antisense Technologies: Improvement Through Novel Chemical Modifications," Eur. J. Biochem, 270:1628-1644, 2003.

Kuwasaki et al., "Hairpin Antisense Olignucleotides Containing 2'—Methoxynucleosides with Base-Pairing in the Stem Region at the 3'—end Penetration, Localization, and Anti-HIV Activity," Biochemical Biophysical Res. Comm., 228:623-631, 1996.

Kuznicki et al., "Combinatorial RNA Interference Indicates GLH-4 Can Compensate for GLH-1; these two P Granule Components are Critical for Fertility in C. elegans," Development, 127:2907-2916, 2000.

Kwoh et al., "Transcription-based amplification system and detection of amplified human immunodeficiency virus type 1 with a bead-based sandwich hybridization format," Proc. Natl. Acad. Sci. USA, 86:1173-1177, 1989.

Lacoste, J. et al., "Triple helix formation with purine-rich phosphorothioate-containing oligonucleotides covalently linked to an acridine derivative," Nucleic Acids Research, vol. 25, No. 10, 1997, 1991-1998.

Lamond, A. I., "2'-O-Alkyloligoribonucleotides: Probes for Studying the Biochemistry and Cell Biology of RNA Processing," Biochemical Society Transactions, vol. 21, 1993, pp. 1-8.

Laplanche, et al., "Phosphorotiate-modified oligodeoxyribonucleotides. III. NRM and UV spectroscopic studies of the Rp-Rp, Sp-Sp, and Rp-Sp duplexes, [d(GG2AATTCC)2, derived from diastereomeric O-ethyl phosphorothioates," Nucleic Acids Research, vol. 14, No. 22, 1986, 9081-9093.

Latham et al., "Six Methods of inducing RNAI in Mammalian Cells," RNA Interference Technology, (Cambridge, Appasani, ed.,) pp. 147-160, 2005.

Lavigne at al., "Lipid-Based Delivery of Combinations of Antisense Oligodeoxynucleotides for the In Vitro Inhibition of HIV-1 Replication," AAPS Pharmsci, 3(1): 1-12, 2001.

Lee et al., "Expression of small interfering RNAs targeted against HIV-1 rev transcripts in human cells," *Nat. Biotechnol.*, 19:500-505, 2002.

Lee et al., "Tissue-specific promoter usage in the D1A dopamine receptor gene in brain and kidney," *DNA and Cell Biol.*, 16(11):1267-1275, 1997.

Lemaitre, M. et al., "Specific antiviral activity of a poly(L-lysine)-conjugated oligodeoxyribonucleotide sequence complimentary to vesticular somatitis virus N protein mRNA initiation site," *Proceedings of the National Academy of Sciences USA*, vol. 84, 1987, 648-652.

Letsinger, R. et al., "Cholesteryl-conjugated oligonucleotides: Synthesis, properties, and activity as inhibitors of replication of human immunodeficiency virus in cell culture," *Proc. Natl. Acad. Sci.*, 86(17):6553-6556, 1989.

Lewin, B., "Copying mRNA into DNA," *Genes*, Third Edition, 1987 John Wiley & Sons, 358-359.

Lewis, J. G. et al., "A Serum-Resistant Cytofectin for Cellular Delivery of Antisense Oligodeoxynucleotides and Plasmid DNA," *Proceedings of the National Academy of Sciences*, vol. 93, 1996, 3176-3181.

Li et al., "Double-stranded RNA injection produces null phenotypes in Zebrafish," *Developmental Biology*, 217:394-405, 2000.

Liang et al., "Oligonucleotide delivery: a cellular prospective," *Pharmazie*, 1999, pp. 559-566.

Liang et al. "RNA interference targeted to multiple P2X receptor subtypes attenuates zinc-induced calcium entry" *Am. J. Physiol. Cell Physiol.*, vol. 289: C388-396, 2005.

Life Technologies Corporation, "Life in the Lab Products, Information and Scientainment for the Lab," Spring 2012 Canada, pp. 1-30.

Lin et al., "Policing rogue genes," Nature, 402:128-129, 2000.

Liu et al., "A scintillation proximity assay for rna detection," *Anal. Biochem.*, 289:239-245, 2001.

Lorenz et al., "Phosphorothioate Antisense Olignucleotides Induce the Formation of Nuclear Bodies," *Molecular Biology of the Cell*, vol. 9 1007-1023, May 1998.

Lu et al., "Delivering siRNA in vivo for Functional Genomics and Novel Therapeutics," *RNA Interference Technology*, (Cambridge, Appasani, ed.,) pp. 303-317, 2005.

Ma et al., "Intracellular mRNA cleavage induced through activation of RNase P by nuclease-resistant external guide sequences," *Nature Biotechnology*, vol. 18, 2000, 58-61.

Majlessl et al., "Advantages of 2'-O-methyl oligoribonucleotlde probes for detecting RNA targets," *Nucleic Acids Research*, vol. 26, No. 9, 1988, 2224-2229.

Makeyev et al., "Replicase activity of purified recombinant protein P2 of double-stranded RNA bacteriophage phi6," *Embo J*, 19(1):124-133, 2001.

Manche et al., "Interactions between Double-Stranded RNA Regulations and the Protein Kinase DAI," *Molecular and Cellular Biology*, 12:5238-5248, 1992.

Marchand et al., "Stabilization of triple-helical DNA by a benzopyridoquinoxaline intercalator," *Biochemistry*, vol. 35, 1996, 5022-5032.

Manoharan, "Oligonucleotide in Antisense Drug Technology," 2001, 391-469.

Manoharan et al., "Lipidic Nucleic Acids," *Tetrahedron Letters*, vol. 36(21), 1995, 3651-3654.

Manoharan, "2'-Carbohydrate Modifications in Antisense Oligonucleotide Therapy: Importance of Conformation, Configuration and Conjugation," *Biochimica et Biophysica Acta*, vol. 1489, Aug. 6, 1999, 117-130.

Martinez et al., "Single-stranded antisense siRNAs guide target RNA cleavage in RNAi," *Cell*, 110(5):563-574, 2002.

Matteucci, Mark D. et al., "In Pursuit of Antisense," *Nature*, vol. 384, Supp 1996, 20-23.

McCaffrey et al., "RNA Interference in Adult Mice," *Nature*, vol. 418:38-39, Jul. 4, 2002.

McKay, R. A. et al., "Enhanced Activity of an Antisense Oligonucleotide Targeting Murine Protein Kinase C-alpha by the Incorporation of 2'-O-Propyl Modifications," *Nucleic Acids Research*, vol. 24, No. 3, 1996, 411-417.

McManus et al., "Gene silencing in mammals by small interfering RNAs," *Nature Reviews*, Genetics, 3:737-747, 2002.

McNeal, C. J. et al., "A New Method for Sequencing Fully Protected Oligonucleotides Using 252Cf-Plasma Desorption Mass Spectrometry," *J. Am. Chem. Soc.*, vol. 104, 1982, 976-980.

Meister et al., "Mechanisms of Gene Silencing by Double-Stranded RNA," *Nature*, 431:343-349, 2004.

Milligan et al., Oligoribonucleotide synthesis using T7 RNA polymerase and synthetic DNA templates, *Nucleic Acids Res.*, 25:8783-8798, 1987.

Miyagishi et al., "U6 promoter-driven siRNAs with four uridine 3' overhangs efficiently suppress targeted gene expression in mammalian cells," *Nat. Biotechnol.*, 5:497-500, 2002.

Monia, B. et al., "Evaluation of 2'-Modified Oligonucleotides containing 2'-Deoxy Gaps as Antisense Inhibitors of Gene Expression," *The Journal of Biological Chemistry*, vol. 268, No. 19, 1993, 14514-14522.

Monia, B. et al., "Sequence-specific antitumor activity of a phosphorothioate oligodeoxyribonucleotide targeted to Human C-raf kinase supports an antisense mechanism of action in vivo," *Proceedings of the National Academy of Sciences*, vol. 93, 1996, 15481-15484.

Montgomery et al., "RNA as a target of double-stranded RNA-mediated genetic interference in *Caenorhabditis elegans*," *Proceedings of the National Academy of Sciences USA*, 95:15502-15507, 1998.

Moon et al., "Potent Growth Inhibition of Leukemic Cells by Novel Ribbon-type Antisense Oligonucleotides of c-mybl" *Journal of Biological Chemistry*, 275(7):4647-4653, 2000.

Morgan et al., "A More Efficient and Specific Strategy in the Ablation of mRNA in Xenopus laevis Mixtures of Antisense Oligos," *Nucleic Acids Research*, vol. 21, No. 19:4615-4620, 1993.

Moulds, C. et al., "Site and Mechanism of Antisense Inhibition by C-5 Propyne Oligonucleotides," *Biochemistry*, vol. 34, 1995, 5044-5053.

Mourrain et al., "Arabidopsis SGS2 and SGS3 genes are required for posttranscriptional gene silencing and natural virus resistance," *Cell*, 101:533-542, 2000.

Murphy et al., "A combinatorial approach to the discovery of efficient cationic peptoid reagents for gene delivery," *Proceedings of the National Academy of Sciences USA*, vol. 95, 1998, 1517-1522.

Myers et al. "Recombinant Dicer efficiently converts large dsRNAs into siRNAs suitable for gene silencing," *Nature Biotechnology*, 21: 324-328, 2003.

Myers et al., "Optimal Alignments in Linear Space," *Cabios*, vol. 4, 1989, 11-17.

Natarajan et al., "Cis and Trans Activation of Adenovirus Iva2 Gene Transcription," *Nucleic Acids Research*, vol. 13, No. 11, 1985, 4067-4083.

Ngô et al., "Double-stranded RNA induces mRNA degradation in *Trypanosoma brucei*," *Proceedings of the National Academy of Sciences USA*, 95:14687-14692, 1998.

Nguyen et al., "Modification of DNA duplexes to smooth their thermal stability independently of their base content for DNA sequencing by hybridization," *Nucl. Acids Res.*, 25(15):3059-3065, 1997.

Nicolau et al. "Liposome-Mediated DNA Transfer in Eukaryotic Cells," *Biochim. Biophys. Acta*, 721:185-190, 1982.

Nicolau et al. "Liposomes as Carriers for in Vivo Gene Transfer and Expression," *Methods Enzymology*, 149:157-176, 1987.

Neilsen et al., "Sequence-Selective Recognition of DNA by Strand Displacement with a Thymidine-Substituted Polyamide," *Science*, vol. 254, 1991, 1497-1500.

Nielsen, D. et al., "Preparation of Capped RNA Transcripts Using T7 RNA Polymerase," *Nucleic Acids Research*, 14(14), 1986, 5936.

Novina et al., "siRNA-directed inhibition of HIV-1 infection," *Nat. Med.*, 8:681-686, 2002.

Nykanen et al., "ATP requirements and small interfering RNA structure in the RNA interference pathway," *Cell*, 107(3):309-321, 2001.

Oates et al., "Too Much Interference: Injection of Double-Stranded RNA has Nonspecific Effects in the Zebrafish Embryo," *Developmental Biology*, 224:20-28, 2000.

Oberhauser et al., "Effective Incorporation of 2'-0-Methyl-Oligoribonucleotioes Into Liposomes Ano Enhanced Cell Association Through Modification With Thiocholesterol," *Nucleic Acids Research*, 20(3), 1992, 533-538.

Ohara et al., "One-sided polymerase chain reaction: The amplification of cDNA," *Proc. Natl. Acad. Sci. USA*, 86:5673-5677, 1989.

Omirulleh et al. "Activity of a chimeric promoter with the doubled CaMV 35S enhancer element in protoplast-derived cells and transgenic plants in maize," *Plant Mol. Biol.*, 21(3):415-428, 1993.

Ortiagao et al., "Antisence Effect of Oligodeoxynucleotides with Inverted Terminal Internucleotidic Linkages: A Minimal Modification Protecting against Nucleolytic Degradation," *Antisense Res. Dev.*, 2 1992, 129-146.

Pace et al., "Conformational stability and thermodynamics of folding of ribonucleases Sa, Sa2, and Sa3," *J. Mol. Biol.*, 279:271-286, 1998.

Paddison et al., "Short hairpin RNAs (shRNAs) induce sequence-specific silencing in mammalian cells," *Genes and Development*, 16:948-958, 2002.

Paddison et al., "Stable Suppression of Gene Expression by RNAI in Mammalian Cells," *PNAS*, 99(3):1443-1448, 2002.

Pagratis et al., "Potent 2'-amino-, and 2'-fluoro-2'-deoxyribonucleotide RNA inhibitors of keratinocyte growth factor," *Nature Biotechnology*, vol. 15, 1997, 68-73.

Paroo et al., "Challenges for RNAi in vivo," *TRENDS in Biotechnology*, vol. 22(8):390-394, Aug. 2004.

Paul et al., "Effective expression of small interfering RNA in human cells," *Nat. Biotechnol.*, 20:505-508, 2002.

Perkel, "Off-Target Effects Plague Drosphila RNAi," *The Scientist* Pages 1-5, 2006.

Plasterk et al., "The silence of the genes," *Curr. Opin. Genet. Dev.*, 10:562-567, 2000.

Pooga et al., "Cell penetrating PNA constructs regulate galanin receptor levels and modify pain transmission in vivo," *Nature Biotechnology*, vol. 16, 1998, 857-861.

Potrykus et al., "Molecular and general genetics of a hybrid foreign gene introduced into tobacco by direct gene transfer," *Mol. Gen. Genet.*, 199(2):169-77, 1985.

Prochiantz, A., "Getting hydrophilic compounds into cells: lessons from homeopeptides," *Current Opinion in Neurobiology*, vol. 6, 1996, 629-634.

Rakoczy et al., "Targeted Delivery of an Antisense Olignucleotide in the Retina: Uptake, Disruption, Stability, and effect," *Antisense Nucleic Acid Drug Dev.*, 6(3):207-213, 1996.

Ramos et al., "RNA recognition by a Staufen double-stranded RNA-binding domain," *EMBO Journal*, 19(5):997-1009, 2000.

Ratajczak et al., "In vivo treatment of human leukemia in a scid mouse model with c-myb antisense oligodeoxynucleotides," *Proceedings of the National Academy of Sciences*, vol. 89, 1992, 11823-11827.

Reichhart, J M. et al., "Splice-Activated UAS Hairpin Vector Gives Complete RNAi Knockout of Single or Double Target Transcripts in Drosophilia Melanogaster," *Genesis*, vol. 34., No. 1-2, 2002, 160-164.

Regnier et al., "Localization of a FITC-labeled phosphorothioate oligodeoxynucleotide in the skin after topical delivery by iontophoresis and electroporation," *Phar. Res.*, 15(10):1596-1602, 1998.

Reynolds et al., "Rational siRNA Design for RNA Interference," *Nature Biotechnology*, vol. 22(3):326-330, Mar. 2004.

Rippe et al., "DNA-Mediated Gene Transfer into Adult Rat Hepatocytes in Primary Culture," *Mol. Cell. Biol.*, 10:689-695, 1990.

Ruschkowski et al., "Biodistrubution and metabolism of a mixed backbone oligonucleotide (GEM 231) following single and multiple dose administration in mice," *Antisense Nucleic Acid Drug Dev.*, 5:333-345, 2000.

Ruvkun et al., "Glimpses of a Tiny RNA World," *Science*, 294:797-799, 2001.

Ryan et al., "Myc oncogenes: the enigmatic family," *Biochem. J.*, 314:713-721, 1996.

Ryter et al., "Molecular basis of double-stranded RNA-protein interactions: structure of a dsRNA-binding domain complexed with dsRNA," *Embo J.*, 17:7505-7513, 1998.

Samarsky et al., "RNAi in Drug Development: Practical Considerations," *RNA Interference Technology*, (Cambridge, Appasani, ed.,) pp. 384-395, 2005.

Sambrook et al., "Protocol for the Synthesis of the First Strand of cDNA," *Molecular Cloning, a Laboratory Manual*, Second Edition, Cold Spring Harbor Laboratory Press, pp. 8.60-8.63, 1989.

Scanlon, "Anti-Genes: siRNA, Ribozymes and Antisense," *Current Pharmaceutical Biotechnology*, vol. 5: 415-420, 2004.

Schell et al., "Uptake of polynucleotides by mammalian cells.," *Biochemical et Biophysica Acta*, vol. 340, 1974, 323-333.

Schlingensiepen, "The Role of Jun Transcription Factor Expression and Phosphorylation in Neuronal Differentiation, Neuronal Cell Death, and Plastic Adaptations in Vivo," *Cell. Mol. Neurobiol.*, vol. 14, 1994, 487-505.

Sedelnikova et al., "Targeting the human mdr1 gene by 125I-labeled triplex-forming oligonucleotides," *Antisense Nucleic Acid Drug Dev.*, 10:443-452, 2000.

Selden et al., "Human Growth Hormone as a Reporter Gene in Regulation Studies Employing Transient Gene Expression," *Mol Cell Biol.*, vol. 6, No. 9, 1986, 3173-3179.

Semple et al., "Efficient Encapsulation of Antisense Oligonucleotides in Lipid Vesicles Using Ionizable Aminolipids: Formation of Novel Small Multilamellar Vesicle Structures," *Biochimica et Biophysica Acta*, vol. 1510, 2001, 152-166.

Sergeeva et al., "Comparative Study of Modification of DNA and RNA by Oligo(2'-O-Methylribonucleotide) Derivatives," *Nucleosides, Nucleotides and Nucleic Acids*, vol. 17, No. 9-11: 2153-2156, 1998.

Sharp et al., "RNA interference," *Science*, 287:2431-2433, 2000.

Sharp, "RNAi and double-strand RNA," *Genes Dev.*, 13:139-141, 1999.

Sharp, "RNA Interference -2001," *Genes & Development*, vol. 15, pp. 485-490,2001.

Shi et al., "Mammalian RNAi for the masses," *Trends Genet.*, vol. 19, 2003, 9-12.

Shishkina et al., "A new method for the postsynthetic generation of abasic sites in oligomeric DNA," *Chem. Res. Toxicol.*, 13:907-912, 2000.

Shoeman, R.L. et al., "Fluorescence Microscopic Comparison of the Binding of Phosphodiester and Phosphorothioate (Antisense) Oligodeoxyribonucleotides to Subcellular Structures, Including Intermediate Filaments, the Endoplasmic Reticulum, and the Nuclear Interior," *Antisense & Nuc. Acid Drug Dev.*, vol. 7, 1997, 291-308.

Shuey et al., "RNAi: gene-silencing in therapeutic intervention," *Drug Discov. Today*, vol. 7, No. 20, 2002, 1040-1046.

Simeoni et al., "Peptide-Based Strategy for siRNA Delivery into Mammalian Cells," *Methods in Molecular Biology*, vol. 309: RNA Silencing: Methods and Protocols, 2005, 251-260.

Singh et al., "Real Time Kinetics of Ribozyme Reactions," *Ribozyme Biochemistry and Biotechnology*, 351-371, A17-A20, 2000.

Siomi et al., "Identification of Components of RNAi Pathways Using the Tandem Affinity Purification Method," *RNA Silencing, Methods and Protocols*, vol. 309, Humana Press 2005; pp. 1-9.

Sioud et al., "Strategies for the Design of Random siRNA Libraries and the Selection of anti-GFP siRNAs," *Methods in Molecular Biology*, vol. 309: RNA Silencing: Methods and Protocols, 2005, 83-91.

Sioud, M., "siRNA Delivery in Vivo," *Methods in Molecular Biology*, vol. 309: RNA Silencing: Methods and Protocols, 2005, 237-249.

Smardon et al., "EGO-1 is related to RNA-directed RNA polymerase and functions in germ-line development and RNA interference in C. elegans," *Curr. Biol.*, 10:169-178, 2000.

Sonveaux, E., "Protecting Groups in Oligonucleotide Synthesis," *Methods in Molecular Biology*, vol. 26: Protocols for Oligonucleotide Conjugates, 1994, 1-71.

Soutschek et al., "Therapeutic silencing of an endogenous gene by systemic administration of modified siRNAs," *Nature*, vol. 432, 2004, 173-178.

Spänkuck-Schmitt et al., "Effect of RNA Silencing of Polo-Like Kinase-1 (PLK1) on Apoptosis and Spindle Formation in Human Cancer Cells," *Journal of the National Cancer Institute*, 94(24):1863-1877, Dec. 18, 2002.

Sproat et al., "Highly Efficient Chemical Synthesis of 2'-0-methylioligoribunocleotides and Tetrabiotinylated Derivatives;Novel Probes That are Resistant to Degradation by RNA or DNA Specific Nucleases," *Nucleic Acids Research*, 17(9):3373-3386, 1989.

St. Johnston et al., "A conserved double-stranded RNA-binding domain," *Proc. Natl. Acad. Sci.*, USA, 89:10979-10983, 1992.

Stalnacke et al., "Radiotoxicity of 11C-methionine measured by the accumulation of DNA strand breaks in mammalian cells." *Eur. J. Nucl. Med.*, 11:166-170, 1985.

Stec et al., "Solid-Phase Synthesis, Separation, and Sterochemical Aspects of P-Chiral Methane and 4,4'-Dimethoxytriphenylmethanephosphonate Analogues of Oligodeoxyribonucleotides," *J. Org. Chem.*, vol. 50, 1985, 3908-3913.

Stec et al., "Automated Solid-Phase Synthesis, Separation, and Sterochemistry of Phosphorothioate Analogues of Oligodeoxyribonucleotides," *J. Am. Chem. Soc.*, vol. 106,1984, pp. 6077-6079.

Stec et al., "Reversed-phase high-performance liquid chromatographic separation of diastereomeric phosphorothioate analogues of oligodeoxyribonucleotides and other backbone-modified congeners of DNA," *J. Chromatog.*, vol. 326, 1985, 263-280.

Stein et al., "A Specificity Comparison of Four Antisense Types: Morpholino, 2'-O-methyl RNA, DNA, and Phosphorothioate DNA," *Antisense & Nucleic Acid Drug Development*, vol. 7, 1997, pp. 151-157.

Stein et al., "Two problems in antisense biotechnology: in vitro delivery and the design of antisense experiments," *Biochimica et Biophyica Acta*, vol. 1489, 1999, 45-52.

Stein et al., "Antisense Oligonucleotides as Therapeutic Agents—Is the Bullet Really Magical?," *Science*, vol. 261, 1993, 1004-1012.

Stein, "The experimental use of antisense oligonucleotides: a guide for the perplexed," *J. Clinical Invest.*, 108(5): 641-644, 2001.

Subramaniam et al., "nos-1 and nos-2, two genes related to Drosphila nanos, regulate primordial germ cell development and survival in *Caenorhabditis elegans*," *Development*, vol. 126, No. 21: 4861-4871, 1999.

Sui et al., "A DNA vector-based RNAi technology to suppress gene expression in mammalian cells," *Proc. Natl. Acad. Sci. USA*, 99(8):5515-5520, 2002.

Summerton, "Morpholino Antisense Oligomers: Design, Preparation and Properties," *Antisense & Nuc. Acid Drug Dev.*, 7, 1997, 187-195.

Sun Qi et al., "Complex genetic interactions among four receptor tyrosine phosphates regulate axon guidance in Drosophila," *Molecular and Cellular Neuroscience*, vol. 17, No. 2: 274-291; 2001.

Svoboda et al., "RNAi Oocytes and Preimplantation Embryos: Effectiveness of Hairpin dsRNA," *Biochemical and Biophysical Research Communications*, 287:1099-1104, 2001.

Tabara et al., "The rde-1 gene, RNA interference, and transposon silencing in *C. elegans*," *Cell*, 99:123-132, 1999.

Tavernarakis et al., "Heritable and Inducible Genetic Interference by Double-Stranded RNA encoded by Transgenes," *Nature Genetics*, 24:180-183, 2000.

Testa et al., "Thermodynamics of RNA-RNA Duplexes with 2- or 4-thiouridines," *Biochemistry*, 38:16655-16662, 1999.

Theus et al., "A Simple Assay for Determining the Capping Efficiencies of RNA Polymerases Used for in Vitro Transcription," *BioTechniques*, vol. 9, No. 5, 1990, 610-615.

Thompson et al., "Clustal W: improving the sensitivity of progressive multiple sequence alignment through sequence weighting, position-specific gap penalties and weight matrix choice," *Nucleic Acids Res.* 22:4673-4680, 1994.

Thuong et al. "Oligo(Alpha-Deosynucleotide)s Covalently Linked to Intercalating Agents: Differential Binding to Ribo- and Deoxyribopolynucleotides and Stability Towards Nuclease Digestion," *Proc Nat Acad Sci USA*, vol. 84, 1987, 5129-5133.

Timmons et al., "Specific interference by ingested dsRNA," *Nature*, 395:854, 1998.

Trotta et al., "BCR/ABL activates mdm2 mRNA translation via the La antigen," *Cancer Cell*, 3:145-160, 2003.

Troy et al., "Downregulation of Cu/Zn superoxide dismutase leads to cell death via the nitric oxide-peroxynitrite pathway," *The Journal of Neuroscience*, vol. 16, No. 1, 1996, 253-261.

Tuschl, "RNa interference and small interfering RNAs," *Chembiochem.*, 2:239-245, 2001.

Tuschl et al., "Small Interfering RNAs: A Revolutionary Tool for the Analysis of Gene Function and Gene Therapy," *Molecular Interventions*, vol. 2(3):158-167, Jun. 2002.

Uhlmann et al., "Antisense Oligonucleotides: A New Therapeutic Principle," *Chemical Reviews*, vol. 90, No. 4: 543-583, 1990.

Verma et al., "Gene Therapy—Promises, Problems and Prospects," *Nature*, vol. 389, 1997, 239-242.

Viari et al., "Sequence Analysis of Unprotected Tri-Deoxyribonucleoside Diphosphates by 252Cf-Plasma Desorption Mass Spectrometry," *Biomed. Environ. Mass Spectrom.*, vol. 14, 1987, 83-90.

Vickers et al., "Efficient Reduction of Target RNAs by Small Interfering RNA and RNase H-dependant Antisense Agents," *The Journal of Biological Chemistry*, 278:7108-7118, 2003.

Vlassov et al., "Transport of oligonucleotides across natural and model membranes," *Biochimica et Biophysica Acta*, vol. 1197, 1994, 95-108.

Vyas et al., "Ligand-receptor-mediated drug delivery: an emerging paradigm in cellular drug targeting," *Crit. Rev. Ther. Drug Carrier Syst.*, 18(1):1-76, 2001.

Wagner, R. W. et al., "Antisense Gene Inhibition by Oligonucleotides Containing C-5 Propyne Pyrimidines," *Science*, vol. 260, 1993, 1510-1513.

Wagner, R. W., "The State of the Art in Antisense Research," *Nature Medicine*, vol. 1, No. 11, 1995, 1116-1118.

Wagner, R. W. et al., "Potent and selective inhibition of gene expression by an antisense heptanucleotide," *Nature Biotechnology*, vol. 14, 1996, 840-844.

Walker et al., "Isothermal in vitro amplification of DNA by restriction enzyme/DNA polymerase system," *Proc. Natl. Acad. Sci. USA*, 89:392-396, 1992.

Waterhouse et al., "Gene silencing as an adaptive defense against viruses," *Nature*, 411:834-842, 2001.

Williams, "Gene expression domains as markers in developmental toxicity studies using mammalian embryo culture," *Int. J. Dev. Biol.*, 41(2):359-364, 1997.

Wilson, T.M., "Gene therapy for Cystic Fibrosis: Challenges and Future Directions," *Journal of Clinical Investigation*, vol. 96, 1995, 2547-2554.

Wincott et al., "Synthesis, Deprotection, analysis and Purification of RNA and Ribozymes," *Nucl. Acids Res.*, 23:2677-2684, 1995.

Wong et al., "Appearance of beta-lactamase activity in animal cells upon liposome-mediated gene transfer," *Gene*, 10, 1980, 87-94.

Wu et al., "Prevention of chain cleavage in the chemical synthesis of 2'-silylated oligoribonucleotides," *Nucl. Acids Res.*, 17(9):3501-3517, 1989.

Wu-Scharf et al., "Transgene and transposon silencing in *Chlamydomonas reinhardtii* by a DEAH-box RNA helicase," *Science*, 290:1159-1162, 2000.

Xia et al., "siRNA-mediated gene silencing in vitro and in vivo," *Nat. Biotechnol.*, 20(10):1006-1010, 2002.

Yamakawa et al., "Properties and Anti-HIV Activity of Nicked Dumbbell Oligonucleotides," *Nucleosides & Nucleotides*, 15 (1-3), 1996, 519-529.

Yang et al., "Evidence that processed small dsRNAs may mediate sequence-specific mRNA degradation during RNAi in Drosophila embryos," *Current Biology*, vol. 10, No. 19, 2000, 1191-120.

Yang et al., "Short RNA duplexes produced by hydrolysis with *Escherichia coli* RNase III mediate effective RNA interference in mammalian cells," *Proc. Natl. Acad. Sci., USA*, 99(15):9942-9947, 2002.

Yoo, H, "Enhanced delivery of antisense oligonucleotides with fluorophore-conjugated PAMAM dendrimers," *Nucleic Acids Research*, 28:4225-4231, 2000.

Yu et al., "RNA interference by expression of short-interfering RNAs and hairpin RNAs in mammalian cells," *Proc. Natl. Acad. Sci., USA*, 99:6047-6052, 2002.

Zabner et al., "Cellular and Molecular Barriers to Gene Transfer by a Cationic Lipid," *Journal of Biological Chemistry*, 270(32):18997-19007, Aug. 1995.

Zamore et al., "RNAi: double-stranded RNA directs the ATP-dependent cleavage of mRNA at 21 to 23 nucleotide intervals," *Cell*, 101:25-33, 2000.

Zamore, "RNA interference: listening to the sound of silence," *Nat. Struct. Biol.*, 8:746-750, 2001.

Zamore, et al, "ATP Requirements and Small Interfering RNA Structure in the RNA Interference Pathway", *Cell*, vol. 107(3), Nov. 2, 2001, pp. 309 - 321.

Zamore, "Thirty-Three Years Later, a Glimpse at the Ribonuclease III Active Site," *Molecular Cell*, 8(6):1158-1160, Dec. 1, 2001.

Zhang et al., "Influence of different chelators (HYNIC, MAG3 and DTPA) on tumor cell accumulation and mouse biodistribution of technetium-99m labeled to antisense DNA," *Eur. J. Nucl. Med.*, 27(11):1700-1707, 2000.

Zhang et al., "Uptake and distribution of fluorescein-labeled D2 dopaminereceptor antisense oligdeoxynucleotide in mouse brain," *J. Mol. Neurosci.*, 7:13-28, 1996.

Zhang et al., "In vitro investigations of tumor targeting with 99mTc-labeled antisense DNA," *J. Nucl. Med.*, 42(11):1660-1669, 2001.

Zhao et al., "Double-Stranded RNA Injection Produces Nonspecific Defects in Zebrafish," *Developmental Biology*, 229:215-223, 2001.

Zuckermann et al., "Design, construction and application of a fully automated equimolar peptide mixture synthesizer," *Int. J. Peptide Protein Res.*, vol. 40, 1992, 497-506.

Zuckermann et al., "Efficient Method for the Preparation of Peptoids [Oligo(N-substituted glycines)] by Submonomer Solid-Phase Synthesis," *Journal of the American Chemical Society*, vol. 114, No. 26, 1992, 10646-10647.

* cited by examiner

5'-TAATACGACTCACTATAGGGAGAAACC TARGET 19MER-AAGC - COMP 19MER- TT-3'
3'-ATTATGCTGAGTGATATCCCTCTTTGG - COMP 19MER-TTCG TARGET 19MER- AA 5'

| Transcribe w/T7
| RNA polymerase
▼

5'-GGGAGAAACC   UU3'

| Digest with
| RNase A

SEQUENCE LISTING

```
<160> NUMBER OF SEQ ID NOS: 42

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
gggagacagg                                                                10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gggagaaacc                                                                10

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
```

-continued

```
<220> FEATURE:
<223> OTHER INFORMATION: Description of Combined DNA/RNA Molecule: RNA
      Oligo with 2'-deoxy thymidines at 5' end

<400> SEQUENCE: 3
gggagauccg gagcgaauat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 4
uauucgcucc ggaucuccct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 5
cuucuaccag cagcagcagt t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 6
cugcugcugc ugguagaagt t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
cacacaacgu cuuggagcgt t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end
```

-continued

```
<400> SEQUENCE: 8
cgcuccaaga cguugugugt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 9
cgauuccuuc uaacagaaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 10
uuucuguuag aaggaaucgt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 11
gcgacguucc ugaaccact t                                               21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 12
gugguuucag gaacgucgct t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: Description of Combined DNA/RNA Molecule: RNA
      Oligo with 2'-deoxy thymidines at 5' end
```

-continued

<400> SEQUENCE: 13
ugauggcaac aauauccact t                                          21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 14
guggauauug aagccaucat t                                          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 15
aaaguuguca uggaugacct t                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 16
ggucauccau gacaacuuut t                                          21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 17
gaaggccaug ccagugagct t                                          21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

```
<400> SEQUENCE: 18
gcucacuggc auggccuuct t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 19
caugaggucc accaccugt t                                               21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 20 cagggugug gaccucaugt t                                               21

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 21
ggtaatacga ctcactatag ggagacagg                                      29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
aagtggatat tgttgccatc acctgtctc                                      29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 23
aatgatggca acaatatcca ccctgtctc                                      29

<210> SEQ ID NO 24
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 24
aaggtcatcc atgacaactt tcctgtctc                                       29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
aaaaagttgt catggatgac ccctgtctc                                       29

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
aagcttcact ggcatggcct tccctgtctc                                      30

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
aagaaggcca tgccagtgag ccctgtctc                                       29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
aacagggtgg tggacctcat gcctgtctc                                       29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
aacatgaggt ccaccaccct gcctgtctc                                       29

<210> SEQ ID NO 30
<211> LENGTH: 29
<212> TYPE: DNA
<213> ORGANISM: Artificial Sequence
<220> FEATURE:
```

-continued

```
<223> OTHER INFORMATION: Description of Artificial Sequence: Synthetic
      Primer

<400> SEQUENCE: 30
ggtaatacga ctcactatag ggagacagg                                            29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
aatttctgtt agaaggaatc gcctgtctc                                            29

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
aacgattcct tctaacagaa acctgtctc                                            29

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 33
ugauggcaac aauauccact t                                                    21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: Description of Combined DNA/RNA Molecule: RNA
      Oligo with 2'-deoxy thymidines at 5' end

<400> SEQUENCE: 34
guggauauug aagccaucat t                                                    21

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
taatacgact cactatagg                                                       19

<210> SEQ ID NO 36
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
attatgctga gtgatatcc                                                    19

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
taatacgact cactataggg agaaacc                                            27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
attatgctga gtgatatccc tctttgg                                            27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
taatacgact cactataggg agacagg                                            27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
attatgctga gtgatatccc tctgtcc                                            27

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
ggacagaggg                                                              10

<210> SEQ ID NO 42
<211> LENGTH: 10
<212> TYPE: DNA
```

```
<213> ORGANISM: Artificial Sequence
<220> FEATURE:
<223> OTHER INFORMATION: Description of Artificial Sequence:  Synthetic
      Primer

<400> SEQUENCE: 42
ccaaagaggg                                                            10
```

▼

HIGH POTENCY SIRNAS FOR REDUCING THE EXPRESSION OF TARGET GENES

The present application is a continuation application of U.S. patent application Ser. No. 10/355,820 filed Jan. 31, 2003, now abandoned, which application claims the benefit of U.S. Provisional Application Ser. No. 60/353,332 filed Feb. 1, 2002. The entire text of each application is herein incorporated by reference.

BACKGROUND OF THE INVENTION

1. Field of the Invention

The present invention relates to improved methods for making small interfering RNA (siRNA), improved siRNA made by such methods, their use in the modulation of gene expression in mammalian and other cell types and their use in medical therapies.

2. Description of Related Art

RNA interference (RNAi) is a phenomenon in which a double stranded RNA (dsRNA) specifically suppresses the expression of a gene bearing its complementary sequence. The phenomenon was originally discovered in *Caenorhabditis elegans* by Fire and Mello (Fire et al., 1998). RNAi has since become a useful research tool for many organisms. Although the mechanism by which dsRNA suppresses gene expression is not entirely understood, experimental data provide important insights. In non-mammalian systems, it appears that longer dsRNA are processed into small, 21-23 nt dsRNAs by an enzyme containing RNase III motifs (Bernstein et al., 2001; Grishok et al., 2001; Hamilton and Baulcombe, 1999; Knight and Bass, 2001; Zamore et al., 2000). It has been theorized that the RNAi nuclease complex, called RNA-induced silencing complex (RISC), helps the small dsRNAs recognize complementary mRNAs through base-pairing interactions. Following the siRNAs interaction with its substrate, the mRNA is targeted for degradation, perhaps by enzymes that are present in the RISC (Montgomery et al., 1998).

Until recently, RNAi could only be used in non-mammalian cells. This is because mammalian cells have a potent antiviral response pathway that induces global changes in gene expression when the cells are challenged with long (>30 nucleotides) dsRNA molecules. This pathway has made it impossible to specifically suppress the expression of proteins in mammalian cells using the typical RNAi molecules, which are hundreds of nucleotides long.

Recently Elbashir et al. (2001) published a method to bypass the antiviral response and induce gene specific silencing in mammalian cells. Several 21 nucleotide (nt) dsRNAs with 2 nt 3' overhangs were transfected into mammalian cells without inducing the antiviral response. These small dsRNAs, referred to as small interfering RNAs (siRNAs) proved capable of inducing the specific suppression of target genes. In one set of experiments, siRNAs complementary to a luciferase gene were co-transfected with a luciferase reporter plasmid into NIH3T3, COS-7, HeLaS3, and 293 cells. In all cases, the siRNAs were able to specifically reduce luciferase gene expression. In addition, the authors demonstrated that siRNAs could reduce the expression of several endogenous genes in human cells. The endogenous targets were lamin A/C, lamin B1, nuclear mitotic apparatus protein, and vimentin. The use of siRNAs to modulate gene expression in mammalian cells has now been repeated at least twice (Caplen et al., 2001; Hutvagner et al., 2001). This technology has great potential as a tool to study gene function in mammalian cells and may lead to the development of pharmacological agents based upon siRNA.

To realize this potential, siRNAs must be designed so that they are specific and effective in suppressing the expression of the genes of interest. Methods of selecting the target sequences, i.e. those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above.

The making of siRNAs to date has been through direct chemical synthesis or through processing of longer, double stranded RNAs through exposure to *Drosophila* embryo lysates or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single stranded RNA-oligomers followed by the annealing of the two single stranded oligomers into a double stranded RNA. Methods of chemical synthesis are diverse. Non-limiting examples are provided in U.S. Pat. Nos. 5,889,136; 4,415,732; 4,458,066, expressly incorporated herein by reference, and in Wincott et al. (1995).

Elbashir and colleagues have published the procedure that they use to design, prepare, and transfect siRNAs for mammalian RNAi experiments. ("The siRNA user guide" Aug. 26, 2001). Similar protocols and procedures are available in Dharmacon Technical Bulletin #003, July 2001. These guides recommend chemically synthesizing two 21-mer RNA oligomers with two deoxythymidines at the 3' terminus and 19 nucleotide complementary sequences. The two ribo-oligomers are mixed to allow them to hybridize. The products are then mixed with a transfection agent and added to cell culture at concentrations of about 100 nM. The pamphlet further recommends that the selection of the target sequence should be constrained so that they begin with AA and end with TT, so that the AA and TT overhang sequences may be fashioned from the target sequence itself. The pamphlet indicates that the symmetric 3' overhangs aid the formation of approximately equimolar ratios of sense and antisense target RNA-cleaving siRNAs.

Several further modifications to siRNA sequences have been suggested in order to alter their stability or improve their effectiveness. It is suggested that synthetic complementary 21 mer RNAs having di-nucleotide overhangs (i.e. 19 complementary nucleotides+3' non-complementary dimers) may provide the greatest level of suppression, although actual data demonstrating this advantage is lacking. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

To date, such chemically synthesized siRNAs are found to work optimally when they are in cell culture at concentrations of 25-100 nM. Elbashir et al. used concentrations of about 100 nM to achieve effective suppression of expression in mammalian cells. Unfortunately, ribo-oligomers are very expensive to chemically synthesize, making the procedure less appealing and not cost effective to many researchers and pharmaceutical companies. Furthermore, in foreseeable medical applications of siRNA, it would be desirable to achieve target gene inhibition with as little siRNA as possible. Therefore, siRNAs that are still as effective, if not more so, at lower concentrations would be significantly advantageous. There is therefore a need in the art for siRNAs that function at lower concentrations to modulate or attenuate the expression of target genes.

siRNAs have been most effective in mammalian cell culture at about 100 nM. In several instances, however, lower concentrations of chemically synthesized siRNA have been used. Caplen, et al. used chemically synthesized siRNAs at 18 nM. However, Caplen used semi-quantitative RT-PCR to monitor reduction of transcripts. The semi-quantitative nature of the assay makes unclear how great an effect this low concentration of siRNA had on transcript levels. Hutvagner, et al. used chemically synthesized siRNAs at concentrations of 70 nM to elicit a response. Although less than 100 nM, 70 nM may still represent a substantially prohibitive concentration for some applications. Although Elbashir et al. also indicated that they could use lower amounts of siRNA in the cell culture and still observe suppression, they did not provide data nor did they indicate by how much the expression was reduced at these lower levels.

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g. T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25 mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g. T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences. U.S. Pat. No. 5,795,715 was filed Jun. 17, 1994, well before the phenomenon of RNA interference was described by Fire et al. (1998). The production of siRNA was, therefore, not contemplated by these authors.

As described above, there is a need for siRNAs of increased potency, both for general research and for use as medical or veterinary therapies. siRNAs of increased potency would decrease the risk or adverse reactions or other, undesired effects of medical therapies using siRNA. Fewer molecules of siRNA of increased potency would be needed for such therapies, with concomitant benefits to patients.

SUMMARY OF THE INVENTION

The present invention is directed to compositions and methods useful in the production of double stranded RNAs (dsRNAs) of increased potency for use as small interfering RNA (siRNA) in the suppression of gene expression and the treatment of disease. The invention provides methods of synthesis and use of siRNA that result in less costly siRNA and siRNA of substantially and significantly higher potency.

SiRNAs of increased potency are those wherein the provision of fewer molecules of siRNA is effective in achieving modulation or attenuation of gene expression when compared to the number of standard siRNA molecules required to achieve the same level of modulation or attenuation of target gene expression. Standard siRNAs are those provided by typical chemical synthesis methods and incorporating the usual, unmodified nucleotides that make up the RNA polymer, i.e. adenine, cytosine, guanine, and uracil.

Potency of siRNA may be evaluated by a number of means as will be appreciated by those of skill in the art. The level of attenuation of gene expression may be compared between replicate cells or organisms treated with equal molar amounts of standard and siRNAs of increased potency designed to target the same target sequence within a target gene or genes. Additionally, response curves may be generated wherein levels of expression of a target gene in response to varying concentrations of siRNAs are measured and displayed for standard and siRNAs of increased potency delivered to replicate cells or organisms. Other means of comparison are contemplated. Generally, any means will suffice that reveals that fewer molecules of a particular siRNA are required to achieve the same level of modulation or attenuation as a standard siRNA used under equivalent conditions and targeting the same target sequence.

The use of siRNAs of increased potency therefore results in an increased modulation or attenuation of gene expression in comparison to standard siRNAs when both are used under identical conditions. Such increased attenuation may be recognized in a number of measures. Non limiting examples include altered gene expression measurable through decreased transcript abundance, decreased protein product abundance, decreased activity associated with the protein product, or an altered phenotype associated with the protein product. Such changes in expression or phenotype may be large or small yet still reveal the high potency of the presently disclosed siRNAs.

The choice of effect measured, the context of its measurement, and the metric used all interact to determine the absolute magnitude of the response. Nevertheless, the identification of siRNA of increased potency is unambiguous even though the relative effectiveness of standard and siRNAs of increased potency may be indicated by small relative changes in phenotype or expression levels.

A relative change in expression levels or phenotype may be on the order of any level greater than 1% to 100%. Thus, in one example, relative cell proliferation may be altered by about 2% at an siRNA concentration of 1 nM (FIG. 10) and will be indicative of the high potency of the siRNA provided by the present invention. In another example, the relative transcript levels of a gene may be reduced more effectively by siRNAs of increased potency of the present invention across a continuous range of concentrations (FIG. 11), resulting in relative potency ranging continuously from greater than 0% to 100%. siRNAs of increased potency may be 1%, 2,%, 3%, 4%, 5%, 6%, 7%, 8%, 9%, 10%, 15%, 20%, 25%, 30%, 35%, 40%, 45%, 50%, 60%, 70%, 80%, 90%, or 100% more potent. SiRNAs of increased potency may also be described as 1-, 2-, 3-, 4-, 5-, 6-, 7-, 8-, 9-, 10-, 11-, 12-, 13-, 14-, 15-, 20-, 25-, 30-, 40-, 50-, 60-, 70-, 80-, 90-, 100-, 200-, and more fold more potent than standard siRNAs. Potency may thus be further defined with respect to specific processes used to determine potency. Particularly preferred embodiments for calculating increased potency include the comparison of the magnitudes or importance of the desired effects of administering siRNAs of the present invention to the effects of administering siRNAs made from standard or currently available protocols.

The inventors have made the surprising discovery that the method of synthesis of siRNA can dictate its potency. Specifically, the inventors have discovered that enzymatic synthesis of siRNAs through the methods of the present invention provides for siRNA with substantially and significantly greater potency. In one example, the optimal concentration of siRNA made by the present invention for use in the transfection of cells is unexpectedly up to 20-fold less than what is commonly used. Thus, these siRNAs of increased potency may be 20-fold more potent than standard siRNAs. Since siRNAs synthesized by the methods and compositions of the present invention are unexpectedly, and significantly more potent that those available otherwise, methods of use of these siRNAs are provided that incorporate this highly surprising and unexpected potency. These methods include methods of attenuating gene expression in host cells, organs, tissues, and whole organisms.

An advantage of this aspect of the present invention lies in providing for siRNA that may be enzymatically synthesized from a great range of template sequences. Templates are provided that contain structures specifically adapted for the efficient synthesis of siRNAs of increased potency in a variety of situations without limitation and for any target gene sequence that may be desired. These siRNAs may be from 15 to 30 nucleotides in length, may contain dinucleotide or other overhang sequences, may contain modified nucleotides, or other modifications as desired. The methods of the present invention also provide for the use of dT, and other overhang sequences, as well as the incorporation of modified nucleotide analogs, which may also increase effectiveness of the siRNA.

Compositions of the present invention include oligonucleotide and polynucleotide templates and methods for the use of those templates in enzymatic synthesis of siRNA of increased potency, which is employed in the specific inhibition of target gene expression. The templates may comprise a polynucleotide sequence comprising a target sequence. The target sequence may be derived from the sequence of a target gene.

A target gene is a gene whose expression is targeted for interference, inhibition, attenuation, disruption, augmentation, or other modulation. Preferably, the expression is targeted for interference. Most preferably the expression is targeted for attenuation.

The inventors have also made the surprising discovery that incorporation of modified nucleotide analogs may increase the potency of siRNA. Modified nucleotide analogs may be incorporated in siRNAs through either enzymatic synthesis or chemical synthesis. Enzymatic synthesis is the use of RNA polymerases to polymerize nucleotides into single or double stranded RNA for use as siRNA through the methods and compositions presently disclosed. Chemical synthesis is the use of any other method to synthesize single or double stranded RNA for use in siRNA.

The inventors have found that modified nucleotide analogs increase the potency of siRNAs whether incorporated through enzymatic or chemical synthesis. In particular, enzymatic incorporation of modified nucleotide analogs produces even further enhancement of siRNA potency over that achieved through enzymatic synthesis alone. Modified nucleotide analogs incorporated through chemical synthesis have also been found to unexpectedly enhance siRNA potency. Increased potency of siRNA may thus be achieved through the enzymatic synthesis of siRNA, through the incorporation of modified nucleotide analogs through enzymatic synthesis, and through the incorporation of modified nucleotide analogs through chemical synthesis.

The inventors have also discovered that siRNAs wherein the duplex structure of the double stranded RNA is of reduced stability are significantly more potent. In particular, nucleotide analogs that reduce the stability of RNA duplexes enhance the potency of siRNAs.

RNA duplex stability may be measured by several methods, as will be appreciated by one of skill in the art. A typical example is the measurement of the melting temperature (TM) of the duplex in a specified set of conditions, such as, but not limited to specified salt concentrations, pH, etc. See, for example the thermal melting analysis provided in U.S. Pat. No. 6,005,087, incorporated herein by reference. Also see, generally, Sambrook (2001), and by way of additional example, Dubins, et al. (2001) and Testa et al. (1999). Reduced duplex stability may be on the order of a 1%, 2,%, 3%, 4%, 5%, 6%, 7%, 8%, 9%, 10%, 15%, 20%, 25%, 30%, 35%, 40%, 45%, 50% or more decrease in TM or like measure in comparison to unmodified, or fully complementary, or other RNA, DNA, or RNA/DNA duplexes. Reduced RNA duplex stability may be further defined by the particular methods chosen, as will be appreciated by one of skill in the art. Such methods can include assays of siRNA potency as described above.

Reduced stability of the siRNA duplex may be achieved through a variety of techniques. Nucleotide analogs, as described above, may be introduced such that the resultant duplex of the siRNA is of reduced stability. The following discussion is a non-limiting list of possible modifications to be made to the siRNA that may result in higher potency through reduced stability of the siRNA duplex structure.

Phosphorothioates—Phosphorothioates reduce duplex stability approximately 0.5° C. to 1° C. per modification. They can be substituted at one or more nucleotide positions along the length of the siRNA.

Inosine—Substitution of inosine (I) for G's at one or more positions in the siRNA will reduce duplex stability and thereby enhance siRNA potency. I:C base pairs form only two hydrogen bonds (as opposed to three in G:C base-pairs), reducing the stability of the duplex (Kawase et al. 1986).

4-Thio uridine—4-thio uridine forms only a single hydrogen bond with adenosine (Testa et al. 1999) and therefore the substitution of one or more uracils (U) in the siRNA results in duplex structures of reduced stability.

4-Ethyl cytosine—4-ethyl cytosine forms only two hydrogen bonds with guanosine, reducing the stability of G:C base-pairs (Nguyen et al. 1997). Use of 4-ethyl cytosine at one or more positions in the siRNA is expected to reduce stability of the duplex structure.

3-Nitropyrrole nucleoside and 5-nitroindole nucleoside (5-nitroindole)—Both of these nucleosides hybridize to all four natural nucleosides, but with lower affinity than canonical base-pairs (Bergstrom et al. 1997). Thus, substitution of an appropriate number of nucleotides of the siRNA with these nucleosides will result in reduced overall duplex stability without loss of appropriate sequence specificity. The selection of the appropriate number and position of such nucleoside substitutions are well within the skill of the ordinary artisan (Bergstrom et al. 1997).

Abasic sites—There are several nucleotide linkers that do not have an associated base. These can be introduced at one or more sites in the sense strand of the siRNA to eliminate one or more base-pairs and reduce the stability of the siRNA duplex. Nucleic acid helices with abasic sites have reduced melting temperatures, i.e. reduced duplex stabilities. (Shishkina et al. 2000).

Mismatches—One or more mismatches can be introduced along the length of the siRNA duplex. The mismatched bases should be in the sense strand of the siRNA so as not to reduce the binding affinity of the anti-sense strand for the mRNA target. The net effect of such mismatches on duplex stability is the same as that achieved by the other chemical substitutions described above. That is, the stability of the duplex structure of the siRNA is reduced relative to that of a completely and absolutely complementary match between the two single strand sequences that make up the RNA duplex.

All of the discoveries described are directed to the modulation, especially the attenuation of the expression of a target gene. The target gene may include sequences encoding polypeptides or polynucleotide sequences that regulate the replication, transcription, translation or other process important to the expression of the gene. The target gene need not necessarily encode a polypeptide but may encode other cellular components, such as ribosomal RNA, splicosome RNA, transfer RNA, etc.

The target gene may exist as an endogenous gene, which occurs naturally within a cell, or an exogenous gene, which does not naturally occur within a cell. Exogenous genes may, for example, be a transgene or synthetic gene, or a gene of a pathogen, parasite, or commensal organism. Preferably, the target gene exists within a vertebrate cell, although the invention is not limited to the making of siRNA for use in vertebrate cells.

The target sequence may be the entire sequence of the target gene, or, preferably, only a portion of the target gene. Preferably, the target sequence is a contiguous subsequence of the target gene sequence and is from 15 to 30 nucleotides in length. The target sequence may be 15, 16, 17, 18, 19, 20, 21, 22, 23, 24, 25, 26, 27, 28, 29 or 30 nucleotides in length. The size and sequence of the target gene used as the target sequence may be selected by those of skill in the art so as to optimize the interfering effects of the product siRNAs.

Within a polynucleotide template for making siRNA, the target sequence may be operatively linked to a promoter (FIG. 1). Preferably, the promoter is a sequence sufficient to direct the transcription of the template sequence into RNA when contacted with RNA polymerase. Such promoters are well known to those of skill in the art and include, but are not limited to the T7, T3, and SP6 promoters. Polymerases may be chosen so as to maximize the benefits of enzymatic synthesis of siRNA. Such polymerases are well known to those of skill in the art and include, but are not limited to the T7, T3, SP6, polymerases and derivatives thereof. Such a choice is within the skill of one in the art. In one embodiment, the polymerase is selected from T7, T3, and SP6. In a preferred embodiment, the polymerase is T7 RNA polymerase. Naturally, the selection of appropriate polymerase is performed in conjunction with the selection of appropriate promoter so that the polymerase functionally recognizes the promoter, leading to the synthesis of an RNA strand.

If operatively linked to a T7, T3, SP6 or similar promoter, the target sequence may be contiguous with the promoter sequence (FIG. 1). Milligan et al. (1987) reports the use of relatively short template nucleotides in the synthesis of single-stranded RNA products. In particular, Milligan et al. disclose necessary sequence constraints imposed by the use of T7, T3, or SP6 RNA polymerase promoters. Therefore, in an embodiment of the invention, if the target sequence is contiguous with the promoter sequence, the target sequence adjacent to the promoter sequence preferably begins with the dinucleotide sequence of GG or GA.

However, the present invention in part provides compositions and methods that surmount the limitations identified by Milligan et al. by providing a template comprising at least one leader sequence interposed between the promoter and the template sequence (FIG. 2 and FIG. 3). Thus, in another preferred embodiment, the target sequence present in the polynucleotide template for making siRNA may be operatively linked to a promoter without being contiguous with it. A spacer or leader sequence may be interposed between the promoter sequence and the target sequence of the template. Preferably, such a leader sequence provides the dinucleotide sequences of GG or GA that aid the efficient transcription from a T7, T3, SP6 or similar promoter. Such a leader sequence may be any length that does not interfere with the effective functioning of the promoter. Such a leader sequence may be 10, 12, 14, 16, 18, 20, 22, 24, 26, 28, 30, 40, or 50 or more nucleotides in length. Preferably, the leader sequence is about 10 nt, but may be 9, 8, 7, 6, 5, 4, 3, or even 2 or 1 nt in length. In one embodiment, the leader sequence is selected from SEQ ID NO: 1 and SEQ ID NO: 2. In another embodiment, the leader sequence is that of SEQ ID NO: 1. In another embodiment, the leader sequence is that of SEQ ID NO: 2. In yet another embodiment, the leader sequences of two templates are different sequences.

Of course, and as will be appreciated by those of skill in the art, specifying the template sequence for enzymatic synthesis is generally accomplished by listing the nucleotide sequence of the template in the 5' to 3' direction, and by convention, as the top, or sense strand of a double stranded duplex. (FIGS. 1-4). However, the template sequence so specified in the context of the present invention is not limited to the sense strand. For example, the double stranded molecule, as discussed above, can function as a template for RNA synthesis. Furthermore, the antisense strand alone can function as a template for RNA synthesis. Therefore, following convention, as used herein the description of polynucleotides will be generally from 5' to 3' and will recite the sense strand, although the invention is not limited to transcription from the sense strand as listed, but will encompass both the sense and the antisense (or bottom) strand and a single, antisense strand (FIGS. 1-4). Therefore, for example, the embodiments that comprise templates comprising overhang encoding sequences comprising the nucleotide sequence of TT, are designed so that the resultant RNA strand formed comprises an overhang of UU or the like.

In preferred embodiments, the invention provides for RNases that have activity in relation to the nucleotide sequences of the leader sequence. Thus, RNase T1 preferentially digests single-stranded RNA at G residues. RNase A preferentially digests at C and U residues. If RNase T1 is to be used, the last nucleotide in the leader sequence is preferred to be a G to eliminate the entire leader sequence from the siRNA. Likewise, if RNase A is to be used, the last nucleotide in the leader sequence should be a C or U. In additional, preferred embodiments, the RNase may be RNase Sa, RNase Sa2, or RNase Sa3. In a particularly preferred embodiment, the RNase is RNase Sa.

In yet another preferred embodiment, the polynucleotide template for synthesizing small interfering RNA comprises a promoter, a target sequence, and a complementary sequence to the target sequence positioned between the target sequence and the 3' terminus of the template (FIG. 4).

The templates provided by the invention may be used in the synthesis of siRNA of increased potency. The embodiments of the synthesis methods preferably comprise the transcription of the templates by RNA polymerase, annealing of the single stranded RNA products to form double stranded RNA, and RNAse digestion to remove unnecessary single stranded RNA from the double stranded RNA product (FIGS. 2, 3, and 4).

In one preferred embodiment, the synthesized RNA is such that it is partially self-complementary and so forms a stem and loop structure (FIG. 4). In alternative and preferred embodiments, two strands of RNA may be made that are substantially complementary so that they form a duplex upon provision of appropriate conditions (FIGS. 1, 2, and 3). In yet another preferred embodiment, a single RNA strand may be synthesized that complements a template RNA strand itself made through other means (RNA copying). Additionally, a single RNA strand may be synthesized that complements a pre-existing single stranded RNA molecule and allowed to form a duplex therewith, forming a dsRNA functional as a siRNA of increased potency. In a further preferred embodiment, the synthesized RNA is further treated with nucleases in order to digest or remove template nucleic acids or portions of the synthesized RNA. In an additional preferred embodiment, once synthesized, the RNA products may be purified or further manipulated before use as siRNA. In an alternative embodiment, the RNA products may be used directly without further manipulation.

In still more preferred embodiments, the siRNA includes modifications to either the phosphate-sugar backbone or the nucleoside. In one embodiment, the phosphodiester linkages of natural RNA are modified to include at least one of a nitrogen or sulfur hetero-atom. In another embodiment, bases may be modified to block the activity of adenosine deaminase. In some embodiments, the modified nucleotide analogs may be selected from the group of aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH$_2$ UTP, 2'NH$_2$ CTP, and 2' F UTP.

In preferred embodiments, modified nucleotide analogs are incorporated into the synthesized siRNA that decrease duplex stability. Modified nucleotide analogs may be incorporated through enzymatic or chemical synthesis. In one preferred embodiment, modified nucleotide analogs are incorporated through enzymatic synthesis. In another preferred embodiment modified nucleotide analogs are incorporated through chemical synthesis siRNA can be introduced into cells in a number of ways. Preferred embodiments include micro-injection, bombardment by particles covered by the siRNA, soaking the cell or organism in a solution of the siRNA, electroporation of cell membranes in the presence of siRNA, liposome-mediated delivery of siRNA and transfection mediated by chemicals such as polyamines, calcium phosphate, viral infection, transformation, and the like. In further preferred embodiments, siRNA is introduced along with components that enhance RNA uptake by the cell, stabilize the annealed strands, or otherwise increase inhibition of the target gene. In a most preferred embodiment, cells are conveniently incubated in a solution containing the siRNA.

In further embodiments, siRNA is delivered to a cell indirectly by introducing one or more vectors that encode both single strands of a siRNA (or, in the case of a self-complementary RNA, the single self-complementary strand) into the cell. The vectors of these embodiments contain elements of the templates described above such that the RNA is transcribed inside the cell, annealed to form siRNA and effects attenuation of the target gene expression. See WO 99/32619, WO 00/44914, WO 01/68836 (each of which is expressly incorporated herein by reference) and references therein for further examples of methods known to the art for introducing siRNA into cells.

Thus, in some embodiments of the present invention, a method for making siRNA of increased potency comprises obtaining nucleotides, and incorporating the nucleotides into siRNA such that an RNA duplex of from 15 to 30 contiguous nucleotides is formed, wherein the siRNA has a sequence that is substantially identical to at least a portion of a selected target gene. In a preferred embodiment, the siRNA is further defined as having reduced duplex stability. In an additional preferred embodiment the siRNA is further defined as comprising obtaining at least one modified nucleotide analog and incorporating the at least one modified nucleotide analog into the siRNA.

In additional, preferred embodiments, the modified nucleotide analog is selected from the group consisting of aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH$_2$ UTP, 2'NH$_2$ CTP, and 2' F UTP.

In another preferred embodiment, the nucleotides or nucleotide analogs may be incorporated into siRNA through enzymatic synthesis. In one embodiment, the nucleotides or nucleotide analogs may be incorporated into siRNA through chemical synthesis.

In some embodiments the invention comprises a method of attenuating the expression of a target gene, the method comprising the steps of:

(a) obtaining a first polynucleotide template comprising a first promoter operatively linked to a first target sequence that has 5' and 3' ends that is substantially identical to at least a portion of the target gene;

(b) obtaining a second polynucleotide template comprising a second promoter operatively linked to a second target sequence that has 5' and 3' ends and substantially the reverse complement of the first target sequence of the first template;

(c) contacting the first template with a reaction mixture comprising an RNA polymerase and nucleotides to transcribe the first template to form a first RNA product;

(d) contacting the second template with a reaction mixture comprising an RNA polymerase and nucleotides to transcribe the second template to form a second RNA product;

(e) annealing the first and second RNA products to form a double stranded RNA product; and (f) introducing the double stranded RNA product into the cell in an amount sufficient to attenuate expression of the target gene.

Other preferred embodiments comprise the steps of:

(a) obtaining a polynucleotide template comprising a promoter operatively linked to a first target sequence, a loop sequence, and a second target sequence having 5' and 3' ends and that is substantially the reverse complement of the first target sequence;

(b) contacting the template with a reaction mixture comprising an RNA polymerase and nucleotides to transcribe the template to form an RNA product; and (c) introducing the RNA product into the cell in an amount sufficient to attenuate expression of the target gene.

In other embodiments a method of attenuating target gene expression comprises the steps of:

(a) obtaining a single-stranded polynucleotide template comprising a target sequence substantially identical to at least a portion of the target gene;

(b) contacting the template with a reaction mixture comprising an RNA replicase and nucleotides to synthesize RNA of a complementary sequence to that of the target sequence so as to form a double stranded RNA product; and (c) introducing the double stranded RNA product into the cell in an amount sufficient to attenuate expression of the target gene.

Additional preferred embodiments comprise the steps of:

(a) obtaining a polynucleotide template comprising a promoter operatively linked to a first target sequence, a loop sequence, and a second target sequence having 5' and 3' ends and that is substantially the reverse complement of the first target sequence;

(b) enzymatically incorporating nucleotides into RNA by contacting the template with a reaction mixture comprising an RNA polymerase and nucleotides to transcribe the template to form an RNA product;

(c) annealing the RNA product to form a stem and loop siRNA product; and (d) introducing the RNA product to a cell comprising a target gene.

Further embodiments comprise the steps of:

(a) obtaining a polynucleotide template comprising a promoter operatively linked to a first target sequence, a loop sequence, and a second target sequence having 5' and 3' ends and that is substantially the reverse complement of the first target sequence;

(b) enzymatically incorporating nucleotides into RNA by contacting the template with a reaction mixture comprising an RNA polymerase and nucleotides to transcribe the template to form an RNA product;

(c) introducing the RNA product to a cell comprising a target gene; and (d) annealing the RNA product to form a stem and loop siRNA product within the cell.

Further preferred embodiments comprise the steps of treating the template nucleotides with an appropriate nuclease, e.g. DNase or similar enzyme, to remove template nucleic acids. Yet another preferred embodiment comprises the steps of treating the enzymatic or chemically synthesized dsRNA with RNases to remove single stranded leader sequences or other, undesired sequences.

Surprisingly and unexpectedly, siRNAs of from 15 to 30 nucleotides in length made through these embodiments of the invention are significantly more potent than siRNAs of the same length made through standard chemical synthesis or without appropriate incorporation of modified nucleotide analogs.

Any of the compositions described herein may be comprised in a kit formulated for performing the methods disclosed. In a non-limiting example the kits may comprise, in suitable container means, a promoter primer, corresponding polymerases, reagents and materials for performing the methods of the invention. In another non-limiting example, the kits may comprise in a suitable container means, modified nucleotide analogs, reagents and materials for incorporation of the modified nucleotide analogs through chemical synthesis means. In a further example, the kits may comprise siRNAs that have incorporated in them modified nucleotide analogs that reduce dsRNA duplex stability.

The kits may comprise compositions of the present invention in suitable aliquots, whether labeled or unlabeled, as may be used to practice the methods of the invention. The components of the kits may be packaged either in aqueous media or in lyophilized form. The container means of the kits will generally include at least one vial, test tube, flask, bottle, syringe or other container means, into which a component may be placed, and preferably, in suitable aliquots. Where there is more than one component in the kit, the kit also will generally contain a second, third or other additional container into which the additional components may be separately placed. However, various combinations of components may be comprised in a vial. Kits may also contain cells in which the expression of target genes is attenuated by the methods of the present invention.

Therapeutic kits of the present invention are kits comprising a promoter, a polymerase, and the reagents, agents, and materials that may be required to practice the methods of the invention, including, but not limited to those reagents necessary for transfection or transformation of cells with siRNA. Such kits may also comprise siRNA made by the methods of the present invention. Such kits will generally contain, in suitable container means, a pharmaceutically acceptable formulation of siRNA made by the methods of the present invention. Such kits may also contain cells in which the expression of target genes is attenuated by the methods of the present invention. The kit may have a single container means, and/or it may have distinct container means for each compound or each reaction mixture or step.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the siRNA or cells in which the expression of target gene or genes is attenuated are placed, preferably, suitably allocated. The kits may also comprise a second container means for containing a sterile, pharmaceutically acceptable buffer and/or other diluent. The kits of the present invention also will typically include a means for containing the materials for practicing the methods of the invention, and any other reagent containers in close confinement for commercial sale. Such containers may include injection or blow-molded plastic containers into which the desired vials are retained. Irrespective of the number or type of containers, the kits of the invention may also comprise, or be packaged with, an instrument for assisting with the injection/administration and/or placement of the ultimate cells in which the expression of a target gene or genes is attenuated within the body of an animal. Such an instrument may be a syringe, pipette, forceps, and/or any such medically approved delivery vehicle.

Following long-standing patent law, the words "a" and "an," when used in conjunction with the word "comprising" in the claims or specification, denotes one or more.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
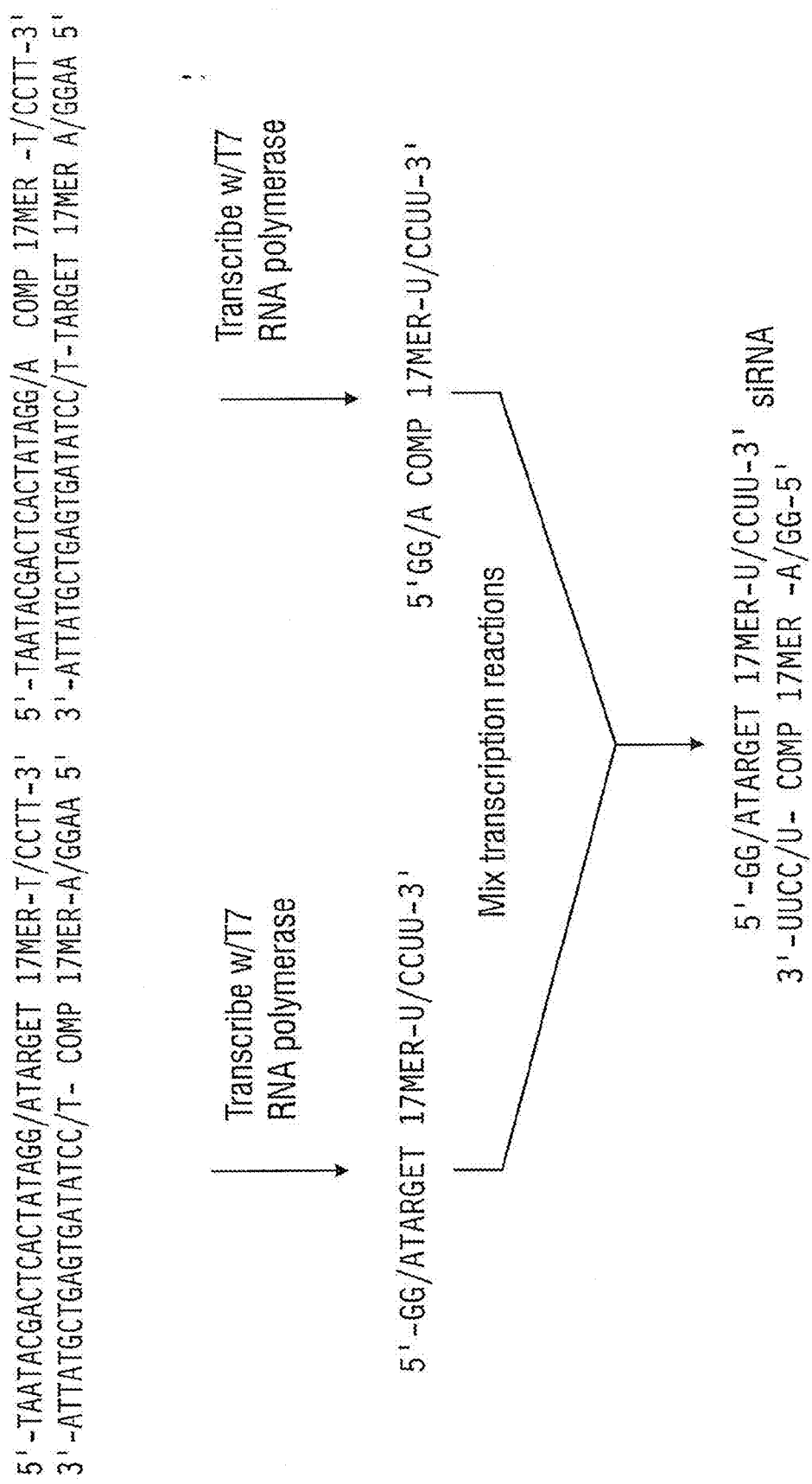
FIG. 1: Production of siRNA by transcription of templates without leader sequences (TAATACGACTCACTATAGG=SEQ ID NO: 35; ATTATGCTGAGTGATATCC=SEQ ID NO: 36).

The present invention provides a method for preparing double-stranded RNA molecules that are of increased potency when used to modulate or attenuate gene expression in cells, tissues, organs, and organisms. The method includes enzymatic polymerization of individual ribonucleotides in a sequence that effectively matches or hybridizes with the nucleotide sequence of a target gene, thereby facilitating the specific modulation of target gene expression. Surprisingly, such enzymatic preparation of dsRNA yields siRNA that is many fold more potent in modulating gene expression than corresponding siRNA prepared through chemical synthesis.

The methods of the present invention therefore provide for much more efficient and cost-effective means for producing and using siRNA in RNA interference applications, which include a wide range of research, industrial, and medical processes, materials, and applications. Medical applications include, by way of example, anti-viral compositions and therapies, anti-tumor compositions and therapies, and compositions and therapies for inherited disorders. One example of the latter application would be the enzymatic synthesis of siRNA for use in therapies to treat autosomal dominant genetic disease such as Huntington's chorea. Additional examples of therapeutic uses include the management of transplant rejection through the treatment of tissues to be introduced into a subject with the siRNAs of the invention in order to modulate or attenuate the expression of genes promoting transplant rejection. For example, hepatocytes may be incubated with enzymatically synthesized siRNA designed to attenuate expression of genes that prompt a host immune response.

The siRNA provided by the present invention allows for the modulation and especially the attenuation of target gene expression when such a gene is present and liable to expression within a cell. Modulation of expression can be partial or complete inhibition of gene function, or even the up-regulation of other, secondary target genes or the enhancement of expression of such genes in response to the inhibition of the primary target gene. Attenuation of gene expression may include the partial or complete suppression or inhibition of gene function, transcript processing or translation of the transcript. In the context of RNA interference, modulation of gene expression is thought to proceed through a complex of proteins and RNA, specifically including small, dsRNA that may act as a "guide" RNA. The siRNA therefore is thought to be effective when its nucleotide sequence sufficiently corresponds to at least part of the nucleotide sequence of the target gene. Although the present invention is not limited by this mechanistic hypothesis, it is highly preferred that the sequence of nucleotides in the siRNA be substantially identical to at least a portion of the target gene sequence.

A target gene generally means a polynucleotide comprising a region that encodes a polypeptide, or a polynucleotide region that regulates replication, transcription or translation or other processes important tot expression of the polypeptide, or a polynucleotide comprising both a region that encodes a polypeptide and a region operably linked thereto that regulates expression. The targeted gene can be chromosomal (genomic) or extrachromosomal. It may be endogenous to the cell, or it may be a foreign gene (a transgene). The foreign gene can be integrated into the host genome, or it may be present on an extrachromosomal genetic construct such as a plasmid or a cosmid. The targeted gene can also be derived from a pathogen, such as a virus, bacterium, fungus or protozoan, which is capable of infecting an organism or cell. Target genes may be viral and pro-viral genes that do not elicit the interferon response, such as retroviral genes. The target gene may be a protein-coding gene or a non-protein coding gene, such as a gene which codes for ribosmal RNAs, splicosomal RNA, tRNAs, etc.

Any gene being expressed in a cell can be targeted. Preferably, a target gene is one involved in or associated with the progression of cellular activities important to disease or of particular interest as a research object. Thus, by way of example, the following are classes of possible target genes that may be used in the methods of the present invention to modulate or attenuate target gene expression: developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), and enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, pectinesterases, peroxidases, phosphatases, phospholipases, phosphorylases, polygalacturonases, proteinases and peptideases, pullanases, recombinases, reverse transcriptases, topoisomerases, xylanases).

The nucleotide sequence of the siRNA is defined by the nucleotide sequence of its target gene. The siRNA contains a nucleotide sequence that is essentially identical to at least a portion of the target gene. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

A siRNA comprises a double stranded structure, the sequence of which is "substantially identical" to at least a portion of the target gene. "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ed., Academic Press, New York, 1993; and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.) and CLUSTAL (Higgins et al., 1992; Thompson, et al., 1994).

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene, although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. SiRNA technology thus has the property of being able to tolerate sequence variations that might be expected to result from genetic mutation, strain polymorphism, or evolutionary divergence.

Alternatively, a siRNA that is "essentially identical to at least a portion of the target gene can be functionally a dsRNA wherein one of the two complementary strands (or, in the case of a self-complementary RNA, one of the two self-complementary portions) is capable of hybridizing with a portion of the target gene transcript (e.g. under conditions including 400 mM NaCl, 40 mM PIPES pH 6.4, 1 mM EDTA, 50 degrees C. or 70 degrees C. hybridization for 12-26 hours; followed by washing).

RNA (ribonucleic acid) is known to be the transcription product of a molecule of DNA (deoxyribonucleic acid) synthesized under the action of an enzyme, DNA-dependent RNA polymerase. There are diverse applications of the obtaining of specific RNA sequences, such as, for example, the synthesis of RNA probes or of oligoribonucleotides (Milligan et al.), or the expression of genes (see, in particular, Steen et al., Fuerst, et al. and Patent Applications WO 91/05, 866 and EP 0,178,863), or alternatively gene amplification as described by Kievits, et al. and Kwoh et al. or in Patent Applications WO 88/10,315 and WO 91/02,818, and U.S. Pat. No. 5,795,715, all of which are expressly incorporated herein by reference.

One of the distinctive features of most DNA-dependent RNA polymerases is that of initiating RNA synthesis according to a DNA template from a particular start site as a result of the recognition of a nucleic acid sequence, termed a promoter, which makes it possible to define the precise localization and the strand on which initiation is to be effected. Contrary to DNA-dependent DNA polymerases, polymerization by DNA-dependent RNA polymerases is not initiated from a 3'-OH end, and their natural substrate is an intact DNA double strand.

Compared to bacterial, eukaryotic or mitochondrial RNA polymerases, phage RNA polymerases are very simple enzymes. Among these, the best known are the RNA polymerases of bacteriophages T7, T3 and SP6. These enzymes are very similar to one another, and are composed of a single subunit of 98 to 100 kDa. Two other phage polymerases share these similarities: that of *Klebsiella* phage K11 and that of phage BA14 (Diaz et al.). Any DNA dependent RNA polymerase is expected to perform in conjunction with a functionally active promoter as desired in the present invention. These include, but are not limited to the above listed polymerases, active mutants thereof, *E. coli* RNA polymerase, and RNA polymerases I, II, and III from a variety of eukaryotic organisms.

Initiation of transcription with T7, SP6 RNA and T3 RNA Polymerases is highly specific for the T7, SP6 and T3 phage promoters, respectively. The properties and utility of these polymerases are well known to the art. Their properties and sources are described in U.S. Pat. Nos. (T7) 5,869,320; 4,952,496; 5,591,601; 6,114,152; (SP6) 5,026,645; (T3) 5,102,802; 5,891,681; 5,824,528; 5,037,745, all of which are expressly incorporated herein by reference.

Reaction conditions for use of these RNA polymerases are well known in the art, and are exemplified by those conditions provided in the examples and references. The result of contacting the appropriate template with an appropriate polymerase is the synthesis of an RNA product, which is typically single-stranded. Although under appropriate conditions, double stranded RNA may be made from a double stranded DNA template. See U.S. Pat. No. 5,795,715, incorporated herein by reference. The process of sequence specific synthesis may also be known as transcription, and the product the transcript, whether the product represents an entire, functional gene product or not.

dsRNA for use as siRNA may also be enzymatically synthesized through the use of RNA dependent RNA polymerases such as Q beta replicase, Tobacco mosaic virus replicase, brome mosaic virus replicase, potato virus replicase, etc. Reaction conditions for use of these RNA polymerases are well known in the art, and are exemplified by those conditions provided in the examples and references. Also see U.S. Pat. No. RE35,443, and U.S. Pat. No. 4,786,600, both of which are incorporated herein by reference. The result of contacting the appropriate template with an appropriate polymerase is the synthesis of an RNA product, which is typically double-stranded. Employing these RNA dependent RNA polymerases therefore may utilize a single stranded RNA or single stranded DNA template. If utilizing a single stranded DNA template, the enzymatic synthesis results in a hybrid RNA/DNA duplex that is also contemplated as useful as siRNA.

The templates for enzymatic synthesis of siRNA are nucleic acids, typically, though not exclusively DNA. A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells (see for example, Sambrook, 2001, incorporated herein by reference).

A nucleic acid may be purified on polyacrylamide gels, cesium chloride centrifugation gradients, or by any other means known to one of ordinary skill in the art (see for example, Sambrook (2001), incorporated herein by reference).

The term "nucleic acid" will generally refer to at least one molecule or strand of DNA, RNA or a derivative or mimic thereof, comprising at least one nucleotide base, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the terms "oligonucleotide" and "polynucleotide." These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

As will be appreciated by one of skill in the art, the useful form of nucleotide or modified nucleotide to be incorporated will be dictated largely by the nature of the synthesis to be performed. Thus, for example, enzymatic synthesis typically utilizes the free form of nucleotides and nucleotide analogs, typically represented as nucleotide triphospates, or NTPs. These forms thus include, but are not limited to aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH$_2$ UTP, 2'NH$_2$ CTP, and 2' F UTP. As will also be appreciated by one of skill in the art, the useful form of nucleotide for chemical syntheses may be typically represented as aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH$_2$ uridine, 2'NH$_2$ cytidine, and 2' F uridine. In the present invention, the listing of either form is non-limiting in that the choice of nucleotide form will be dictated by the nature of the synthesis to be performed. In the present invention, then, the inventors use the terms aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH$_2$ uridine, 2'NH$_2$ cytidine, and 2' F uridine generically to refer to the appropriate nucleotide or modified nucleotide, including the free phosphate (NTP) forms as well as all other useful forms of the nucleotides.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a nucleic acid, and/or encodes a polypeptide or peptide-coding sequences of a gene that is defective or mutated in a hematopoietic and lympho-hematopoietic disorder. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit.

As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

$$n \text{ to } n+y$$

where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended protocol.

To obtain the RNA corresponding to a given template sequence through the action of an RNA polymerase, it is necessary to place the target sequence under the control of the promoter recognized by the RNA polymerase.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and synthesis of the RNA.

The spacing between promoter elements frequently is flexible, so that promoter function is preserved when elements are inverted or moved relative to one another. The spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

T7, T3, or SP6 RNA polymerases display a high fidelity to their respective promoters. The natural promoters specific for the RNA polymerases of phages T7, T3 and SP6 are well known. Furthermore, consensus sequences of promoters are known to be functional as promoters for these polymerases. The bacteriophage promoters for T7, T3, and SP6 consist of 23 bp numbered −17 to +6, where +1 indicates the first base of the coded transcript. An important observation is that, of the +1 through +6 bases, only the base composition of +1 and +2 are critical and must be a G and purine, respectively, to yield an efficient transcription template. In addition, synthetic oligonucleotide templates only need to be double-stranded in the −17 to −1 region of the promoter, and the coding region can be all single-stranded. (See Milligan et al.) This can reduce the cost of synthetic templates, since the coding region (i.e., from +1 on) can be left single-stranded and the short oligonucleotides required to render the promoter region double-stranded can be used with multiple templates. A further discussion of consensus promoters and a source of naturally occurring bacteriophage promoters is U.S. Pat. No. 5,891,681, specifically incorporated herein by reference.

Use of a T7, T3 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Figure 2:
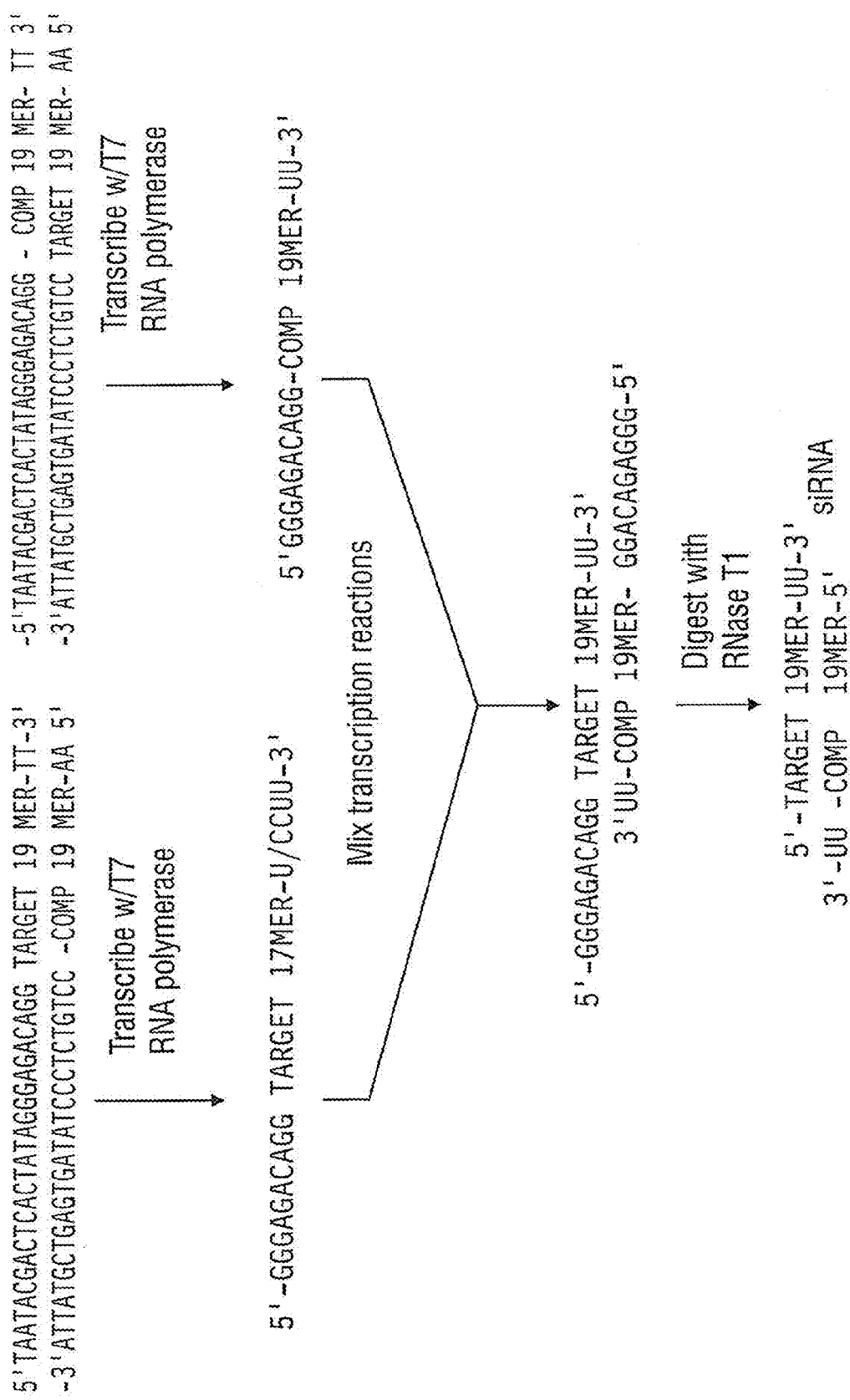
FIG. 2: Production of siRNA by transcription of templates with leader sequences and subsequent digestion by RNase T1 (TAATACGACTCACTATAGGGAGACAGG=SEQ ID NO: 39; ATTATGCTGAGTGATATCCCTCTGTCC=SEQ. ID NO: 40; GGGAGACAGG=SEQ ID NO: 1; GGACAGAGGG=SEQ ID NO: 41).
Figure 3:
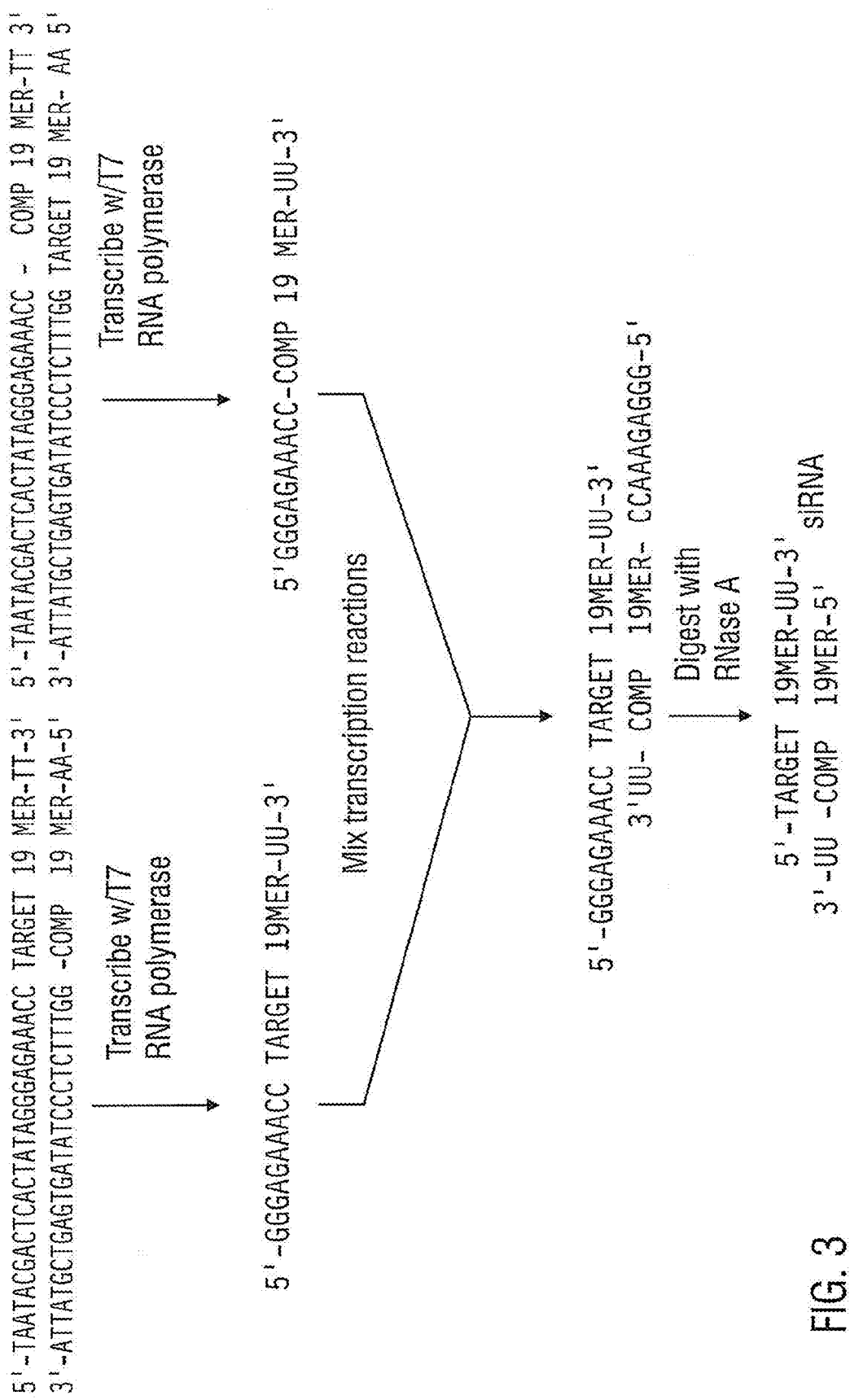
FIG. 3: Production of siRNA by transcription of templates with leader sequences and subsequent digestion with RNase A (TAATACGACTCACTATAGGGAGAAACC=SEQ ID NO: 37; ATTATGCTGAGTGATATCCCTCTTTGG=SEQ ID NO: 38; GGGAGAAACC=SEQ ID NO: 2; CCAAAGAGGG=SEQ ID NO: 42).
Figure 4:
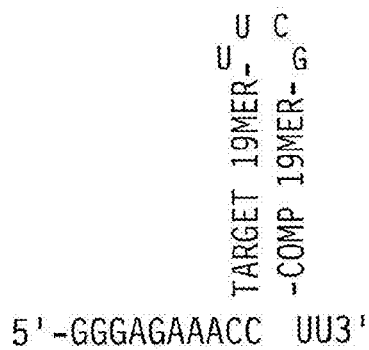
FIG. 4: Production of siRNA by transcription of templates encoding hairpin structures (TAATACGACTCACTATAGGGAGAAACC=SEQ ID NO: 37; ATTATGCTGAGTGATATCCCTCTTTGG=SEQ ID NO: 38; GGGAGAAACC=SEQ ID NO: 2; CCAAAGAGGG=SEQ ID NO: 42).
Figure 4:
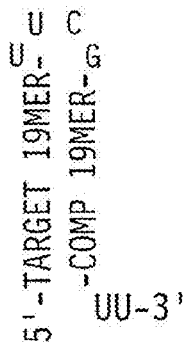

When made in vitro, siRNA is formed from one or more strands of polymerized ribonucleotide. When formed of only one strand, it takes the form of a self-complementary hairpin-type or stem and loop structure that doubles back on itself to form a partial duplex. The self-duplexed portion of the RNA molecule may be referred to as the "stem" and the remaining, connecting single stranded portion referred to as the "loop" of the stem and loop structure (FIG. 4). When made of two strands, they are substantially complementary (FIGS. 1, 2, and 3).

The cell containing the target gene may be derived from or contained in any organism (e.g. plant, animal, protozoan, virus, bacterium, or fungus). The plant may be a monocot, dicot or gynmosperm; the animal may be a vertebrate or invertebrate. Preferred microbes are those used in agriculture or by industry, and those that a pathogenic for plants or animals. Fungi include organisms in both the mold and yeast morphologies. Examples of vertebrates include fish and mammals, including cattle, goat, pig, sheep, hamster, mouse, rate and human; invertebrate animals include nematodes, insects, arachnids, and other arthropods. Preferably, the cell is a vertebrate cell. More preferably, the cell is a mammalian cell.

The cell having the target gene may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus encompasses fetal tissue. The cell having the target gene may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells, of the endocrine or exocrine glands.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding such an RNA has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, CD34+ cells CD4+ cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes.

In certain embodiments, the host cell or tissue may be comprised in at least one organism. In certain embodiments, the organism may be, human, primate or murine. In other embodiments the organism may be any eukaryote or even a prokayrote (e.g., a eubacteria, an archaea), as would be understood by one of ordinary skill in the art. One of skill in the art would further understand the conditions under which to incubate all of the above described host cells to maintain them and to permit their division to form progeny.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methodology Employed in Examples 1-5

A. Cell Proliferation Assays.

Transfected HeLa cells were analyzed using Alamar Blue (BioSource International, Inc., CA) at 24 hr intervals. Alamar Blue is a compound, that when reduced by cellular metabolism, changes from a non-fluorescent blue color to a fluorescent red form that is easily quantified. The amount of Alamar Blue reduced is directly proportional to the cell number, providing a rapid method for assessing cell proliferation. To perform the assay, the Alamar Blue reagent was added into the tissue culture media at a 10% final concentration. The mixture was incubated for 3-6 hr in growth conditions after which fluorescence was quantified using a Spectra Max™ GeminiXS™ (Molecular Devices, Sunnyvale, Calif.).

B. Immunofluorescence.

HeLa cells used for immunofluorescence were grown on chamber slides in DMEM/10% FBS and transfected with the siRNAs, buffer, or phosphorothioate oligonucleotides. 48 hr after transfection, the cells were fixed with 4% paraformaldehyde/PBS. Cells were permeabilized by exposure to 0.1% Triton X-100/PBS for 5 min and then incubated with 3% BSA in PBS for 1 hr. After incubating with a mouse anti-myc monoclonal antibody (Neomarkers) at a 1:200 dilution in PBS, the cells were washed briefly with PBS, incubated with fluorescein-conjugated goat anti-mouse IgG (Jackson ImmunoResearch Laboratories). The cells were mounted with Vectashield™ (Vector Laboratories). Images were analyzed using an Olympus BX60™ microscope and acquired with the help of a Hitachi KP-c571™ camera and Adobe® Photoshop®.

C. Transfection of HeLa Cells with siRNAs.

Hela S3 cells @ $5 \times 10^3$ cells/well were plated in complete medium w/out antibiotics. The cells were incubated overnight @ 37° C. in a humidified 5% $CO_2$ incubator. Chemically synthesized siRNA stocks were diluted into 40 ul Opti-MEM™ (Invitrogen) to indicated final concentrations in 250 ul total volume per well. Enzymatically synthesized siRNA stocks were diluted into 40 ul Opti-MEM™ to indicated final concentrations in 250 ul total volume per well.

For transfections, 1.5 ul of Oligofectamine™ (Invitrogen) was added to 6 ul of OptiMEM™ for each well being transfected. The mixture was incubated at room temperature for 5-10 min. The diluted Oligofectamine™ was added to prepared siRNAs, mixed gently, and incubated at RT for 15-20 min. The cell medium was aspirated, and 200 ul fresh growth medium was added to each well. The medium was mixed gently, and then overlaid with ~50 ul of the appropriate siRNA/oligofectamine complex. The transfected cells were incubated at 37° C. in a humidified 5% $CO_2$ incubator.

D. Direct Recovery of siRNAs.

To prepare chemically or enzymatically produced siRNAs for transfection, they must be purified from accompanying salts, proteins, and non-dsRNA nucleic acids. The hybridization, transcription, or nuclease digestion reactions used to produce siRNAs can be phenol extracted with 2× volumes of buffered phenol, extracted with 2× volumes of ether or chloroform, and precipitated by adding $NH_4OAc$ to a final concentration of 0.5 M and 2× volumes of ethanol. The siRNA is recovered by centrifuging at 13,200 RPM. The siRNA pellet is washed one time with 70% ethanol.

E. Gel Purification of siRNAs.

To gel purify siRNAs, 10 μl of 50% sucrose/0.25% bromophenol blue is added to the hybridization, transcription, or nuclease digestion reaction. The sample is loaded on a 12% polyacrylamide gel and electrophoresed at 250 volts for one hour. The siRNA is detected by UV shadowing (Sambrook 2001). The product band is excised from the gel, transferred to a microfuge tube with 400 μl of 2 mM EDTA, and incubated overnight at 37° C. The siRNA is recovered by transferring the solution to a new microfuge tube, adding $NH_4OAc$ to a final concentration of 0.5 M, adding 2× volumes of ethanol, incubating at −20° C. for fifteen minutes, and centrifuging at 13,200 RPM for fifteen minutes. The siRNA pellet is washed 1× with 70% ethanol and then dried.

F. Column Purification of siRNAs.

400 μl of 1.2× Binding Buffer (625 mM NaCl, 62.5% EtOH) is added to hybridization, transcription, or nuclease-digestion reaction. A glass fiber filter in a column is equilibrated with 400 μl of 1× Binding Buffer (500 mM NaCl, 50% EtOH). The siRNA/binding buffer mixture is added to the pre-wet column and spun at 13,200 RPM for 2 minutes. The column is washed 2× with 500 μl of 1× Binding Buffer. 100 of nuclease-free water pre-heated to 75° C. is added to the column and incubated for two minutes. The column is spun at 13,200 RPM for 2 minutes. SiRNA is in the elute.

G. RNAse Digestion.

In cases where a leader sequence is used to improve the yield of siRNAs and reduce template constraints, the following nuclease digestion step is employed to remove a non-homologous leader sequence and non-hybridized RNAs. Add 50 μl of nuclease free water, 6 μl of 10× Nuclease buffer (100 mM Tri pH 7.5, 25 mM $MgCl_2$, 1 mM $CaCl_2$), and 10 U of RNase A or 10,000 U of RNase T1, or similar unit activity of RNase Sa. Incubate for thirty minutes at room temperature.

Leader sequence used may dictate which of the nucleases to use. Single strand specific Rnases are preferred. Thus, RNase T1 preferentially digests single-stranded RNA at G residues. RNase A preferentially digests at C and U residues. If RNase T1 is to be used, the last nucleotide in the leader sequence is preferred to be a G to eliminate the entire leader sequence from the siRNA Likewise, if RNase A is to be used, the last nucleotide in the leader sequence should be a C or U. Additionally, RNase Sa, RNase Sa2, or RNase Sa3, whose use and properties are well known to those of skill in the art, may be employed to digest the leader sequences. See Hebert et al. (1997) and Pace et al. (1998), both of which are expressly incorporated herein by reference.

H. T7 RNA Polymerase

T7 RNA Polymerase is used as a preparation that includes 200 U/ul of T7 RNA Polymerase, Inorganic Pyrophosphatase (IPP) 0.05 U/ul, Placental Ribonuclease Inhibitor (Sambrook 2001) 0.3 U/ul, Superasin™ (Ambion) 2 U/ul, and 1% chaps.

Example 1

Model Target Genes

C-myc and GAPDH were chosen to evaluate the impact of siRNA on the expression of genes in mammalian cells. The c-myc proto-oncogene can be a transcription repressor and activator and has important roles in cell death and cell cycle progression (reviewed in Ryan et al., 1996). GAPDH is the metabolic protein Glyceraldehyde-3-phosphate Dehydrogenase. It is involved in glycolysis. Reducing the expression of either gene slows the cell division rate, which can be tracked using the Alomar Blue assay described above or by quantifying the number of healthy cells. In addition, the abundance of the mRNA and protein from each gene can be calculated using standard techniques (RT-PCR, Northern analysis, immunofluorescence, or Western analysis).

Example 2

SiRNA Target Site Selection

Four different double-stranded 21mer siRNAs were designed and prepared for both c-myc and GAPDH. These siRNAs were tested to determine which siRNA provided the greatest effect without affecting non-target genes.

c-myc siRNA Development

Figure 5:
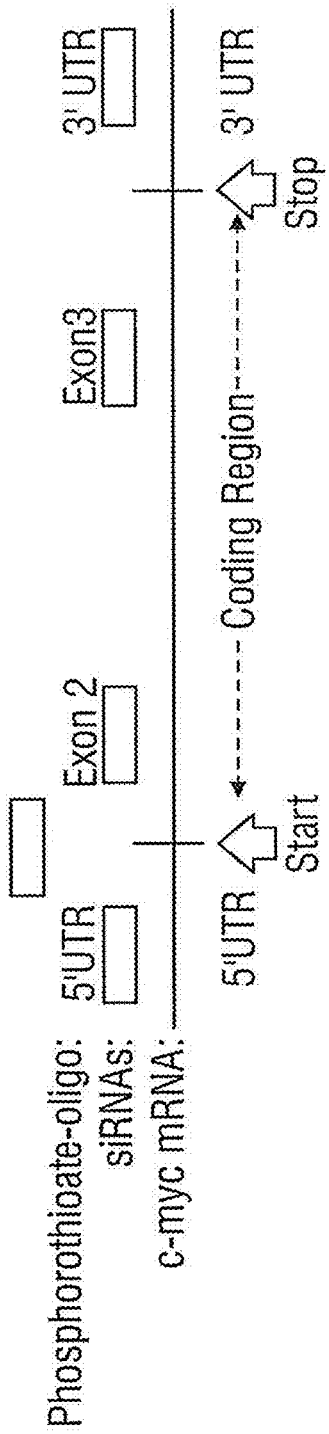
FIG. 5: c-myc mRNA transcript organization. The locations of siRNAs made are indicated by the boxes above the line representing the transcript.

The siRNAs specific to different regions of the c-myc gene are listed in Table 1 (SEQ ID NOS: 3-10) and diagrammed in FIG. 5. Also shown are the locations of the start codon (start), stop codon (stop), coding region, 5' and 3' UTR's as well as the binding site of a well-characterized antisense oligonucleotide. The antisense oligonucleotide that we used has previously been shown to reduce c-myc expression (Kimura et al., 1995) and served as a positive control in our experiments.

1.5 nanomoles of the sense and anti-sense siRNAs were mixed in a solution comprising 100 mM KOAc, 30 mM HEPES-KOH pH 7.4, and 2 mM MgOAc. The solutions were incubated at 37° C. for one minute, then at room temperature for one hour. The samples were evaluated by non-denaturing 12% PAGE to confirm that the majority of the RNA was double-stranded. The siRNAs were then kept in aliquots at −20° C. until they were transfected.

Figure 6:
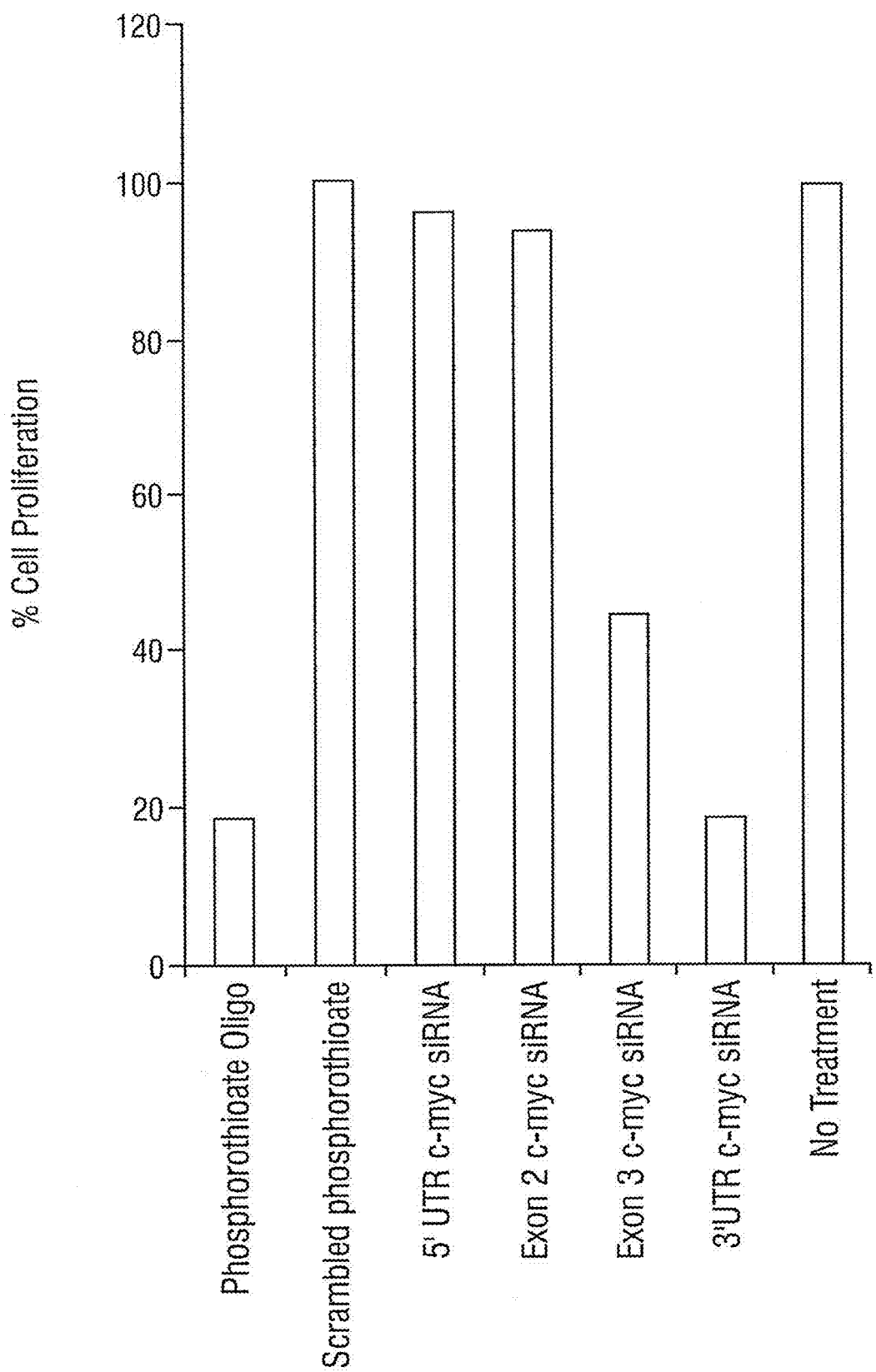
FIG. 6: Relative cell proliferation (as compared to a buffer-transfected control) of HeLa cells transfected with the various siRNAs to c-myc, as well as with the optimized antisense oligonucleotide, 48 hr after transfection.

HeLa cells were transfected with 100 nM of the siRNAs and the antisense oligonucleotide. Since reduction in c-myc expression levels can lead to a reduction in cell division rates, cell proliferation was monitored at 24 hr intervals following transfection. Differences in proliferation rates were first noted 48 hr after the HeLa cells had been transfected with the siRNAs. FIG. 6 depicts the relative cell proliferation (as compared to a buffer-transfected control) of HeLa cells transfected with the various siRNAs, as well as with the optimized antisense oligonucleotide, 48 hr after transfection. The data demonstrate that siRNAs to different regions of the mRNA have variable effects on cell proliferation.

TABLE 1

| Name | RNA Sequence (5' to 3') | SEQ ID NO: |
|---|---|---|
| 5' UTR sense | GGGAGAUCCGGAGCGAAUAdTdT | 3 |
| 5' UTR anti-sense | UAUUCGCUCCGGAUCUCCCdTdT | 4 |
| Exon 2 sense | CUUCUACCAGCAGCAGCAGdTdT | 5 |
| Exon 2 anti-sense | CUGCUGCUGCUGGUAGAAGdTdT | 6 |
| Exon 3 sense | CACACAACGUCUUGGAGCGdTdT | 7 |
| Exon 3 antisense | CGCUCCAAGACGUUGUGUGdTdT | 8 |
| 3' UTR sense | CGAUUCCUUCUAACAGAAAdTdT | 9 |
| 3' UTR anti-sense | UUUCUGUUAGAAGGAAUCGdTdT | 10 |
| Scrambled sense | GCGACGUUCCUGAAACCACdTdT | 11 |
| Scrambled antisense | GUGGUUUCAGGAACGUCGCdTdT | 12 |

The reduction in cell proliferation observed with the siRNA to the 3' UTR was similar to that found using the optimized antisense phosphorothioate oligonucleotide complementary to the start codon of the c-myc mRNA (Kimura et al., 1995). In contrast, siRNAs against the 5' UTR and Exon 2 of the c-myc mRNA affected cell proliferation similarly to the scrambled siRNA sequence, which was used as a negative control (FIG. 6). All of the transfections and cell proliferation assays were reproduced in independent experiments and the differences in cell proliferation rates were shown to be statistically significant.

Figure 7:
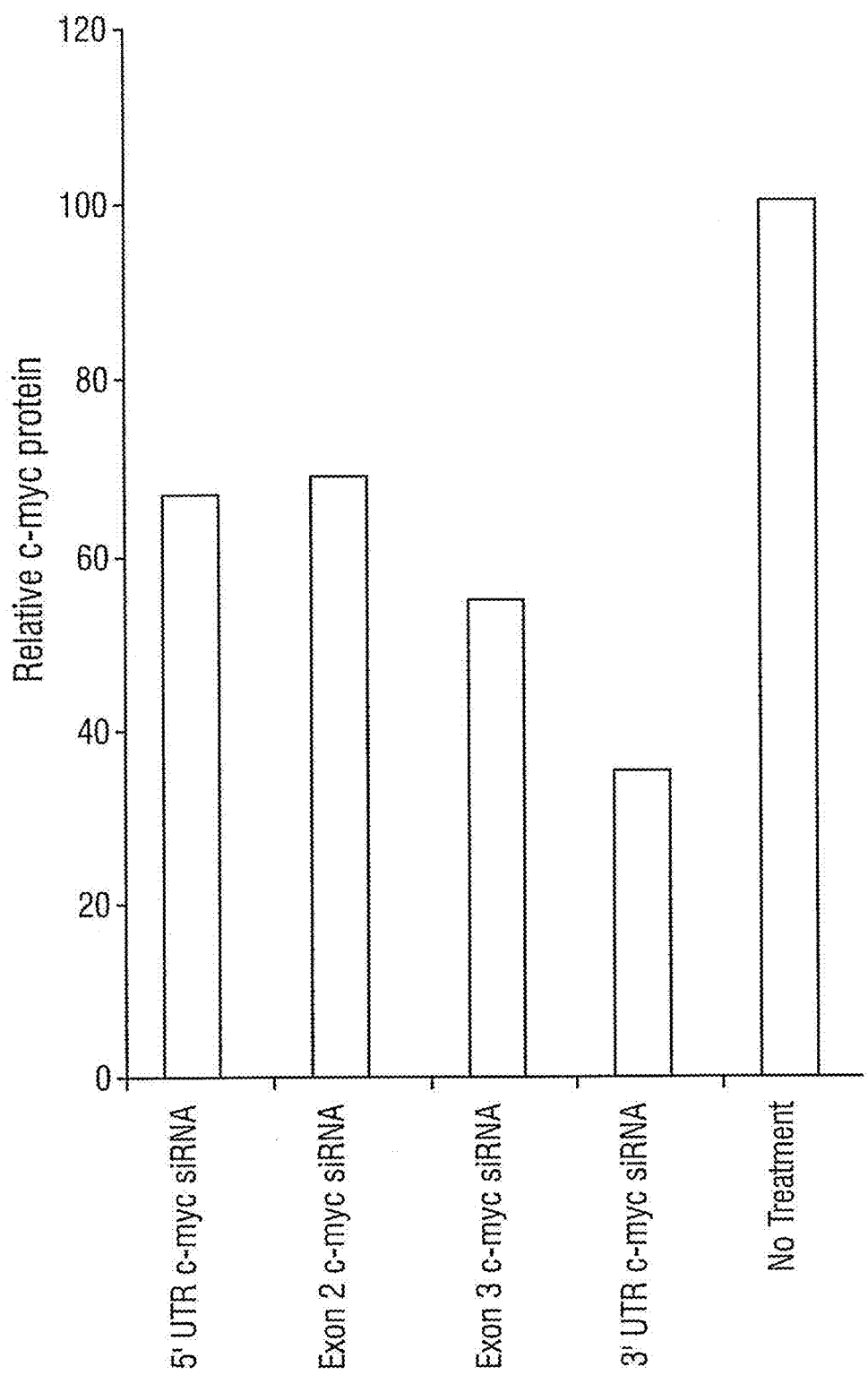
FIG. 7: Immunofluorescence experiments using an anti-myc antibody were used to measure c-myc protein levels to confirm that siRNAs were reducing expression of c-myc.
Figure 8:
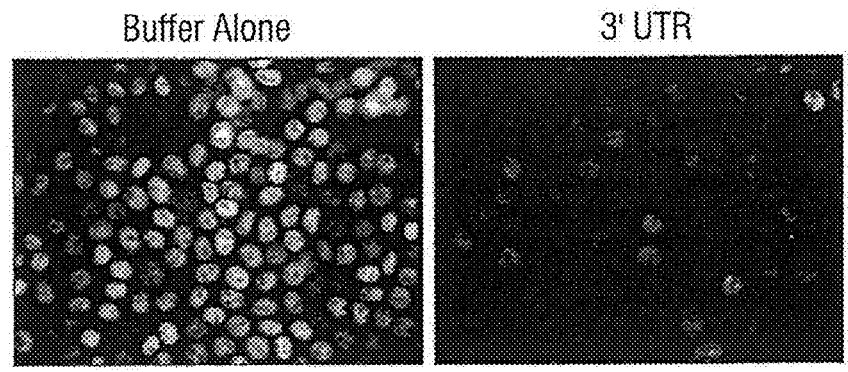
FIG. 8: The siRNA against the 3' UTR leads to a drastic reduction in c-myc protein levels.

Immunofluorescence experiments using an anti-myc antibody were used to measure c-myc protein levels to confirm that siRNAs were reducing expression of c-myc (FIG. 7). As with the cell proliferation assay, the siRNA corresponding to the 3' UTR induced the greatest reduction in fluorescence (FIG. 7), indicating the lowest levels of protein. A representative example of the immunofluorescence data for c-myc protein levels is shown in FIG. 8. These data clearly demonstrate that the siRNA against the 3' UTR leads to a drastic reduction in c-myc protein levels. The amount of fluorescence detected for the 3' UTR sample was nearly equivalent to that observed for the "secondary antibody-only" control and no change in GAPDH protein levels was detected after transfection with any of the siRNAs complementary to the c-myc mRNA (data not shown), indicating that the antiviral response pathway was not induced. The 3' UTR specific c-myc siRNA was selected for subsequent studies.

GAPDH siRNA Development

The siRNAs specific to different regions of the GAPDH gene are listed in Table 2 (SEQ ID NOS: 14-21) The four siRNAs were prepared from DNA oligonucleotides using in vitro transcription with T7 RNA polymerase.

TABLE 2

| Name | RNA Sequence (5' to 3') | SEQ ID NO: |
|---|---|---|
| 5' GAPDH sense | UGAUGGCAACAAUAUCCACdTdT | 13 |
| 5' GAPDH anti-sense | GUGGAUAUUGAAGCCAUCAdTdT | 14 |
| 5' Medial GAPDH sense | AAAGUUGUCAUGGAUGACCdTdT | 15 |
| 5' Medial GAPDH anti-sense | GGUCAUCCAUGACAACUUUdTdT | 16 |
| 3' Medial GAPDH sense | GAAGGCCAUGCCAGUGAGCdTdT | 17 |
| 3' Medial GAPDH antisense | GCUCACUGGCAUGGCCUUCdTdT | 18 |
| 3' GAPDH sense | CAUGAGGUCCACCACCCUGdTdT | 19 |
| 3' GAPDH anti-sense | CAGGGUGGUGGACCUCAUGdTdT | 20 |

The following synthetic DNA oligomers were purchased from Integrated DNA Technologies:

TABLE 3

| Name | DNA Sequence (5' to 3') | SEQ ID NO: |
|---|---|---|
| T7 Promoter Primer: | GGTAATACGACTCACTATAGGGAGACAGG | 21 |
| 5' GAPDH sense: | AAGTGGATATTGTTGCCATCACCTGTCTC | 22 |
| 5' GAPDH antisense: | AATGATGGCAACAATATCCACCCTGTCTC | 23 |

TABLE 3-continued

| Name | DNA Sequence (5' to 3') | SEQ ID NO: |
|---|---|---|
| 5' Medial GAPDH sense | AAGGTCATCCATGACAACTTTCCTGTCTC | 24 |
| 5' Medial GAPDH antisense | AAAAAGTTGTCATGGATGACCCCTGTCTC | 25 |
| 3' Medial GAPDH sense | AAGCTTCACTGGCATGGCCTTCCTGTCTC | 26 |
| 3' Medial GAPDH antisense | AAGAAGGCCATGCCAGTGAGCCCTGTCTC | 27 |
| 3' GAPDH sense | AACAGGGTGGTGGACCTCATGCCTGTCTC | 28 |
| 3' GAPDH antisense | AACATGAGGTCCACCACCCTGCCTGTCTC | 29 |

In separate reactions, the T7 promoter primer was mixed with each of the sense and antisense templates in separate reactions and converted to transcription templates. Templates for in vitro transcription may be double-stranded over the length of the promoter sequence (Milligan et al. 1987). Making the entire template double-stranded improves the transcription of siRNAs, therefore the following procedure is used to convert DNA oligonucleotides to transcription templates for siRNA synthesis.

The DNA templates were diluted to 100 µM in nuclease-free water. 2 µl of each DNA template was mixed with 2 µl of 100 µM Promoter Primer and 6 µl of Hybridization Buffer (20 mM Tris pH 7.0, 100 mM KCl, 1 mM EDTA). The oligonucleotide mixtures were heated to 70° C. for five minutes, then incubate at 37° C. for five minutes. 2 µl of 10× reaction Buffer (150 mM Tris pH 7.0, 850 mM KCl, 50 mM MgCl$_2$, 50 mM (NH$_4$)$_2$SO$_4$), 2 µl of 10 dNTP mix (2.5 mM dATP, 2.5 mM dCTP, 2.5 mM dGTP, and 2.5 mM dTTP), 4 µl of water, and 2 µl of 5 U/ml klenow DNA polymerase was added to each oligonucleotide mixture. The reaction was incubated at 37° C. for thirty minutes.

The templates were transcribed using T7 RNA polymerase by mixing together the following: 2 µl siRNA DNA Template; 2 µl 75 mM ATP; 2 µl 75 mM CTP; 2 µl 75 mM GTP; 2 µl 75 mM UTP; 2 µl 10× Transcription Buffer (400 mM Tris pH 8.0, 240 mM MgCl$_2$, 20 mM Spermidine, 100 mM DTT); 6 µl Nuclease-Free Water; and 2 µl T7 RNA Polymerase (T7 RNA Polymerase-200 U/ul, Inorganic Pyrophosphatase (IPP) 0.05 U/ul, RNase Inhibitor 0.3 U/ul, Superasin 2 U/ul, 1% chaps).

This reaction mix was incubated for two to four hours at 37° C. The RNA products were then mixed and incubated overnight at 37° C. to facilitate annealing of the complementary strands of the siRNAs. The leader sequences were removed by treatment with RNase T1 and the resulting siRNAs were gel purified.

Figure 9:
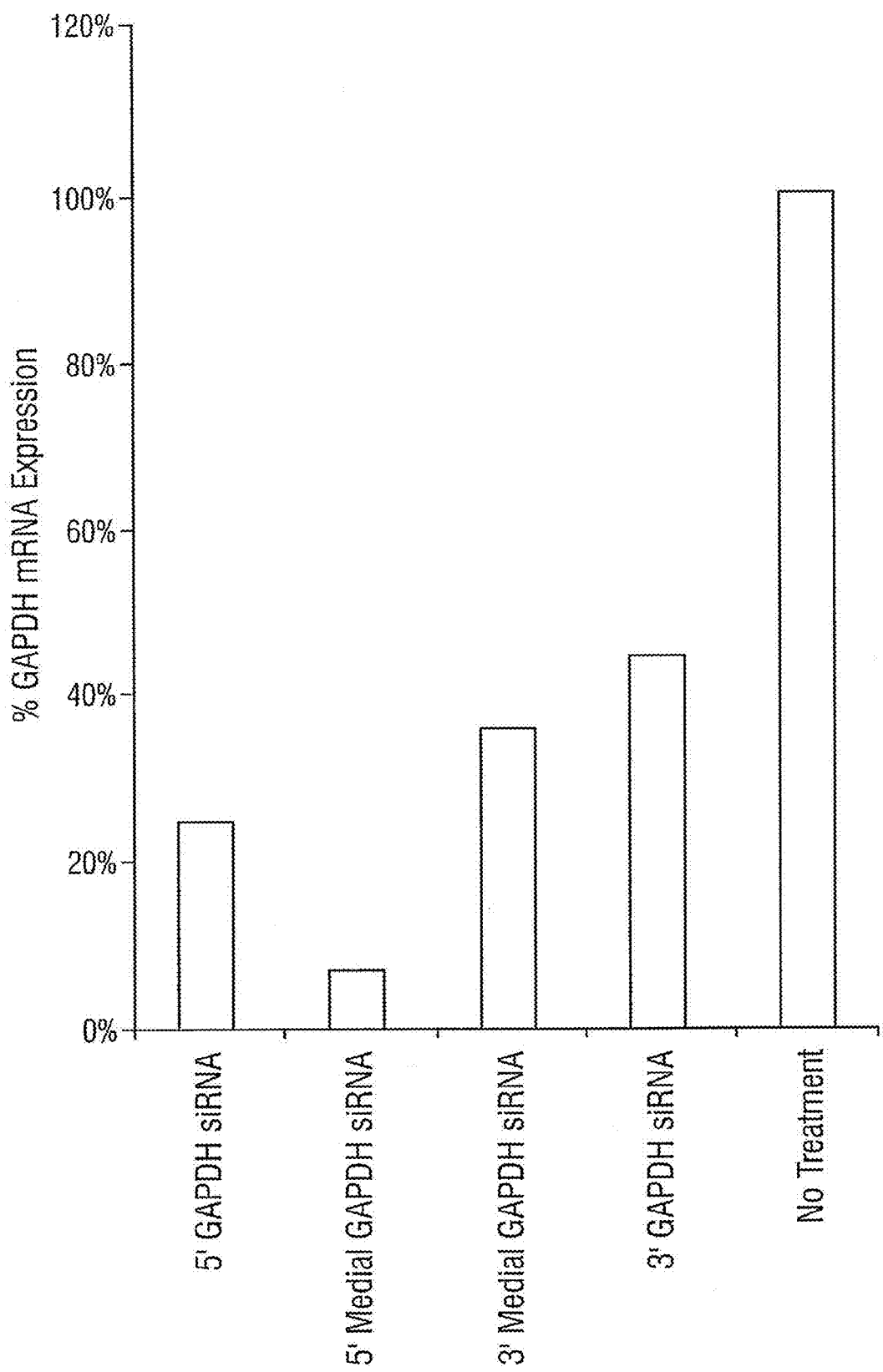
FIG. 9: Relative reduction in GAPDH mRNA levels in siRNA transfected cells versus untreated cells.

HeLa cells were transfected with 10 nM of each of the GAPDH-specific siRNAs. 48 hours after transfection, the cells were harvested and RNA was isolated using the RNAquesous kit (Ambion). Equal amounts of the RNA samples were fractionated by agarose gel electrophoresis and transferred to positively charged nylon membranes using the NorthernMax-Gly kit (Ambion). The Northern blots were probed for GAPDH, cyclophilin, and 28s rRNA using the reagents and protocols of the NorthernMax-Gly kit. The Northern blots were exposed to a phosphorimager screen and quantified using the Molecular Analyst (BioRad). The relative reduction in GAPDH mRNA levels in siRNA transfected cells versus untreated cells is provided in FIG. 9. For GAPDH, the 5' Medial siRNA provided the greatest level of gene silencing and was selected for subsequent evaluation.

Example 3

Potency of Chemical Versus Enzymatic Synthesis of siRNA-c-myc

The 3' UTR siRNA described above was produced by in vitro transcription to compare the potency of siRNAs prepared by enzymatic means to siRNAs generated by chemical synthesis. The following synthetic DNA oligomers were purchased from Integrated DNA Technologies:

TABLE 4

| Name | DNA Sequence (5' to 3') | SEQ ID NO: |
|---|---|---|
| T7 Promoter Primer: | GGTAATACGACTCACTATAGGGAGACAGG | 30 |
| 3' UTR sense: | AATTTCTGTTAGAAGGAATCGCCTGTCTC | 31 |
| 3' UTR antisense: | AACGATTCCTTCTAACAGAAACCTGTCTC | 32 |

The T7 promoter primer was mixed with the 3' UTR sense and antisense templates in separate reactions and converted to transcription templates. Templates for in vitro transcription may be double-stranded over the length of the promoter sequence (Milligan et al. 1987). Making the entire template double-stranded improves the transcription of siRNAs, therefore the following procedure is used to convert DNA oligonucleotides to transcription templates for siRNA synthesis.

The DNA templates were diluted to 100 µM in nuclease-free water. 2 µl of each DNA template was mixed with 2 µl of 100 µM Promoter Primer and 6 µl of Hybridization Buffer (20 mM Tris pH 7.0, 100 mM KCl, 1 mM EDTA). The oligonucleotide mixtures were heated to 70° C. for five minutes, then incubated at 37° C. for five minutes. 2 µl of 10× reaction Buffer (150 mM Tris pH 7.0, 850 mM KCl, 50 mM $MgCl_2$, 50 mM $(NH_4)_2SO_4$), 2 µl of 10 dNTP mix (2.5 mM dATP, 2.5 mM dCTP, 2.5 mM dGTP, and 2.5 mM dTTP), 4 µl of water, and 2 µl of 5 U/ml klenow DNA polymerase was added to each oligonucleotide mixture. The reaction was incubated at 37° C. for thirty minutes.

The templates were transcribed using T7 RNA polymerase by mixing together the following: 2 µl siRNA DNA Template; 2 µl 75 mM ATP; 2 µl 75 mM CTP; 2 µl 75 mM GTP; 2 µl 75 mM UTP; 2 µl 10× Transcription Buffer (400 mM Tris pH 8.0, 240 mM $MgCl_2$, 20 mM Spermidine, 100 mM DTT); 6 µl Nuclease-Free Water; and 2 µl T7 RNA Polymerase (T7 RNA Polymerase-200 U/ul, Inorganic Pyrophosphatase (IPP) 0.05 U/ul, RNase Inhibitor 0.3 U/ul, Superasin 2 U/ul, 1% chaps).

This reaction mix was incubated for two to four hours at 37° C. The RNA products were then mixed and incubated overnight at 37° C. to facilitate annealing to form siRNA. The leader sequences were removed by digestion with RNase T1. The resulting siRNA was then gel purified.

Figure 10:
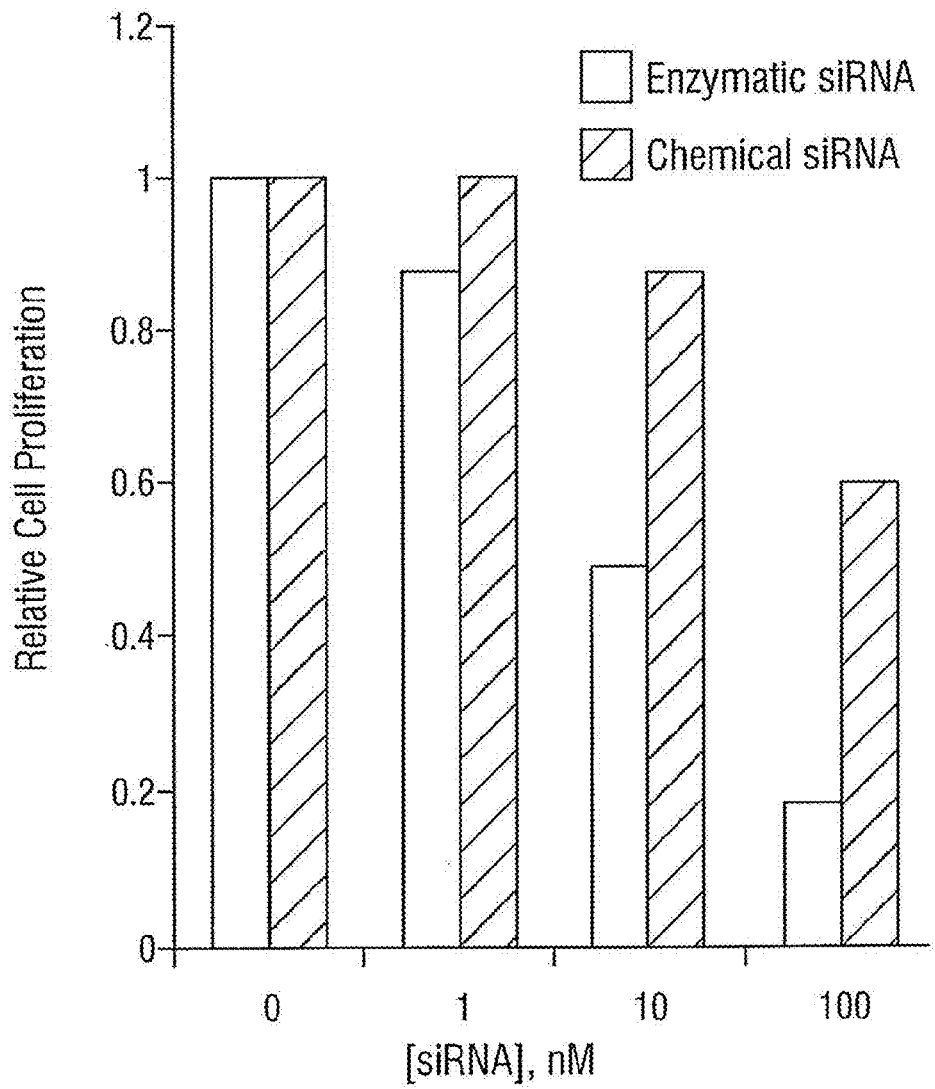
FIG. 10: Comparison of siRNA effectiveness between enzymatically synthesized and siRNA made through standard chemical synthesis in attenuation of c-myc mediated cell proliferation.

Different molar amounts of in vitro transcribed and chemically synthesized siRNAs specific to the 3' UTR of the c-myc mRNA were transfected into HeLa S3 cells. The HeLa S3 cells were evaluated for proliferation using Alamar Blue (BioSource International, Inc., CA) at 72 hrs post-transfection. The in vitro transcribed siRNAs at a concentration of 10 nM reduced cell proliferation by greater than 50% (FIG. 10). In contrast, synthetic siRNA to the same target sequence at a concentration of 100 nM reduced proliferation by only 40% (FIG. 10). The experiment was done in triplicate and has been repeated many times with identical results.

The in vitro transcribed and chemically synthesized siRNAs were quantified by both the Picogreen Assay (Molecular Probes) and by measuring the absorbance of the samples at 260 nm (Sambrook 2001). Both methods confirmed the concentrations of the siRNAs, supporting our conclusion that our preparative procedure yields siRNAs that are at least ten-fold more potent than siRNAs prepared by standard methods.

To rule out the possibility that purification procedures were providing an advantage to enzymatic siRNA preparations, both the in vitro transcribed and chemically synthesized siRNAs were gel purified. Gel purification did not enhance the potency of the chemically synthesized siRNA, confirming that there is a fundamental difference between the siRNAs produced by the two methods. Three different methods to purify siRNAs prior to transfection: Phenol extraction/ethanol precipitation, gel purification, and column purification. Each of the methods yield siRNAs that are at least ten times as potent as equivalent siRNAs prepared by standard chemical synthesis.

Example 4

Potency of Chemical Versus Enzymatic Synthesis of siRNA-GAPDH

To confirm the general enhanced potency of enzymatically synthesized siRNAs and to confirm that the higher potency was due to a reduction in target mRNA concentration, siRNAs specific to GAPDH were compared for their capacity to reduce GAPDH mRNA levels in HeLa cells. Chemically synthesized and enzymatically synthesized siRNAs specific to the same target sequence in the 5' Medial Region of the GAPDH mRNA were prepared and transfected at varying concentrations into HeLa cells. The cells were harvested forty-eight hours after transfection. Total RNA from the samples was harvested, fractionated by agarose gel electrophoresis, and transferred to a membrane. The resulting Northern blot was incubated with a probe specific to the GAPDH mRNA. The relative abundance of GAPDH mRNA in the various samples was determined by imaging the probe signal on the Northern blot using a phosphorimager. Cyclophilin (a common housekeeping gene used for sample normalization) was assessed on the same Northern blots to normalize the samples.

Figure 11:
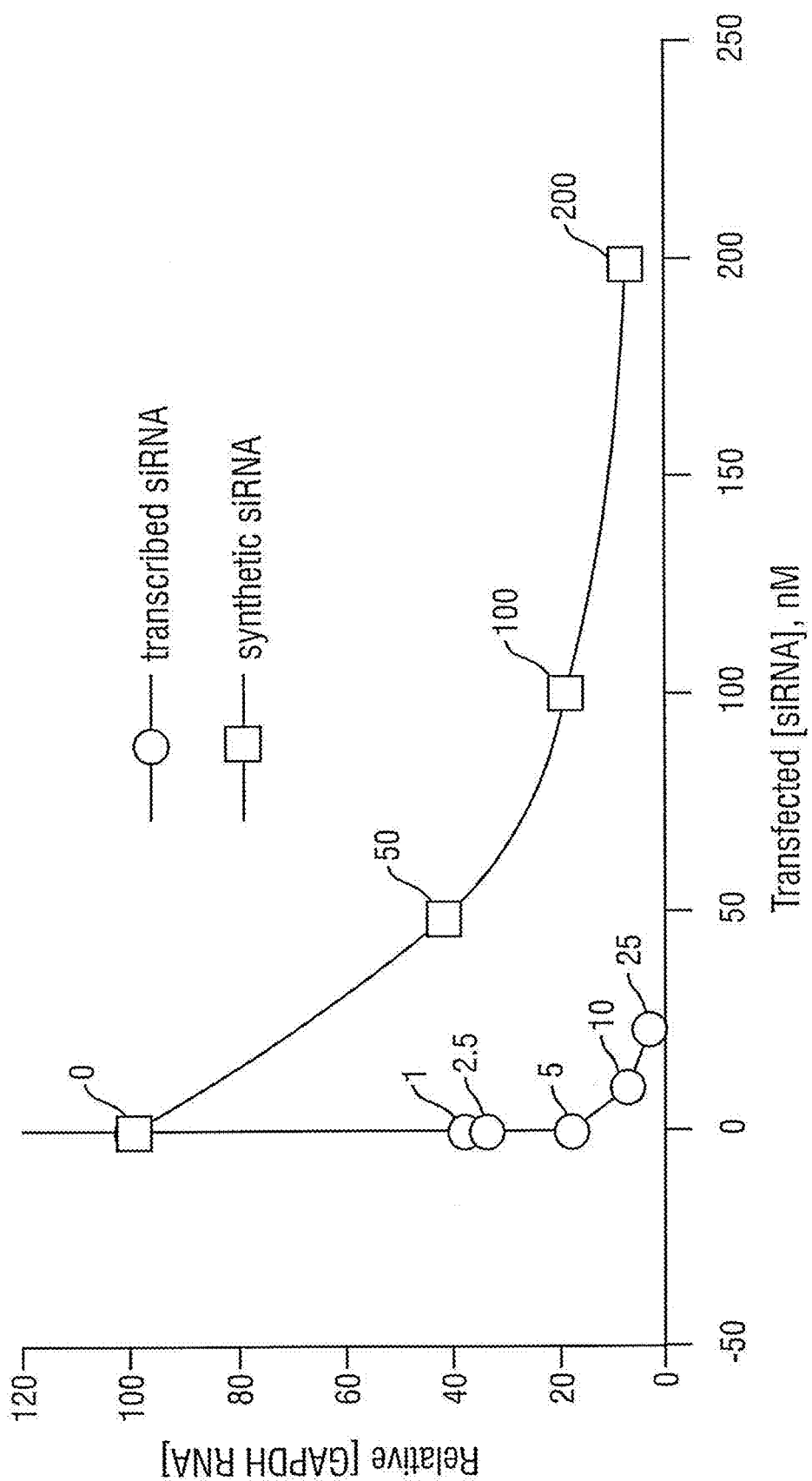
FIG. 11: Comparison of siRNA effectiveness between enzymatically synthesized and siRNA made through standard chemical synthesis in expression of GAPDH mRNA.

FIG. 11 shows the GAPDH signal normalized to cyclophilin in the samples treated with varying concentrations of the two siRNAs. Consistent with our results with c-myc, the in vitro transcribed siRNAs were ten- to twenty-fold more potent than the chemically synthesized siRNA to the same target sequence. This experiment confirms that the improved potency of enzymatically synthesized siRNAs is consistent for different gene targets and that the improved potency derives from an ability to decrease the concentration of the target mRNA and not through some other cellular process.

Example 5

SiRNA of Increased Potency Synthesis by RNA Copying (Via RNA Dependent RNA Polymerase)

Recombinant protein P2 of the double-stranded RNA bacteriophage phi6 (P2 replicase) is an RNA polymerase that binds single-stranded RNAs and synthesizes a complementary strand to create dsRNA (Makeyev and Bamford, 2000). P2 replicase was used to convert single-stranded 21mer oligonucleotides bearing sequence identical to or complementary to c-myc mRNA into 21mer dsRNAs. These dsRNAs were transfected into HeLa cells at concentrations of 5 or 10 nM in the cell culture medium. Seventy-two hours after transfection, the cells were counted. Reduction in c-myc protein levels limits cell-division, thus more potent siRNAs result in reduced numbers of cells.

Figure 12:
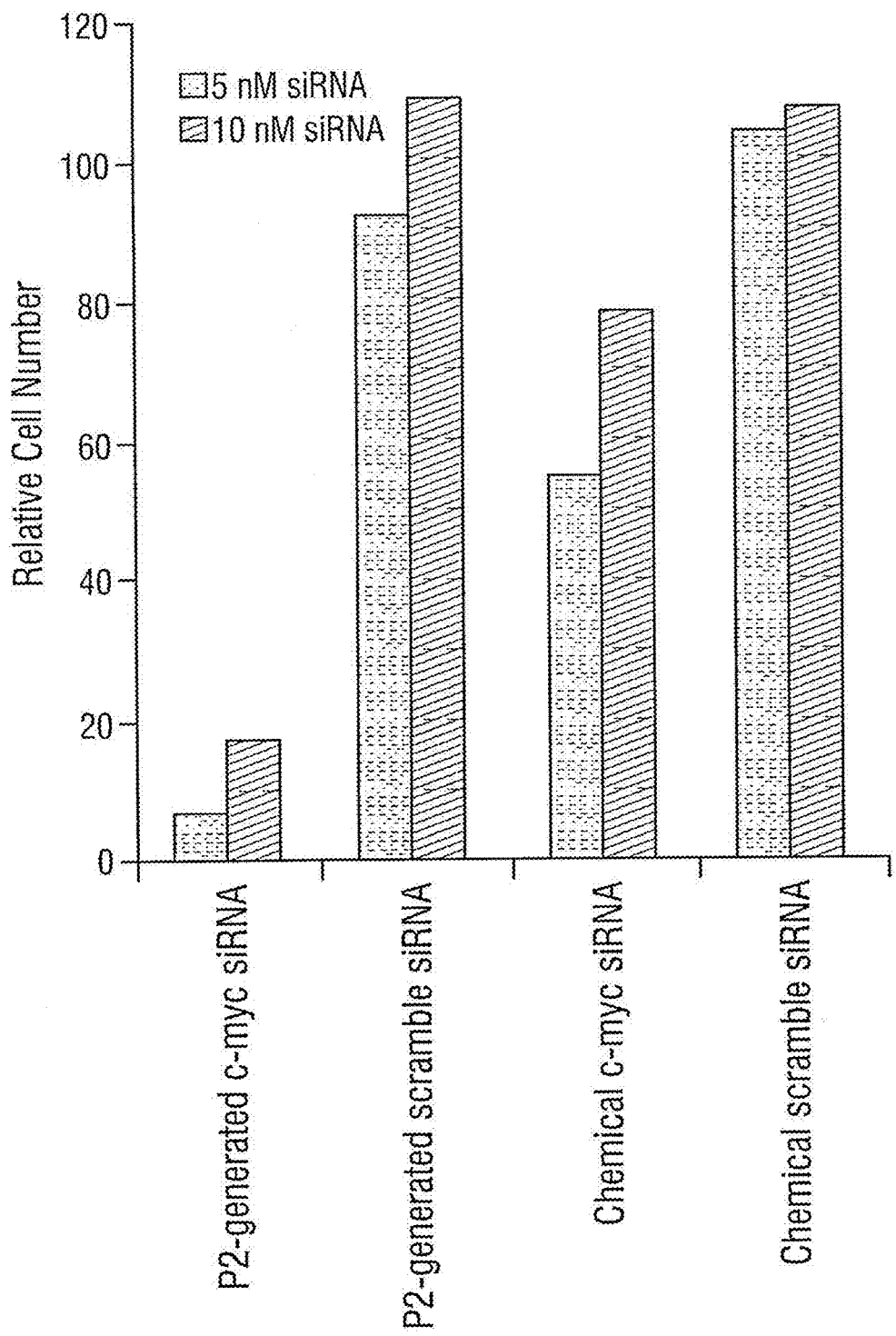
FIG. 12: Comparison of siRNA effectiveness between siRNA made through standard chemical synthesis and enzymatically synthesized siRNA via RNA copying in attenuation of c-myc mediated cell proliferation.

FIG. 12 shows the effect on cell growth of four different siRNAs transfected at two different concentrations. The first and second sets show cell numbers for cells transfected with chemically synthesized, single-stranded RNAs that had been converted to dsRNAs by P2 replicase. The first set was a dsRNA specific to the c-myc mRNA. The second set was a scrambled sequence bearing a nucleotide composition equivalent to the c-myc-specific siRNA. The third and fourth sets are c-myc-specific and scrambled sequence siRNAs whereby both strands were chemically synthesized. The P2 replicase-generated dsRNAs specific to c-myc are 10-20 fold more potent than the equivalent chemically synthesized siRNA (FIG. 12). The enhanced potency is sequence specific as the equivalently treated scrambled sequence has a profile equivalent to the chemically synthesized, scrambled sequence siRNA.

Surprisingly, both sense and anti-sense strand chemically synthesized RNA can be converted to siRNA of increased potency by the action of the P2 replicase (data not shown). These data indicate that the chemically synthesized anti-sense strand of the siRNA can target mRNA degradation as well as an enzymatically prepared RNA.

Example 6

Enzymatically Synthesized siRNA Incorporating Nucleotide Analogs

Parrish et al. (2000) found that several nucleotide analogs could be present in double-stranded RNAs without eliminating the capacity of the dsRNAs to suppress gene expression. However, Parrish et al. (2000) observed no particular benefit to using the nucleotide analogs in their studies.

Elbashir et al (2001) reported a slight improvement in the effectiveness of siRNAs that had 3' overhanging di-nucleotide deoxy-thymidines rather than ribo-uridines. Elbashir et al. suggested that the improvement might be due to improved nuclease stability of the deoxy-thymidines, though they also indicated that they saw improved yield of the siRNAs with the deoxy-thymidines which could translate to improved siRNA quality and thus an improved molecule for siRNA experiments.

A variety of nucleotide analogs were systematically tested for their capacity to improve the potency of siRNAs. Analogs of UTP, CTP, GTP, and ATP were incorporated by transcription into siRNAs specific to GAPDH. The siRNAs were prepared and transfected into HeLa cells. Forty-eight hours after transfection, the treated cells were harvested, total RNA was recovered, and the levels of GAPDH mRNA were assessed by Northern analysis. Cyclophilin (a common housekeeping gene used for sample normalization) and 28S rRNA were also probed to normalize the samples. Many of the analogs performed equivalently to the unmodified siRNA (FIG. 13), consistent with what Parrish et al (2000) had observed in their experiments. However, several analogs provided a 2-4-fold enhancement in siRNA potency, over and above the enhancement of potency resulting from enzymatic synthesis alone.

Interestingly, replacing an oxygen with a thiol on the bridging phosphate 5' to any of the four nucleotides improved the potency of the GAPDH-specific siRNA (see alpha-S ATP, alpha-S CTP, alpha-S GTP, alpha-S UTP). Each of these analogs are reported to provide some protection to nucleases (Black et al. (1972) "Studies on the Toxicity and Antiviral Activity of Various Polynucleotides," Antimicrob. Agents Chemotherap. 3, 198-206), though our work suggests that the level of protection is significantly less than two-fold (data not shown). Notably, each of the alpha-thio modified NTPs provide similar enhancements in siRNA potency. If nuclease stability was important in improving siRNA potency as was suggested (Elbashir 2001), then one would expect that the modified uridine would be more beneficial because it would ensure that the single-stranded, overhanging di-nucleotide remained intact.

Figure 13:
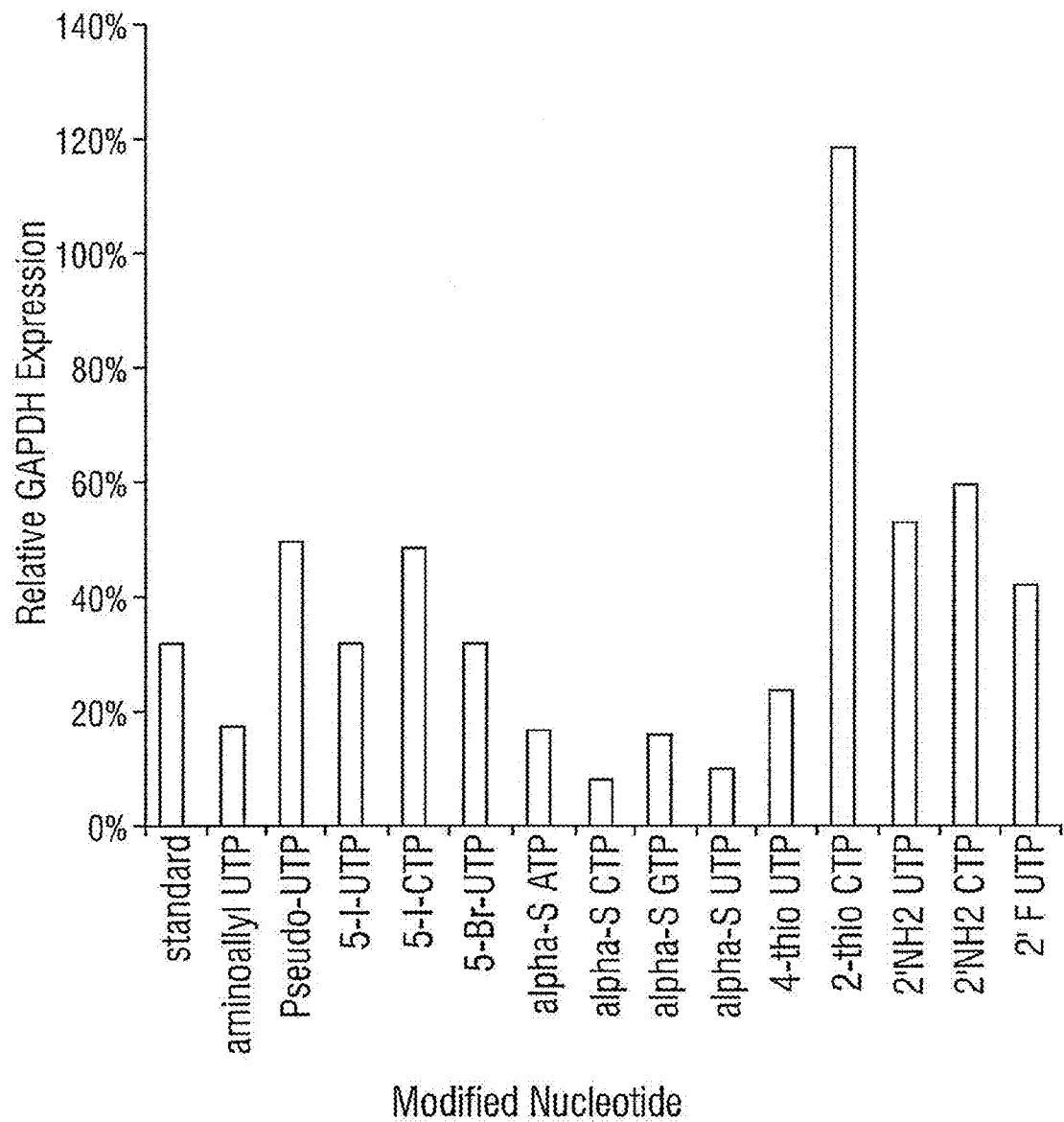
FIG. 13: Impact of Nucleotide Analogs on siRNA Potency in enzymatically synthesized siRNA.

Further evidence that nuclease stability is not that critical to siRNA potency is the observation that the siRNAs with 2'$NH_2$ Uridine and 2' $NH_2$ Cytidine as well as 2'F Uridine (these analogs are known to improve RNA stability) perform no better than the unmodified siRNAs (FIG. 13). Based on these data, it is not nuclease stability but rather the stability of the siRNA duplex that has a substantial impact on the potency of the siRNAs. Alpha-thio-nucleotides reduce the stability of the dsRNA duplex. Presumably, an early step in the gene silencing pathway is the dissociation of the double-stranded siRNA to facilitate hybridization of the siRNA to the mRNA target. Reducing the stability of the siRNA duplex would make it less difficult for the proteins involved in the gene silencing pathway to dissociate the anti-sense and sense strands of the siRNA, thus improving their potency. Analogs other than alpha-thio-NTPs that decrease dsRNA stability and thus would be expected to improve siRNA potency include 4-thio UTP, inosine triphosphate, 4-Ethyl CTP, etc.

To test this hypothesis, GAPDH-specific siRNAs with 4-thio UTP and 2-thio UTP were synthesized. The 2-thio modification stabilizes A-U base pairs whereas the 4-thio modification destabilizes A-U basepairs (Testa et al., 1999). If duplex stability truly is an important predictor of siRNA potency, then the 2-thio modified siRNA would reduce potency and the 4-thio modification would enhance potency. The data are consistent with this hypothesis (FIG. 13).

Example 7

Chemical Synthesis and Use of siRNAs with Reduced Duplex Stability

Standard and modified 21mer ribo-oligomers of the two sequences provided below were chemically synthesized using an Expedite Nucleic Acid Synthesis System™ (Applied Biosystems) and the associated synthesis program. Two types of phosphoramidites were used: 5'-O-DMT-N6-phenoxyacetyl)-2'-O-t-butyldimethylsilyl group (TBDMS)-nucleoside-3'-O—(B-cyanoethyl-N,N-diisopropylamino) phosphoramidite (Wu et al., 1989) and 5'-O-DMT-N6-phenoxyacetyl)-2' O-TriisopropylsilylOxyMethyl (TOM)-3'-O—(B-cyanoethyl-N,N-diisopropylamino) phosphoramidite. For both types of amidites, we followed the same basic procedure for coupling and deprotecting as described (Wincott et al. 1995). Following the addition of the last nucleotide, ribo-oligomers generated with either phosphoramidite were cleaved from the solid support with 40% aqueous methylamine and deprotected with tetrabutylammonium fluoride (Wincott 1995).

| Name | RNA Sequence (5' to 3') | SEQ ID NO: |
|---|---|---|
| 5' GAPDH sense | UGAUGGCAACAAUAUCCACdTdT | 33 |
| 5' GAPDH anti-sense | GUGGAUAUUGAAGCCAUCAdTdT | 34 |

Ribo-oligomers with phosphorothioates at defined positions were produced by incubating the elongating oligonucleotide with thiosulfonate for 30 seconds after the appropriate nucleoside was added (Iyer et al. 1990). Ribo-oligomers with 4-thio-U and inosine were produced by substituting a 4-thio-U phosphoramidite for the U precursor and an Inosine phosphoramidite for the G precursor in the standard synthesis procedure.

The incorporation of these modified nucleotide analogs, because they act to effectively reduce overall duplex stability in RNA duplexes, is expected to lead to substantially enhanced potency of the resultant siRNAs.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,415,732
U.S. Pat. No. 4,458,066
U.S. Pat. No. 4,682,195
U.S. Pat. No. 4,683,202
U.S. Pat. No. 4,786,600
U.S. Pat. No. 4,952,496
U.S. Pat. No. 5,026,645
U.S. Pat. No. 5,037,745
U.S. Pat. No. 5,102,802
U.S. Pat. No. 5,591,601
U.S. Pat. No. 5,645,897
U.S. Pat. No. 5,705,629
U.S. Pat. No. 5,795,715
U.S. Pat. No. 5,824,528
U.S. Pat. No. 5,869,320
U.S. Pat. No. 5,889,136
U.S. Pat. No. 5,891,681
U.S. Pat. No. 6,005,087
U.S. Pat. No. 6,114,152
U.S. Pat. No. RE35,443
Euro. Patent No. 178,863
Euro. Patent No. 266,032
WO 00/44914
WO 01/36646
WO 01/68836
WO 88/10,315
WO 91/02,818
WO 91/05,866
WO 99/32619
Anonymous, "The siRNA user guide." Revised Aug. 26, 2001, [online], [retrieved on Jan. 31, 2002] Retrieved from Max Planck Institute for Biophysical Chemistry.
Atschul, S. F. et al., J. Molec. Biol. 215:403 (1990).
Bergstrom D. E., Zhang, P. and Johnson W. T. (1997) Nucleic Acids Res. 25:1935-1942.
Bernstein, E, Caudy, A A, Hammond, S M, and Hannon, G J (2001). Role for a bidentate ribonuclease in the initiation step of RNA interference. Nature 409: 363-366.
Black et al. (1972) "Studies on the Toxicity and Antiviral Activity of Various Polynucleotides," Antimicrob. Agents Chemotherap. 3, 198-206.
Caplen, N J, Parrish, S, Imani, F, Fire, A, and Morgan, R A (2001). Specific inhibition of gene expression by small double-stranded RNAs in invertebrate and vertebrate systems. Proc Natl Acad Sci USA 98: 9742-9747.
Devereux, J., et al., Nucleic Acid. Res. 12(1):387 (1984).
Dharmacon Research. (July, 2001) siRNA Oligonucleotides for RNAi Applications: Dharmacon siACE-RNAi™ Options. Technical Bulletin #003. [online], [retrieved on Jan. 31, 2002].
Diaz et al., J. Mol. Biol. 229: 805-811 (1993).
Dubins, D N, Lee, A, Macgbregor, R B, and Chalikian, T V (2001). On the stability of double stranded nucleic acids. J. Am. Chem. Soc. 123:9254-59.
Elbashir, S M, Harborth, J, Lendeckel, W, Yalcin, A, Weber, K, and Tuschl, T (2001). Duplexes of 21-nucleotide RNAs mediate RNA interference in cultured mammalian cells. Nature 411: 494-498.
Fire, A, Xu, S, Montgomery, M K, Kostas, S A, Driver, S E, and Mello, C C (1998). Potent and specific genetic interference by double-stranded RNA in Caenorhabditis elegans. Nature 391: 806-811.
Froehler, et al. (1986). Synthesis of DNA via deoxynucleoside H-phosphonate intermediates. Nucleic Acids Res. 14(13):5399-407.
Fuerst, T. R. et al. (1987) Molecular and Cellular Probes 7, 2538-2544.
Grishok, A, Pasquinelli, A E, Conte, D, Li, N, Parrish, S, Ha, I, Baillie, D L, Fire, A, Ruvkun, G, and Mello, C C (2001). Genes and mechanisms related to RNA interference regulate expression of the small temporal RNAs that control C. elegans developmental timing. Cell 106: 23-34.
Hamilton, A J, and Baulcombe, D C (1999). A species of small antisense RNA in posttranscriptional gene silencing in plants. Science 286: 950-952.
Hammond, S M, Boettcher, S, Caudy, A A, Kobayashi, R, and Hannon, G J (2001). Argonaute2, a link between genetic and biochemical analyses of RNAi. Science 293: 1146-1150.
Hebert E J, Grimsley G R, Hartley R W, Horn G, Schell D, Garcia S, Both V, Sevcik J, and Pace C N. (1997). Purification of ribonucleases Sa, Sa2, and Sa3 after expression in Escherichia coli. Protein Expr. Purif. 11, 162-8.
Higgins, D. G., Bleasby, A. J. and Fuchs, R. (1992) CLUSTAL V: improved software for multiple sequence alignment. Computer Applications in the Biosciences (CABIOS), 8(2):189-191.
Hutvagner, G., McLachlan, J., Pasquinelli, A. E., Balint, E., Tuschl, T., and Zamore, P. D. (2001). A cellular function for the RNA-interference enzyme Dicer in the maturation of the let-7 small temporal RNA. Science 293: 834-838.

Iyer R P, Egan W, Regan J B, Beaucage S L (1990) J. Am. Chem. Soc. 112, 1253-1254.

Kawase, Y., Iwai, S., Inoue, H., Miura, K. and Ohtsuka E. (1986) *Nucleic Acids Res.* 19:7727-7736.

Kievits, T. et al. Journal of Virological Methods 35, 273-286 (1991).

Kimura S, Maekawa T, Hirakawa K, Murakami A and Abe T (1995). Alterations of c-myc expression by antisense oligodeoxynucleotides enhance the induction of apoptosis in HL-60 cells. Cancer Research 55: 1379-1384.

Knight, S W, and Bass, B L (2001). A Role for the RNase III Enzyme DCR-1 in RNA Interference and Germ Line Development in *C. elegans*. Science 2: 2.

Kwoh, D. Y. et al. Proc. Natl. Acad. Sci. USA 86, 1173-1177 (1989).

Lesk, A. M., ed., (1988). Computational Molecular Biology. Oxford University Press, New York, 1988.

Makeyev E V, Bamford D H [2000] "Replicase activity of purified recombinant protein P2 of double-stranded RNA bacteriophage phi6," EMBO J 19:124-33.

Milligan, J. F., Groebe, D. R., Witherell, G. W. and Uhlenbeck, O. C. (1987) Nucleic Acids Res. 25, 8783-8798

Montgomery, M K, Xu, S and Fire, A (1998). RNA as a target of double-stranded RNA-mediated genetic interference in *Caenorhabditis elegans*. Proc Natl Acad Sci USA 95: 15502-15507.

Nguyen H K, Auffray P, Asseline U, Dupret D, Thuong N T (1997) Nucl. Acids Res. 25, 3059-65.

Pace C N, Hebert E J, Shaw K L, Schell D, Both V, Krajcikova D, Sevcik J, Wilson K S, Dauter Z, Hartley R W, and Grimsley G R (1998). Conformational stability and thermodynamics of folding of ribonucleases Sa, Sa2 and Sa3. J. Mol. Biol. 279, 271-86.

Parrish et al. (2000) Functional anatomy of a dsRNA trigger: differential requirement for the two trigger strands in RNA interference. Mol Cell. 6(5):1077-87.

Ryan, K M and Birnie G D (1996). Myc oncogenes: the enigmatic family. Biochem. J. 314: 713-721.

Sambrook, J, Russell D W (2001) *Molecular Cloning*, Cold Spring Harbor Laboratory Press.

Shishkina, I. G. and F. Johnson, Chem Res Toxicol, 2000, 13, 907-912.

Smith, D. W., ed. (1986) Biocomputing: Informatics and Genome Projects. Academic Press, New York, 1993.

Stein, C A (2001) The experimental use of antisense oligonucleotides: a guide for the perplexed. J. Clinical Invest. 108: 641-644.

Testa S M, Disney M D, Turner D H, Kierzek R (1999) "Thermodynamics of RNA-RNA Duplexes with 2- or 4-thiouridines," Biochemistry 38, 16655-62.

Thompson J. D., Higgins D. G., Gibson T. J. "CLUSTAL W: improving the sensitivity of progressive multiple sequence alignment through sequence weighting, position-specific gap penalties and weight matrix choice." Nucleic Acids Res. 22:4673-4680 (1994).

Wincott F, DiRenzo A, Grimm S, Tracz D, Workman C, Sweedler D, Gonzalez C, Scaringe S, Usman N (1995) "Synthesis, Deprotection, analysis and Purification of RNA and Ribozymes," Nucl. Acids Res. 23, 2677-2684.

Wu, T., Ogilvie, K. K., and Pon, R. T. (1989) Nucl. Acids Res. 17, 3501-3517.

Zamore, P D, Tuschl, T, Sharp, P A, and Bartel, D P (2000). RNAi: double-stranded RNA directs the ATP-dependent cleavage of mRNA at 21 to 23 nucleotide intervals. Cell 101: 25-33.

---

What is claimed is:

1. A method for attenuating the expression of a target gene in a cell comprising:
   introducing siRNA into the cell in an amount sufficient to attenuate expression of the target gene
   wherein the siRNA is from 15 to 30 nucleotides in length and contains a duplex of from 15 to 30 contiguous nucleotides, and the siRNA is made by a method comprising:
   obtaining a first polynucleotide template comprising a first promoter operatively linked to a first target sequence that has 5' and 3' ends and that is substantially identical to at least a portion of the target gene;
   obtaining a second polynucleotide template comprising a second promoter operatively linked to a second target sequence that has 5' and 3' ends and that is substantially the reverse complement of the first target sequence of the first template;
   enzymatically incorporating nucleotides into RNA by contacting the first template with a reaction mixture comprising an RNA polymerase and nucleotides to transcribe the first template to form a first RNA product;
   enzymatically incorporating nucleotides into RNA by contacting the second template with a reaction mixture comprising an RNA polymerase and nucleotides to transcribe the second template to form a second RNA product;
   annealing the first and second RNA products to form a siRNA containing a duplex of from 15 to 30 contiguous nucleotides, and
   contacting the siRNA with a single strand specific ribonuclease,
   wherein the siRNA has a sequence that is substantially identical to at least a portion of the target gene,
   wherein the nucleotides of at least one incorporating step comprise at least one modified nucleotide analog selected from the group consisting of alpha-S ATP, alpha-S CTP, alpha-S GTP, and alpha-S UTP,
   wherein the at least one modified nucleotide analog is incorporated into the siRNA, and
   wherein fewer molecules of the siRNA are effective in achieving attenuation of gene expression when compared to the number of standard siRNA molecules required to achieve the same level of attenuation of target gene expression.

2. The method of claim 1, wherein the single strand specific ribonuclease is RNase T1, RNase A, RNase Sa, RNase Sa2, or RNase Sa3.

3. The method of claim 1, wherein the first template further comprises an overhang encoding sequence joined to the 3' end of the first target sequence and the second template further comprises an overhang encoding sequence joined to the 3' end of the second target sequence.

4. The method of claim 3, wherein the first and second overhang encoding sequences each comprise TT.

5. The method of claim 3, wherein the first two nucleotides of the 5' end of the first target sequence are GG and the last two nucleotides of the 3' end of the first target sequence are CC.

6. The method of claim 3, wherein the first two nucleotides of the 5' end of the first target sequence are GA and the last two nucleotides of the 3' end of the first target sequence are TC.

7. The method of claim 1, wherein the first target sequence is 15, 16, 17, 18, 19, 20, 21, 22, 23, 24, 25, 26, 27, 28, 29 or 30 nucleotides in length.

8. The method of claim 1, wherein the first promoter is a T7, T3, or SP6 promoter.

9. The method of claim 1, wherein the second promoter is a T7, T3, or SP6 promoter.

10. The method of claim 1, wherein the first promoter and the second promoter are the same promoter.

11. The method of claim 1, wherein the first promoter and the second promoter are different promoters.

12. The method of claim 1, wherein the first template further comprises a first leader sequence of about 10 nucleotides positioned between the first promoter and the first target sequence.

13. The method of claim 12, wherein the second template further comprises a second leader sequence of about 10 nucleotides positioned between the second promoter and the second target sequence.

14. The method of claim 13, wherein the second leader sequence is substantially non-complementary to the first leader sequence.

15. The method of claim 1, wherein the cell is comprised within a tissue.

16. The method of claim 1, wherein the cell is comprised within an organism.

17. The method of claim 16, wherein the organism is a plant, animal, protozoan, virus, bacterium, or fungus.

18. The method of claim 17, wherein the organism is an animal.

* * * * *